(12) United States Patent
Berger et al.

(10) Patent No.: US 8,388,968 B2
(45) Date of Patent: Mar. 5, 2013

(54) COMPOSITIONS AND METHODS FOR INCREASING MUSCLE GROWTH

(75) Inventors: Catrin Berger, Germering (DE); Tanja Herrmann, München (DE); Chris Lu, Lexington, MA (US); Kelly-Ann Sheppard, Walpole, MA (US); Estelle Trifilieff, Dietwiller (FR); Stefanie Urlinger, München (DE)

(73) Assignee: Novartis AG, Basel (CH)

( * ) Notice: Subject to any disclaimer, the term of this patent is extended or adjusted under 35 U.S.C. 154(b) by 204 days.

(21) Appl. No.: 12/767,509

(22) Filed: Apr. 26, 2010

(65) Prior Publication Data

US 2010/0272734 A1    Oct. 28, 2010

Related U.S. Application Data

(60) Provisional application No. 61/173,004, filed on Apr. 27, 2009, provisional application No. 61/306,137, filed on Feb. 19, 2010.

(51) Int. Cl.
*A61K 39/395* (2006.01)
*C07K 16/28* (2006.01)

(52) U.S. Cl. ............... 424/143.1; 424/141.1; 424/142.1; 530/388.1; 530/388.15; 530/388.22

(58) Field of Classification Search .................. None
See application file for complete search history.

(56) References Cited

U.S. PATENT DOCUMENTS

| | | | |
|---|---|---|---|
| 6,656,475 B1 | 12/2003 | Lee et al. | |
| 6,682,736 B1 | 1/2004 | Hanson et al. | |
| 6,696,260 B1 | 2/2004 | Lee et al. | |
| 6,891,082 B2 | 5/2005 | Lee et al. | |
| 7,037,498 B2 | 5/2006 | Cohen et al. | |
| 7,807,155 B2 | 10/2010 | Di Padova et al. | |
| 2005/0014733 A1 | 1/2005 | Whittenmore et al. | |
| 2005/0257278 A1 | 11/2005 | Lee et al. | |
| 2006/0008846 A1 | 1/2006 | Vale et al. | |
| 2006/0034831 A1 | 2/2006 | Tobin et al. | |
| 2006/0068468 A1 | 3/2006 | Knopf et al. | |
| 2006/0251632 A1* | 11/2006 | Tremblay et al. | 424/93.21 |

FOREIGN PATENT DOCUMENTS

| | | |
|---|---|---|
| WO | WO 99/06559 A1 | 2/1999 |
| WO | WO 02/10214 A2 | 2/2002 |
| WO | WO 2007/067616 A2 | 6/2007 |
| WO | 2008/097541 | 8/2008 |
| WO | 2007/109668 | 7/2009 |

OTHER PUBLICATIONS

Bogdanovich et al. Myostatin blockade improves function but not histopathology in a murine model of limb-girdle muscular dystrophy 2C. Muscle Nerve. Mar. 2008;37(3):308-16.*
Holzbaur et al. Myostatin inhibition slows muscle atrophy in rodent models of amyotrophic lateral sclerosis. Neurobiol Dis. Sep. 2006;23(3):697-707. Epub Jul. 11, 2006*
Zhou et al. Reversal of cancer cachexia and muscle wasting by ActRIIB antagonism leads to prolonged survival. Cell. Aug. 20, 2010;142(4):531-43.*
R&D Systems Catalog No. AF339 [online], Oct. 13, 2008 [retrieved on Jun. 15, 2012]. Retrieved from the Internet:<URL: http://www.rndsystems.com/pdf/af339.pdf>.*
Bogdanovich et al., "Functional improvement of dystrophic muscle by myostatin blockade", Nature, 2002 vol. 420 pp. 418-421.
Bradley et al., "Myostatin as a therapeutic target for musculoskeletal disease", Cell. Mol. Life Sci., 2008 vol. 65 pp. 2119-2124.
Whittenmore et al., "Inhibition of myostatin in adult mice increases skeletal muscle mass and strength", Biochemical and Biophysical Research Communications, 2003 vol. 300 pp. 965-971.
SPE Helms, Publication date: Jun. 13, 2007; downloaded from internet on Sep. 21, 2012.
Clackson et al., Nature, 352:624-628 (1991).
Portolano et al., The Journal of Immunology, 150(3):880-887 (1993).
USPTO News: Biotechnology Art Group Discusses Enablement of Antibody Claims, C. Singer, Patent Docs, Biotech & Pharma Patent Law & News Blog, pp. 1-3, Jun. 14, 2007.
Lee et al., Proceedings of the National Academy of Sciences of the United States of America, 102(50):18117-18122 (2005).

* cited by examiner

*Primary Examiner* — David Romeo
(74) *Attorney, Agent, or Firm* — Frank Wu

(57) ABSTRACT

This disclosure is in the field of anti-Activin receptor IIB (ActRIIB) antibodies. In particular, it relates to the use of said antibodies for treating muscle disorders, such as muscle wasting due to disease or disuse.

34 Claims, 9 Drawing Sheets

COMPOSITIONS AND METHODS FOR INCREASING MUSCLE GROWTH

RELATED APPLICATIONS

This application claims priority to U.S. Provisional Application Ser. No. 61/173,004, filed 27 Apr. 2009, and U.S. Provisional Application Ser. No. 61/306,137, filed 19 Feb. 2010, the contents of which are incorporated herein by reference in their entirety.

TECHNICAL FIELD

This disclosure is in the field of anti-Activin receptor IIB (ActRIIB) antibodies. In particular, it relates to the use of said antibodies for treating muscle disorders, such as muscle wasting due to disease or disuse.

BACKGROUND ART

Activins are dimeric growth and differentiation factors which belong to the transforming growth factor-beta (TGF-beta) superfamily of structurally related signaling proteins. Activins signal through a heterodimeric complex of receptor serine kinases which include at least two type I (I and IB) and two type II (II and IIB, aka ACVR2A and ACVR2B) receptors. These receptors are all transmembrane proteins, composed of a ligand-binding extracellular domain with cysteine-rich region, a transmembrane domain, and a cytoplasmic domain with predicted serine/threonine specificity. Type I receptors are essential for signalling while type II receptors are required for binding ligands and for expression of type I receptors. Type I and II receptors form a stable complex after ligand binding resulting in the phosphorylation of type I receptors by type II receptors.

The activin receptor II B (ActRIIB) is a receptor for myostatin. The interaction between myostatin and this receptor regulates the inhibition of skeletal muscle differentiation via the Smad-dependent pathway. Thus, by inhibiting or preventing myostatin from binding to ActRIIB, one can induce the formation of skeletal muscle.

Various groups have looked into this. Bogdanovich et al (Nature, 2002, 420:418-421) describes that anti-myostatin antibodies were able to block myostatin, resulting in an increase in muscle mass in a mouse model of Duchenne muscular dystrophy. Bradley et al (Cell Mol. Life. Sci. 2008, 65:2119-2124) have reviewed the different available approaches for modulating the myostatin/ActRIIB interaction, including the aforementioned anti-myostatin antibodies, inhibiting the release of mature myostatin by administering the myostatin propeptide, administering follistatin to block the myostatin receptor, administering HDAC inhibitors to induce follistatin production, administering an altered myostatin peptide which prevents myostatin from binding the receptor and administering a soluble decoy receptor for myostatin.

Despite these potential therapies, there is no product available for the treatment of patients. Indeed, recently one company cancelled its anti-myostatin antibody project.

There is therefore a need for a method of increasing muscle mass and strength in a patient.

DISCLOSURE OF THE INVENTION

It has been discovered that antibodies directed to the ActRIIB receptor can prevent myostatin from binding to the receptor, thus preventing the inhibition of muscle differentiation by the Smad-dependent pathway. This leads to an increase in muscle mass and strength in a patient.

Therefore, in one aspect, the disclosure provides an anti-ActRIIB antibody, or a functional fragment thereof or functional protein comprising an antigen-binding portion of an anti-ActRIIB antibody. In one embodiment, the ActRIIB is human ActRIIB. The polypeptide sequence of human ActRIIB is recited in SEQ ID NO: 181 (AAC64515.1, GI:3769443). In one embodiment, the antibody or functional protein is from a mammal, having an origin such as human or camelid. Thus the antibody may be a chimeric, human or a humanized antibody. In a particular embodiment, the anti-ActRIIB antibody is characterized as having antigen-binding region that is specific for the target protein ActRIIB and binds to ActRIIB or a fragment of ActRIIB. In one embodiment, the antibody is suitable for use in therapy.

In one embodiment, the antibodies according to the disclosure are ActRIIB antagonists with no or low agonistic activity. In another embodiment, the antibody or functional fragment comprising an antigen-binding portion binds the target protein ActRIIB and decreases the binding of myostatin to ActRIIB to a basal level. In one aspect of this embodiment, the antibody or functional fragment reduces the amount of myostatin that binds to ActRIIB. In a further aspect of this embodiment, the antibody or functional fragment completely prevents myostatin from binding to ActRIIB. In a further embodiment, the antibody or functional fragment inhibits Smad activation. In a further embodiment, the antibody or functional fragment inhibits activin receptor type IIB mediated myostatin-induced inhibition of skeletal differentiation via the Smad-dependent pathway.

The binding may be determined by one or more assays that can be used to measure an activity which is either antagonism or agonism by the antibody. In one embodiment, the assays measure at least one of the effects of the antibody on ActRIIB that include: inhibition of myostatin binding to ActRIIB by ELISA, inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay).

In one embodiment, the disclosure provides antibodies that specifically bind to the myostatin binding region (i.e. ligand binding domain) of ActRIIB. This ligand binding domain consists of amino acids 19-134 of SEQ ID NO: 181 and has been assigned SEQ ID NO: 182 herein.

In one embodiment, the antibodies bind to ActRIIB with a $K_D$ of 100 nM or less, 10 nM or less, 1 nM or less. In one embodiment, the antibodies of the disclosure bind to ActRIIB with an affinity of 100 pM or less (i.e. 100 pM, 50 pM, 10 pM, 1 pM or less). In one embodiment, the antibodies of the disclosure bind to ActRIIB with an affinity of between 10 and 20 pM.

In one embodiment, the antibodies of the disclosure do not cross-react with an ActRIIB related protein, and more particularly do not cross-react with human ActRIIA (NP_001607.1, GI:4501897).

In one embodiment, the antibodies of the disclosure in one embodiment bind to ActRIIB rather than ActRIIA. In one embodiment, the antibodies of the disclosure bind to ActRIIB with 5-fold greater affinity than they bind to ActRIIA, more particularly 10-fold, still more particularly 50-fold, still more particularly 100-fold.

In one embodiment, the antibodies of the disclosure bind to ActRIIA with an affinity of 100 pM or more (i.e. 250 pM, 500 pM, 1 nM, 5 nM or more).

In one embodiment the antibodies of the disclosure are of the IgG2 isotype.

In another embodiment, the antibodies of the disclosure are of the IgG1 isotype. In a further embodiment, the antibodies of the disclosure are of the IgG1 isotype and have an altered effector function through mutation of the Fc region. In one embodiment, said altered effector function is reduced ADCC and CDC activity. In one embodiment, said altered effector function is silenced ADCC and CDC activity.

In another related embodiment, the antibodies according to the disclosure are fully human or humanized IgG1 antibodies with no antibody dependent cellular cytotoxicity (ADCC) activity or CDC activity and bind to a region of ActRIIB consisting of amino acids 19-134 of SEQ ID NO:181.

In another related embodiment, the antibodies according to the disclosure are fully human or humanized IgG1 antibodies with reduced antibody dependent cellular cytotoxicity (ADCC) activity or CDC activity and bind to a region of ActRIIB consisting of amino acids 19-134 of SEQ ID NO:181.

The present disclosure relates to isolated antibodies, particularly human or humanized antibodies that inhibit myostatin binding to ActRIIB and activate skeletal muscle differentiation in vitro and in vivo. In certain embodiments, the antibodies of the disclosure are derived from particular heavy and light chain sequences and/or comprise particular structural features such as CDR regions comprising particular amino acid sequences. The disclosure provides isolated antibodies, methods of making such antibodies, immunoconjugates and multivalent or multi-specific molecules comprising such antibodies and pharmaceutical compositions containing the antibodies, immunoconjugates or bi-specific molecules of the disclosure. The disclosure also relates to methods of using the antibodies to inhibit, i.e. antagonize, function of ActRIIB in order to inhibit Smad activation and thereby induce skeletal muscle differentiation, for example, resulting in the treatment of a pathological disorder.

The pathological disorder may be a musculoskeletal disease or disorder, such as muscle atrophy. There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barré syndrome, peripheral neuropathy, or exposure to environmental toxins or drugs).

In addition, the muscle atrophy can be a result of myopathy, such as myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositisis; polymyositis; inclusion body myositis; myositis ossificans; rhabdomyolysis and myoglobinurias.

The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. The musculoskeletal disease can also be osteoporosis, a bone fracture, short stature, or dwarfism.

In addition, the muscle atrophy can be a result of an adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, renal failure, congestive heart failure, ageing, space travel or time spent in a zero gravity environment.

Examples of age-related conditions that may be treated include, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, frailty, memory loss, wrinkles, impaired kidney function, and age-related hearing loss; metabolic disorders, including Type II Diabetes, Metabolic Syndrome, hyperglycemia, and obesity.

Other conditions that may be treated with the antibodies of the disclosure include acute and/or chronic renal disease or failure, liver fibrosis or cirrhosis, cancer such as breast cancer, Parkinson's Disease; conditions associated with neuronal death, such as ALS, brain atrophy, or dementia and anemia.

Further conditions include cachexia, cachexia associated with a rheumatoid arthritis and cachexia associated with cancer.

To date, very few reliable or effective therapies have been developed to treat these disorders.

Based on reported evidence of a role of activins binding to ActRIIB amongst other receptors (Werner and Alzheimer, Cytokine Growth Factors Rev 2006, 17 (3):157-171), in contributing to liver, kidney and pulmonary fibrosis and of a role for myostatin, activins, or ActRIIB in cancers (Tsuchida et al, Endo J, 2008, 55(1):11-21) the antibodies of the disclosure may be used to treat liver, kidney, pulmonary fibrosis and cancers exemplified by but not restricted to rhabdomyosarcomas, bone-loss inducing cancers, hepatocellular carcinomas, gastrointestinal cancers.

The prevention may be complete, e.g., the total absence of an age-related condition or metabolic disorder. The prevention may also be partial, such that the likelihood of the occurrence of the age-related condition or metabolic disorder in a subject is less likely to occur than had the subject not received an antibody of the present disclosure.

In order that the present disclosure may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction.

Penultimate processes typically include nuclear events, resulting in a change in gene expression.

The term ActRIIB or Act IIB receptor refers to human ActRIIB as defined in SEQ ID NO: 181 (AAC64515.1, GI:3769443). Research grade polyclonal and monoclonal anti-ActRIIB antibodies are known in the art, such as those made by R&D Systems®, MN, USA. Therapeutic anti-ActRIIB antibodies have not previously been described. Of course, antibodies could be raised against ActRIIB from other species and used to treat pathological conditions in those species.

The term "antibody" as referred to herein includes whole antibodies and any antigen binding fragment (i.e. "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g. a portion of ActRIIB) It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g. Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g. an isolated antibody that specifically binds ActRIIB is substantially free of antibodies that specifically bind antigens other than ActRIIB). An isolated antibody that specifically binds ActRIIB may, however, have cross-reactivity to other antigens, such as ActRIIB molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g. human germline sequences, or mutated versions of human germline sequences or antibody containing consensus framework sequences derived from human framework sequences analysis, for example, as described in Knappik, et al. (2000. J Mol Biol 296, 57-86).

The human antibodies of the disclosure may include amino acid residues not encoded by human sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g. a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g. a mouse) that is transgenic or transchromosomal for human immunoglobulin genes or a hybridoma prepared therefrom, antibodies isolated from a host cell transformed to express the human antibody, e.g. from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g. IgM, IgE, IgG such as IgG1 or IgG2) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to ActRIIB polypeptide" is intended to refer to an antibody that binds to human ActRIIB polypeptide with a $K_D$ of a 100 nM or less, 10 nM or less, 1 nM or less. An antibody that "cross-reacts with an antigen other than ActRIIB" is intended to refer to an antibody that binds that antigen with a $K_D$ of $10 \times 10^{-9}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5\text{-}10 \times 10^{-8}$ M, or $1 \times 10^{-7}$ M or greater. In certain embodiments, such antibodies that do not cross-react with the antigen exhibit essentially undetectable binding against these proteins in standard binding assays. $K_D$ may be determined using a biosensor system, such as a Biacore® system, or Solution Equilibrium Titration.

As used herein, the term "antagonist antibody" is intended to refer to an antibody that inhibits ActRIIB induced signaling activity in the presence of myostatin. Examples of an assay to detect this include inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay).

In some embodiments, the antibodies inhibit myostatin induced signalling as measured in a Smad dependent reporter gene assay at an IC50 of 10 nM or less, 1 nM or less, or 100 pM or less.

As used herein, an antibody with "no agonistic activity" is intended to refer to an antibody that does not significantly increase ActRIIB mediated signaling activity in the absence of myostatin in a cell-based assay, such as inhibition of myostatin induced signalling (for instance by a Smad dependent reporter gene assay), inhibition of myostatin induced Smad phosphorylation (P-Smad ELISA) and inhibition of myostatin induced inhibition of skeletal muscle cell differentiation (for instance by a creatine kinase assay). Such assays are described in more details in the examples below.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, such as the biosensor system of Biacore®, or Solution Equilibrium Titration (SET) (see Friguet B et al. (1985) J. Immunol. Methods; 77(2): 305-319, and Hanel C et al. (2005) Anal Biochem; 339(1): 182-184).

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

As used herein, the term "ADCC" or "antibody dependent cellular cytotoxicity" activity refers to human B cell depleting activity. ADCC activity can be measured by the human B cell depleting assays known in the art.

In order to get a higher avidity probe, a dimeric conjugate (two molecules of an antibody protein coupled to a FACS marker) can be constructed, thus making low affinity interactions (such as with the germline antibody) more readily detected by FACS. In addition, another means to increase the avidity of antigen binding involves generating dimers, trimers or multimers of any of the constructs described herein of the anti-ActRIIB antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in ActRIIB hybrids to create such higher order structures. For example, it is possible to use multimerizing domains such as the trimerizing domain described in WO2004/039841 or pentamerizing domain described in WO98/18943.

As used herein, the term "selectivity" for an antibody refers to an antibody that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g. mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells, however optimized expression of these sequences in other eukaryotic cells is also envisioned herein. The amino acid sequences encoded by optimized nucleotide sequences are also referred to as optimized.

Various aspects of the disclosure are described in further detail in the following subsections.

Standard assays to evaluate the binding ability of the antibodies toward ActRIIB of various species are known in the art, including for example, ELISAs, western blots and RIAs. Suitable assays are described in detail in the Examples. The binding affinity of the antibodies also can be assessed by standard assays known in the art, such as by Biacore analysis or Solution Equilibrium Titration. Surface plasmon resonance based techniques such as Biacore can determine the binding kinetics which allows the calculation of the binding affinity. Assays to evaluate the effects of the antibodies on functional properties of ActRIIB (e.g. receptor binding, preventing or inducing human B cell proliferation or IgG production) are described in further detail in the Examples.

Accordingly, an antibody that "inhibits" one or more of these ActRIIB functional properties (e.g. biochemical, immunochemical, cellular, physiological or other biological activities, or the like) as determined according to methodologies known to the art and described herein, will be understood to relate to a statistically significant decrease in the particular activity relative to that seen in the absence of the antibody (e.g. or when a control antibody of irrelevant specificity is present). An antibody that inhibits ActRIIB activity effects such a statistically significant decrease by at least 10% of the measured parameter, by at least 50%, 80% or 90%, and in certain embodiments an antibody of the disclosure may inhibit greater than 95%, 98% or 99% of ActRIIB functional activity.

The terms "cross-block", "cross-blocked" and "cross-blocking" are used interchangeably herein to mean the ability of an antibody or other binding agent to interfere with the binding of other antibodies or binding agents to ActRIIB, particularly the ligand binding domain, in a standard competitive binding assay.

The ability or extent to which an antibody or other binding agent is able to interfere with the binding of another antibody or binding molecule to ActRIIB, and therefore whether it can be said to cross-block according to the disclosure, can be determined using standard competition binding assays. One suitable assay involves the use of the Biacore technology (e.g. by using a BIAcore instrument (Biacore, Uppsala, Sweden)), which can measure the extent of interactions using surface plasmon resonance technology. Another assay for measuring cross-blocking uses an ELISA-based approach. A further assay uses FACS analysis, wherein competition of various antibodies for binding to ActRIIB expressing cells is tested (such as described in the Examples).

According to the disclosure, a cross-blocking antibody or other binding agent according to the disclosure binds to ActRIIB in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination.

An antibody is defined as cross-blocking an anti-ActRIIB antibody of the disclosure in an ELISA assay, if the test antibody is able to cause a reduction of anti-ActRIIB antibody binding to ActRIIB of between 60% and 100%, specifically between 70% and 100%, and more specifically between 80% and 100%, when compared to the positive control wells (i.e. the same anti-ActRIIB antibody and ActRIIB, but no "test" cross-blocking antibody). Examples of cross blocking antibodies as cited herein are MOR08159 and MOR08213. Thus, the disclosure provides antibodies that cross block MOR08159 or MOR08213 for binding to ActRIIB.

Recombinant Antibodies

Antibodies of the disclosure include the human recombinant antibodies, isolated and structurally characterized, as described in the Examples. The $V_H$ amino acid sequences of isolated antibodies of the disclosure are shown in SEQ ID NOs: 99-112. The $V_L$ amino acid sequences of isolated antibodies of the disclosure are shown in SEQ ID NOs: 85-98 respectively. Examples of particular full length heavy chain amino acid sequences of antibodies of the disclosure are shown in SEQ ID NOs: 146-150 and 156-160. Examples of particular full length light chain amino acid sequences of antibodies of the disclosure are shown in SEQ ID NOs: 141-145 and 151-155 respectively. Other antibodies of the disclosure include amino acids that have been mutated by amino acid deletion, insertion or substitution, yet have at least 60, 70, 80, 90, 95, 97 or 99 percent sequence identity in the CDR regions with the CDR regions depicted in the sequences described above. In some embodiments, it includes mutant amino acid sequences wherein no more than 1, 2, 3, 4 or 5 amino acids have been mutated by amino acid deletion, insertion or substitution in the CDR regions when compared with the CDR regions depicted in the sequence described above.

Further, variable heavy chain parental nucleotide sequences are shown in SEQ ID NOs: 127-140. Variable light chain parental nucleotide sequences are shown in SEQ ID NOs: 113-126. Full length light chain nucleotide sequences optimized for expression in a mammalian cell are shown in SEQ ID NOs: 161-165 and 171-175. Full length heavy chain nucleotide sequences optimized for expression in a mammalian cell are shown in SEQ ID NOs: 166-170 and 176-180. Other antibodies of the disclosure include amino acids or nucleic acids that have been mutated, yet have at least 60 or more (i.e. 80, 90, 95, 97, 99 or more) percent sequence identity to the sequences described above. In some embodiments, it includes mutant amino acid sequences wherein no more than 1, 2, 3, 4 or 5 amino acids have been mutated by amino acid deletion, insertion or substitution in the variable regions when compared with the variable regions depicted in the sequence described above.

Since each of these antibodies binds the same epitope and are progenies from the same parental antibody, the $V_H$, $V_L$, full length light chain, and full length heavy chain sequences (nucleotide sequences and amino acid sequences) can be "mixed and matched" to create other anti-ActRIIB binding molecules of the disclosure. ActRIIB binding of such "mixed and matched" antibodies can be tested using the binding assays described above and in the Examples (e.g. ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the disclosure provides an isolated recombinant anti-ActRIIB antibody or antigen binding region thereof having: a heavy chain variable region comprising an amino acid sequence selected from the group consisting of SEQ ID NOs: 99-112; and a light chain variable region comprising an amino acid sequence selected from the group consisting of SEQ ID NOs: 85-98.

In another aspect, the disclosure provides:
(i) an isolated recombinant anti-ActRIIB antibody having: a full length heavy chain comprising an amino acid sequence selected from the group consisting of SEQ ID NOs:99-112; and a full length light chain comprising an amino acid sequence selected from the group consisting of SEQ ID NOs:85-98, or
(ii) a functional fragment or functional protein comprising an antigen binding portion thereof.

In another aspect, the disclosure provides:
(i) an isolated recombinant anti-ActRIIB antibody having a full length heavy chain encoded by a nucleotide sequence that has been optimized for expression in the cell of a mammalian selected from the group consisting of SEQ ID NOs:127-140, and a full length light chain encoded by a nucleotide sequence that has been optimized for expression in the cell of a mammalian selected from the group consisting of SEQ ID NOs:113-126, or
(ii) a functional fragment or functional protein comprising an antigen binding portion thereof.

The amino acid sequences of the $V_H$ CDR1s of the antibodies are shown in SEQ ID NOs: 1-14.

The amino acid sequences of the $V_H$ CDR2s of the antibodies are shown in SEQ ID NOs: 15-28.

The amino acid sequences of the $V_H$ CDR3s of the antibodies are shown in SEQ ID NOs: 29-42.

The amino acid sequences of the $V_L$ CDR1s of the antibodies are shown in SEQ ID NOs: 43-56.

The amino acid sequences of the $V_L$ CDR2s of the antibodies are shown in SEQ ID NOs: 57-70.

The amino acid sequences of the $V_L$ CDR3s of the antibodies are shown in SEQ ID NOs: 71-84.

The CDR regions are delineated using the Kabat system (Kabat, E. A., et al., 1991 Sequences of Proteins of Immunological Interest, Fifth Edition, U.S. Department of Health and Human Services, NIH Publication No. 91-3242). An alternative method of determining CDR regions uses the method devised by Chothia (Chothia et al. 1989, Nature, 342:877-883). The Chothia definition is based on the location of the structural loop regions. However, due to changes in the numbering system used by Chothia, this system is now less commonly used. Other systems for defining CDRs exist.

Given that each of these antibodies can bind to ActRIIB and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e. CDRs from different antibodies can be mixed and matched, each antibody containing a $V_H$ CDR1, 2 and 3 and a $V_L$ CDR1, 2 and 3 create other anti-ActRIIB binding molecules of the disclosure. ActRIIB binding of such "mixed and matched" antibodies can be tested using the binding assays described above and in the Examples (e.g. ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present disclosure.

An isolated recombinant anti-ActRIIB antibody, or antigen binding region thereof has: a heavy chain variable region CDR1 comprising an amino acid sequence selected from the group consisting of SEQ ID NOs: 1-14; a heavy chain variable region CDR2 comprising an amino acid sequence selected from the group consisting of SEQ ID NOs: 15-28; a heavy chain variable region CDR3 comprising an amino acid sequence selected from the group consisting of SEQ ID NOs: 29-42; a light chain variable region CDR1 comprising an amino acid sequence selected from the group consisting of SEQ ID NOs: 43-56; a light chain variable region CDR2 comprising an amino acid sequence selected from the group consisting of SEQ ID NOs: 57-70; and a light chain variable region CDR3 comprising an amino acid sequence selected from the group consisting of SEQ ID NOs: 71-84.

In one embodiment, the antibody comprises: a heavy chain variable region CDR1 of SEQ ID NO: 1; a heavy chain variable region CDR2 of SEQ ID NO: 15; a heavy chain variable region CDR3 of SEQ ID NO: 29; a light chain variable region CDR1 of SEQ ID NO: 43; a light chain variable region CDR2 of SEQ ID NO: 57; and a light chain variable region CDR3 of SEQ ID NO: 71.

In one embodiment, the antibody comprises: a heavy chain variable region CDR1 of SEQ ID NO: 2 a heavy chain variable region CDR2 of SEQ ID NO: 16; a heavy chain variable region CDR3 of SEQ ID NO: 30; a light chain variable region CDR1 of SEQ ID NO: 44; a light chain variable region CDR2 of SEQ ID NO: 58; and a light chain variable region CDR3 of SEQ ID NO: 72.

In one embodiment, the antibody comprises: a heavy chain variable region CDR1 of SEQ ID NO: 3; a heavy chain variable region CDR2 of SEQ ID NO: 17; a heavy chain variable region CDR3 of SEQ ID NO: 31; a light chain variable region CDR1 of SEQ ID NO: 45; a light chain variable region CDR2 of SEQ ID NO: 59; and a light chain variable region CDR3 of SEQ ID NO: 73.

In one embodiment, the antibody comprises: a heavy chain variable region CDR1 of SEQ ID NO: 4; a heavy chain variable region CDR2 of SEQ ID NO: 18; a heavy chain variable region CDR3 of SEQ ID NO: 32; a light chain variable region CDR1 of SEQ ID NO: 46; a light chain variable region CDR2 of SEQ ID NO: 60; and a light chain variable region CDR3 of SEQ ID NO: 74.

In one embodiment, the antibody comprises: a heavy chain variable region CDR1 of SEQ ID NO: 5; a heavy chain variable region CDR2 of SEQ ID NO: 19; a heavy chain variable region CDR3 of SEQ ID NO: 33; a light chain variable region CDR1 of SEQ ID NO: 47; a light chain variable region CDR2 of SEQ ID NO: 61; and a light chain variable region CDR3 of SEQ ID NO: 75.

In one embodiment, the antibody comprises: a heavy chain variable region CDR1 of SEQ ID NO: 6; a heavy chain variable region CDR2 of SEQ ID NO: 20; a heavy chain variable region CDR3 of SEQ ID NO: 34; a light chain variable region CDR1 of SEQ ID NO: 48; a light chain variable region CDR2 of SEQ ID NO: 62; and a light chain variable region CDR3 of SEQ ID NO: 76.

In one embodiment, the antibody comprises: a heavy chain variable region CDR1 of SEQ ID NO: 7; a heavy chain variable region CDR2 of SEQ ID NO: 21; a heavy chain variable region CDR3 of SEQ ID NO: 35; a light chain variable region CDR1 of SEQ ID NO: 49; a light chain variable region CDR2 of SEQ ID NO: 63; and a light chain variable region CDR3 of SEQ ID NO: 77.

In one embodiment, the antibody comprises: a heavy chain variable region CDR1 of SEQ ID NO: 8; a heavy chain variable region CDR2 of SEQ ID NO: 22; a heavy chain variable region CDR3 of SEQ ID NO: 36; a light chain variable region CDR1 of SEQ ID NO: 50 a light chain variable region CDR2 of SEQ ID NO: 64; and a light chain variable region CDR3 of SEQ ID NO: 78.

In one embodiment, the antibody comprises: a heavy chain variable region CDR1 of SEQ ID NO: 9; a heavy chain variable region CDR2 of SEQ ID NO: 23; a heavy chain variable region CDR3 of SEQ ID NO: 37; a light chain variable region CDR1 of SEQ ID NO: 51; a light chain variable region CDR2 of SEQ ID NO: 65; and a light chain variable region CDR3 of SEQ ID NO: 79.

In one embodiment, the antibody comprises: a heavy chain variable region CDR1 of SEQ ID NO: 10; a heavy chain variable region CDR2 of SEQ ID NO: 24; a heavy chain variable region CDR3 of SEQ ID NO: 38; a light chain variable region CDR1 of SEQ ID NO: 52; a light chain variable region CDR2 of SEQ ID NO: 66; and a light chain variable region CDR3 of SEQ ID NO: 80.

In one embodiment, the antibody comprises: a heavy chain variable region CDR1 of SEQ ID NO: 11; a heavy chain variable region CDR2 of SEQ ID NO: 25; a heavy chain variable region CDR3 of SEQ ID NO: 39; a light chain variable region CDR1 of SEQ ID NO: 53; a light chain variable region CDR2 of SEQ ID NO: 67; and a light chain variable region CDR3 of SEQ ID NO: 81.

In one embodiment, the antibody comprises: a heavy chain variable region CDR1 of SEQ ID NO: 12; a heavy chain variable region CDR2 of SEQ ID NO: 26; a heavy chain variable region CDR3 of SEQ ID NO: 40; a light chain variable region CDR1 of SEQ ID NO: 54; a light chain variable region CDR2 of SEQ ID NO: 68; and a light chain variable region CDR3 of SEQ ID NO: 82.

In one embodiment, the antibody comprises: a heavy chain variable region CDR1 of SEQ ID NO: 13; a heavy chain variable region CDR2 of SEQ ID NO: 27; a heavy chain variable region CDR3 of SEQ ID NO: 41; a light chain variable region CDR1 of SEQ ID NO: 55; a light chain variable region CDR2 of SEQ ID NO: 69; and a light chain variable region CDR3 of SEQ ID NO: 83.

In one embodiment, the antibody comprises: a heavy chain variable region CDR1 of SEQ ID NO: 14; a heavy chain variable region CDR2 of SEQ ID NO: 28; a heavy chain variable region CDR3 of SEQ ID NO: 42; a light chain variable region CDR1 of SEQ ID NO: 56; a light chain variable region CDR2 of SEQ ID NO: 70; and a light chain variable region CDR3 of SEQ ID NO: 84.

In one embodiment, the disclosure provides an antibody comprising: (a) the variable heavy chain sequence of SEQ ID NO: 85 and variable light chain sequence of SEQ ID NO: 99; (b) the variable heavy chain sequence of SEQ ID NO: 86 and variable light chain sequence of SEQ ID NO: 100; (c) the variable heavy chain sequence of SEQ ID NO: 87 and variable light chain sequence of SEQ ID NO: 101; (d) the variable heavy chain sequence of SEQ ID NO: 88 and variable light chain sequence of SEQ ID NO: 102; (e) the variable heavy chain sequence of SEQ ID NO: 89 and variable light chain sequence of SEQ ID NO: 103; (f) the variable heavy chain sequence of SEQ ID NO: 90 and variable light chain sequence of SEQ ID NO: 104; (g) the variable heavy chain sequence of SEQ ID NO: 91 and variable light chain sequence of SEQ ID NO: 105; (h) the variable heavy chain sequence of SEQ ID NO: 92 and variable light chain sequence of SEQ ID NO: 106; (i) the variable heavy chain sequence of SEQ ID NO: 93 and variable light chain sequence of SEQ ID NO: 107; (j) the variable heavy chain sequence of SEQ ID NO: 94 and variable light chain sequence of SEQ ID NO: 108; (k) the variable heavy chain sequence of SEQ ID NO: 95 and variable light chain sequence of SEQ ID NO: 109; (l) the variable heavy chain sequence of SEQ ID NO: 96 and variable light chain sequence of SEQ ID NO: 110; (m) the variable heavy chain sequence of SEQ ID NO: 97 and variable light chain sequence of SEQ ID NO: 111; or (n) the variable heavy chain sequence of SEQ ID NO: 98 and variable light chain sequence of SEQ ID NO: 112.

In one embodiment, the disclosure provides an antibody comprising: (a) the heavy chain sequence of SEQ ID NO: 146 and light chain sequence of SEQ ID NO: 141; (b) the heavy chain sequence of SEQ ID NO: 147 and light chain sequence of SEQ ID NO: 142; (c) the heavy chain sequence of SEQ ID NO: 148 and light chain sequence of SEQ ID NO: 143; (d) the heavy chain sequence of SEQ ID NO: 149 and light chain sequence of SEQ ID NO: 144; (e) the heavy chain sequence of SEQ ID NO: 150 and light chain sequence of SEQ ID NO: 145; (f) the heavy chain sequence of SEQ ID NO: 156 and light chain sequence of SEQ ID NO: 151; (g) the heavy chain sequence of SEQ ID NO: 157 and light chain sequence of SEQ ID NO: 152; (h) the heavy chain sequence of SEQ ID NO: 158 and light chain sequence of SEQ ID NO: 153; (i) the heavy chain sequence of SEQ ID NO: 159 and light chain sequence of SEQ ID NO: 154; or (j) the heavy chain sequence of SEQ ID NO: 160 and light chain sequence of SEQ ID NO: 155.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e. greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g. murine germline sequences). In certain cases, a human antibody may be at least 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

In one embodiment the antibody of the disclosure is that encoded by pBW522 or pBW524 (deposited at DSMZ, Inhoffenstr. 7B, D-38124 Braunschweig, Germany on 18 Aug. 2009 under deposit numbers DSM22873 and DSM22874, respectively).

Homologous Antibodies

In yet another embodiment, an antibody of the disclosure has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-ActRIIB antibodies of the disclosure.

For example, the disclosure provides an isolated recombinant anti-ActRIIB antibody (or a functional fragment or functional protein comprising an antigen binding portion thereof) comprising a heavy chain variable region and a light chain variable region, wherein: the heavy chain variable region comprises an amino acid sequence that is at least 80%, or at least 90% (in various embodiments, at least 95, 97 or 99%) identical to an amino acid sequence selected from the group consisting of SEQ ID NOs: 99-112; the light chain variable region comprises an amino acid sequence that is at least 80%, or at least 90% (in various embodiments, at least 95, 97 or 99%) identical to an amino acid sequence selected from the group consisting of SEQ ID NOs: 85-98; and the antibody exhibits at least one of the following functional properties: (i) it inhibits myostatin binding in vitro or in vivo and/or (ii) decreases inhibition of muscle differentiation through the Smad-dependent pathway.

In a further example, the disclosure provides an isolated recombinant anti-ActRIIB antibody, (or a functional fragment or functional protein comprising an antigen binding portion thereof) comprising a full length heavy chain and a full length light chain, wherein: the full length heavy chain comprises an amino acid sequence that is at least 80%, or at least 90% (in various embodiments, at least 95, 97 or 99%) identical to an amino acid sequence selected from the group consisting of SEQ ID NOs: 146-150 and 156-160; the full length light chain comprises an amino acid sequence that is at least 80%, or at least 90°/(in various embodiments, at least 95, 97 or 99%) identical to an amino acid sequence selected from the group consisting of SEQ ID NOs: 141-145 and 151-155; and the antibody exhibits at least one of the following functional properties: (i) it inhibits myostatin binding in vitro or in vivo and/or (ii) decreases inhibition of muscle differentiation through the Smad-dependent pathway. In one embodiment, such an antibody binds to the ligand binding domain of ActRIIB.

In another example, the disclosure provides an isolated recombinant anti-ActRIIB antibody (or a functional fragment or functional protein comprising an antigen binding portion thereof), comprising a full length heavy chain and a full length light chain, wherein: the full length heavy chain is encoded by a nucleotide sequence that is at least 80%, or at least 90% (in various embodiments, at least 95, 97 or 99%) identical to a nucleotide sequence selected from the group consisting of SEQ ID NOs: 166-170 and 176-180; the full length light chain is encoded by a nucleotide sequence that is at least 80%, or at least 90% (in various embodiments, at least 95, 97 or 99%) identical to a nucleotide sequence selected from the group consisting of SEQ ID NOs: 161-165 and 171-175; and the antibody exhibits at least one of the following functional properties: (i) it inhibits myostatin binding in vitro or in vivo and/or (ii) decreases inhibition of muscle differentiation through the Smad-dependent pathway. In various embodiments such an antibody binds to the ligand binding domain of ActRIIB.

In various embodiments, the antibody may exhibit one or more, two or more, or three of the functional properties discussed above. The antibody can be, for example, a human antibody, a humanized antibody or a chimeric antibody. In various embodiments, the antibody is a fully human IgG1 antibody.

In other embodiments, the $V_H$ and/or $V_L$ amino acid sequences may be 80%, 90%, 95%, 96%, 97%, 98% or 99% identical to the sequences set forth above. In other embodiments, the $V_H$ and/or $V_L$ amino acid sequences may be identical except an amino acid substitution in no more than 1, 2, 3, 4 or 5 amino acid position. An antibody having $V_H$ and $V_L$ regions having high (i.e. 80% or greater) sequence identity to the $V_H$ and $V_L$ regions of SEQ ID NOs 99-112 and SEQ ID NOs: 85-98 respectively, can be obtained by mutagenesis (e.g. site-directed or PCR-mediated mutagenesis) of nucleic acid molecules SEQ ID NOs: 127-140 and 113-126 respectively, followed by testing of the encoded altered antibody for retained function (i.e. the functions set forth above) using the functional assays described herein.

In other embodiments, the full length heavy chain and/or full length light chain amino acid sequences may be 80%, 90%, 95%, 96%, 97%, 98% or 99% identical to the sequences set forth above. An antibody having a full length heavy chain and full length light chain having high (i.e. 80% or greater) identity to the full length heavy chains of any of SEQ ID NOs: 146-150 and 156-160 and full length light chains of any of SEQ ID NOs: 141-145 and 151-155 respectively, can be obtained by mutagenesis (e.g. site-directed or PCR-mediated mutagenesis) of nucleic acid molecules SEQ ID NOs: 166-170 and 176-180 and SEQ ID NOs: 161-165 and 171-175 respectively, followed by testing of the encoded altered antibody for retained function (i.e. the functions set forth above) using the functional assays described herein.

In other embodiments, the full length heavy chain and/or full length light chain nucleotide sequences may be 80%, 90%, 95%, 96%, 97%, 98% or 99% identical to the sequences set forth above.

In other embodiments, the variable regions of heavy chain and/or light chain nucleotide sequences may be 80%, 90%, 95%, 96%, 97%, 98% or 99% identical to the sequences set forth above.

As used herein, the percent identity between the two sequences is a function of the number of identical positions shared by the sequences (i.e. % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

Antibodies with Conservative Modifications

In certain embodiments, an antibody of the disclosure has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the anti-ActRIIB antibodies of the disclosure. Accordingly, the disclosure provides an isolated recombinant anti-ActRIIB antibody, or a functional fragment or functional protein comprising an antigen binding portion thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1-14, and conservative modifications thereof; the heavy chain variable region CDR2 amino acid sequences are selected from the group consisting of SEQ ID NOs: 15-28, and conservative modifications thereof; the heavy chain variable region CDR3 amino acid sequences are selected from the group consisting of SEQ ID NOs: 29-42, and conservative modifications thereof; the light chain variable regions CDR1 amino acid sequences are selected from the group consisting of SEQ ID NOs: 43-56, and conservative modifications thereof; the light chain variable regions CDR2 amino acid sequences are selected from the group consisting of SEQ ID NOs: 57-70, and conservative modifications thereof; the light chain variable regions of CDR3 amino acid sequences are selected from the group consisting of SEQ ID NOs: 71-84, and conservative modifications thereof. In various embodiments, the antibody exhibits at least one of the following functional properties: (i) it inhibits myostatin binding in vitro or in vivo and/or (ii) decreases inhibition of muscle differentiation through the Smad-dependent pathway.

In various embodiments, the antibody may exhibit one or both of the functional properties listed above. Such antibodies can be, for example, human antibodies, humanized antibodies or chimeric antibodies.

In other embodiments, an antibody of the disclosure optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-ActRIIB antibodies of the disclosure. Accordingly, the disclosure provides an isolated monoclonal anti-ActRIIB antibody optimized for expression in a mammalian cell consisting of a full length heavy chain and a full length light chain wherein: the full length heavy chain has amino acid sequences selected from the group of SEQ ID NOs: 146-150 and 156-160, and conservative modifications thereof; and the full length light chain has amino acid sequences selected from the group of SEQ ID NOs: 141-145 and 151-155, and conservative modifications thereof; and the antibody exhibits at least one of the following functional properties: (i) it inhibits myostatin binding in vitro or in vivo and/or (ii) decreases inhibition of muscle differentiation through the Smad-dependent pathway.

In various embodiments, the antibody may exhibit one or both of the functional properties listed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residues within the CDR regions of an antibody of the disclosure can be replaced with other amino acid residues from the same side chain family, and the altered antibody can be tested for retained function using the functional assays described herein.

Antibodies that Bind to the Same Epitope as Anti-ActRIIB Antibodies

In another embodiment, the disclosure provides antibodies that bind to the same epitope as the various specific anti-ActRIIB antibodies of the disclosure described herein. All the antibodies described in the Examples that are capable of blocking myostatin binding to ActRIIB bind the same epitope in ActRIIB with high affinity, said epitope being comprised between amino acids 19-134 of SEQ ID NO:181.

Additional antibodies can therefore be identified based on their ability to cross-compete (e.g. to competitively inhibit the binding of, in a statistically significant manner) with other antibodies of the disclosure in standard ActRIIB binding assays. The ability of a test antibody to inhibit the binding of antibodies of the present disclosure to human ActRIIB demonstrates that the test antibody can compete with that antibody for binding to human ActRIIB; such an antibody may, according to non-limiting theory, bind to the same or a related (e.g. a structurally similar or spatially proximal) epitope on human ActRIIB as the antibody with which it competes. In a certain embodiment, the antibody that binds to the same epitope on human ActRIIB as the antibodies of the present disclosure is a human recombinant antibody. Such human recombinant antibodies can be prepared and isolated as described in the Examples.

Thus, the disclosure provides an antibody that binds to an epitope recognised by an antibody having the variable heavy chain sequence recited in SEQ ID NO: 85, and the variable light chain sequence recited in SEQ ID NO: 99.

Thus, the disclosure provides an antibody that binds to an epitope recognised by an antibody having the variable heavy chain sequence recited in SEQ ID NO: 86, and the variable light chain sequence recited in SEQ ID NO: 100.

Thus, the disclosure provides an antibody that binds to an epitope recognised by an antibody having the variable heavy chain sequence recited in SEQ ID NO: 87, and the variable light chain sequence recited in SEQ ID NO: 101.

Thus, the disclosure provides an antibody that binds to an epitope recognised by an antibody having the variable heavy chain sequence recited in SEQ ID NO: 88, and the variable light chain sequence recited in SEQ ID NO: 102.

Thus, the disclosure provides an antibody that binds to an epitope recognised by an antibody having the variable heavy chain sequence recited in SEQ ID NO: 89, and the variable light chain sequence recited in SEQ ID NO: 103.

Thus, the disclosure provides an antibody that binds to an epitope recognised by an antibody having the variable heavy chain sequence recited in SEQ ID NO: 90, and the variable light chain sequence recited in SEQ ID NO: 104.

Thus, the disclosure provides an antibody that binds to an epitope recognised by an antibody having the variable heavy chain sequence recited in SEQ ID NO: 91, and the variable light chain sequence recited in SEQ ID NO: 105.

Thus, the disclosure provides an antibody that binds to an epitope recognised by an antibody having the variable heavy chain sequence recited in SEQ ID NO: 92, and the variable light chain sequence recited in SEQ ID NO: 106.

Thus, the disclosure provides an antibody that binds to an epitope recognised by an antibody having the variable heavy chain sequence recited in SEQ ID NO: 93, and the variable light chain sequence recited in SEQ ID NO: 107.

Thus, the disclosure provides an antibody that binds to an epitope recognised by an antibody having the variable heavy chain sequence recited in SEQ ID NO: 94, and the variable light chain sequence recited in SEQ ID NO: 108.

Thus, the disclosure provides an antibody that binds to an epitope recognised by an antibody having the variable heavy chain sequence recited in SEQ ID NO: 95, and the variable light chain sequence recited in SEQ ID NO: 109.

Thus, the disclosure provides an antibody that binds to an epitope recognised by an antibody having the variable heavy chain sequence recited in SEQ ID NO: 96, and the variable light chain sequence recited in SEQ ID NO: 110.

Thus, the disclosure provides an antibody that binds to an epitope recognised by an antibody having the variable heavy chain sequence recited in SEQ ID NO: 97, and the variable light chain sequence recited in SEQ ID NO: 111.

Thus, the disclosure provides an antibody that binds to an epitope recognised by an antibody having the variable heavy chain sequence recited in SEQ ID NO: 98, and the variable light chain sequence recited in SEQ ID NO: 112.

Following more detailed epitope mapping experiments, the binding regions of particular antibodies of the disclosure have been more clearly defined.

Thus, the disclosure provides an antibody that binds to an epitope comprising amino acids 78-83 of SEQ ID NO: 181 (WLDDFN—SEQ ID NO:188).

The disclosure also provides an antibody that binds to an epitope comprising amino acids 76-84 of SEQ ID NO: 181 (GCWLDDFNC—SEQ ID NO:186).

The disclosure also provides an antibody that binds to an epitope comprising amino acids 75-85 of SEQ ID NO: 181 (KGCWLDDFNCY—SEQ ID NO:190).

The disclosure also provides an antibody that binds to an epitope comprising amino acids 52-56 of SEQ ID NO: 181 (EQDKR—SEQ ID NO: 189).

The disclosure also provides an antibody that binds to an epitope comprising amino acids 49-63 of SEQ ID NO: 181 (CEGEQDKRLHCYASW—SEQ ID NO:187).

The disclosure also provides antibodies that bind to epitopes consisting of these sequences or epitopes comprising combinations of these epitope regions.

Thus, the disclosure also provides an antibody that binds to an epitope comprising or consisting of amino acids 78-83 of SEQ ID NO: 181 (WLDDFN) and amino acids 52-56 of SEQ ID NO: 181 (EQDKR).

Engineered and Modified Antibodies

An antibody of the disclosure further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e. $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g. Riechmann, L. et al., 1998 Nature 332:323-327; Jones, P. et al., 1986 Nature 321:522-525; Queen, C. et al., 1989 Proc. Natl. Acad. Sci. U.S.A. 86:10029-10033; U.S. Pat. No. 5,225,539 to Winter, and U.S. Pat. Nos. 5,530,101; 5,585,089; 5,693,762 and 6,180,370 to Queen et al.).

Accordingly, another embodiment of the disclosure pertains to an isolated monoclonal anti-ActRIIB antibody, or a functional fragment or functional protein comprising an antigen binding portion thereof, comprising a heavy chain variable region comprising CDR1 sequences having an amino acid sequence selected from the group consisting of SEQ ID NOs: 1-14; CDR2 sequences having an amino acid sequence selected from the group consisting of SEQ ID NOs: 15-28; CDR3 sequences having an amino acid sequence selected from the group consisting of SEQ ID NOs: 29-42, respectively; and a light chain variable region having CDR1 sequences having an amino acid sequence selected from the group consisting of SEQ ID NOs: 43-56; CDR2 sequences having an amino acid sequence selected from the group consisting of SEQ ID NOs: 57-70; and CDR3 sequences consisting of an amino acid sequence selected from the group consisting of SEQ ID NOs: 71-84, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., [supra]; Tomlinson, I. M., et al., 1992 J. fol. Biol. 227:776-798; and Cox, J. P. L. et al., 1994 Eur. J. Immunol. 24:827-836.

An example of framework sequences for use in the antibodies of the disclosure are those that are structurally similar to the framework sequences used by selected antibodies of the disclosure, e.g. consensus sequences and/or framework sequences used by monoclonal antibodies of the disclosure. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g. U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g. affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the disclosure provides isolated anti-ActRIIB monoclonal antibodies, or a functional fragment or functional protein comprising an antigen binding portion thereof, consisting of a heavy chain variable region having: a $V_H$ CDR1 region consisting of an amino acid sequence selected from the group having SEQ ID NOs: 1-14 or an amino acid sequence having one, two, three, four or five amino acid substitutions, deletions or additions as compared to SEQ ID NOs: 1-14; a $V_H$ CDR2 region having an amino acid sequence selected from the group consisting of SEQ ID NOs: 15-28, or an amino acid sequence having one, two, three, four or five amino acid substitutions, deletions or additions as compared to SEQ ID NOs: 15-28; a $V_H$ CDR3 region having an amino acid sequence selected from the group consisting of SEQ ID NOs: 29-42, or an amino acid sequence having one, two, three, four or five amino acid substitutions, deletions or additions as compared to SEQ ID NOs: 29-42; a $V_L$ CDR1 region having an amino acid sequence selected from the group consisting of SEQ ID NOs: 43-56, or an amino acid sequence having one, two, three, four or five amino acid substitutions, deletions or additions as compared to SEQ ID NOs: 43-56; a $V_L$ CDR2 region having an amino acid sequence selected from the group consisting of SEQ ID NOs: 52-70, or an amino acid sequence having one, two, three, four or five amino acid substitutions, deletions or additions as compared to SEQ ID NOs: 52-70; and a $V_L$ CDR3 region having an amino acid sequence selected from the group consisting of SEQ ID NOs: 71-84, or an amino acid sequence having one, two, three, four or five amino acid substitutions, deletions or additions as compared to SEQ ID NOs: 71-84.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to ActRIIB. Such frameworks or scaffolds include the 5 main idiotypes of human immunoglobulins, or fragments thereof (such as those disclosed elsewhere herein), and include immunoglobulins of other animal species, for example, having humanized aspects. Single heavy-chain antibodies such as those identified in camelids are of particular interest in this regard. Novel frameworks, scaffolds and fragments continue to be discovered and developed by those skilled in the art.

In one aspect, the disclosure pertains to generating non-immunoglobulin based antibodies using non-immunoglobulin scaffolds onto which CDRs of the disclosure can be grafted. Known or future non-immunoglobulin frameworks and scaffolds may be employed, as long as they comprise a binding region specific for the target protein of SEQ ID NO: 181 (in various embodiments, the ligand binding domain thereof as shown in SEQ ID NO: 182). Such compounds are known herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary family (*Camelus bactrianus* and *Camelus dromaderius*) including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals (see WO94/04678).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody" (see U.S. Pat. No. 5,759,808; Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520). Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e. the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e. camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue.

Nanobodies can further facilitate drug transport across the blood brain barrier (see US2004/0161738). These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present disclosure is a camelid antibody or nanobody having high affinity for ActRIIB. In certain embodiments herein, the camelid antibody or nanobody is naturally produced in the camelid animal, i.e. is produced by the camelid following immunization with ActRIIB or a peptide fragment thereof, using techniques described herein for other antibodies. Alternatively, the anti-ActRIIB camelid nanobody is engineered, i.e. produced by selection for example from a library of phage displaying appropriately mutagenized camelid nanobody proteins using panning procedures with ActRIIB as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the disclosure into nanobody or single domain antibody framework sequences, as described for example in WO94/04678.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based in various embodiments on fibronectin type III domain (e.g. the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the disclosure using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US2004/0175756; US2005/0053973; US2005/0048512; and US2006/0008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g. U.S. Pat. No. 5,831,012). Affibody® molecules mimic antibodies, they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris brassicae* has been used to develop anticalins by mutagenizing the set of four loops. One example of a patent application describing "anticalins" is WO1999/16873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO2001/004144 and examples of "ubiquitin-like" proteins are described in WO2004/106368.

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Framework or Fc Engineering

Engineered antibodies of the disclosure include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the disclosure.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in US2003/0153043.

In addition or alternative to modifications made within the framework or CDR regions, antibodies of the disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure may be chemically modified (e.g. one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g. increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In another embodiment, the antibody is modified to increase its biological half-life. Various approaches are possible. For example, one or more of the following mutations can be introduced: T252L, T254S, T256F, as described in U.S. Pat. No. 6,277,375. Alternatively, to increase the biological half life, the antibody can be altered within the CH1 or CL region to contain a salvage receptor binding epitope taken from two loops of a CH2 domain of an Fc region of an IgG, as described in U.S. Pat. No. 5,869,046 and U.S. Pat. No. 6,121,022.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. No. 5,624,821 and U.S. Pat. No. 5,648,260, both by Winter et al. In particular, residues 234 and 235 may be mutated. In particular, these mutations may be to alanine. Thus in one embodiment the antibody of the disclosure has a mutation in the Fc region at one or both of amino acids 234 and 235. In another embodiment, one or both of amino acids 234 and 235 may be substituted to alanine. Substitution of both amino acids 234 and 235 to alanine results in a reduced ADCC activity.

In another embodiment, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551.

In another embodiment, one or more amino acid residues are altered to thereby alter the ability of the antibody to fix complement. This approach is described further in WO94/29351.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in WO00/42072. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e. the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the disclosure are produced by recombinant expression in a cell line which exhibit hypofucosylation pattern, for example, a mammalian cell line with deficient expression of the FUT8 gene encoding fucosyltransferase. WO03/035835 describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). WO99/54342 describes cell lines engineered to express glycoprotein-modifying glycosyl transferases (e.g. beta(1,4)-N acetyl-glucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the disclosure can be produced in a yeast or a filamentous fungi engineered for mammalian-like glycosylation pattern, and capable of producing antibodies lacking fucose as glycosylation pattern (see for example EP1297172B1).

Another modification of the antibodies herein that is contemplated by the disclosure is pegylation. An antibody can be pegylated to, for example, increase the biological (e.g. serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure (see for example, EP0154316 and EP0401384).

Another modification of the antibodies that is contemplated by the disclosure is a conjugate or a protein fusion of at least the antigen-binding region of the antibody of the disclosure to serum protein, such as human serum albumin or a fragment thereof to increase half-life of the resulting molecule (see, for example, EP0322094).

Another possibility is a fusion of at least the antigen-binding region of the antibody of the disclosure to proteins capable of binding to serum proteins, such human serum albumin to increase half life of the resulting molecule (see, for example, EP0486525).

Methods of Engineering Altered Antibodies

As discussed above, the anti-ActRIIB antibodies having $V_H$ and $V_L$ sequences or full length heavy and light chain sequences shown herein can be used to create new anti-ActRIIB antibodies by modifying full length heavy chain and/or light chain sequences, $V_H$ and/or $V_L$ sequences, or the constant region(s) attached thereto. Thus, in another aspect of the disclosure, the structural features of an anti-ActRIIB antibody of the disclosure are used to create structurally related anti-ActRIIB antibodies that retain at least one functional property of the antibodies of the disclosure, such as binding to human ActRIIB but also inhibit one or more functional properties of ActRIIB (for example, the inhibition of Smad activation).

For example, one or more CDR regions of the antibodies of the present disclosure, or mutations thereof, can be combined recombinantly with known framework regions and/or other CDRs to create additional, recombinantly-engineered, anti-ActRIIB antibodies of the disclosure, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e. express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the disclosure provides a method for preparing an anti-ActRIIB antibody consisting of: a heavy chain variable region antibody sequence having a CDR1 sequence selected from the group consisting of SEQ ID NOs: 1-14, a CDR2 sequence selected from the group consisting of SEQ ID NOs: 15-28 and/or a CDR3 sequence selected from the group consisting of SEQ ID NOs: 29-42; and a light chain variable region antibody sequence having a CDR1 sequence selected from the group consisting of SEQ ID NOs: 43-56, a CDR2 sequence selected from the group consisting of SEQ ID NOs: 57-70 and/or a CDR3 sequence selected from the group consisting of SEQ ID NOs: 71-84; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the disclosure provides a method for preparing an anti-ActRIIB antibody optimized for expression in a mammalian cell consisting of: a full length heavy chain antibody sequence having a sequence selected from the group of SEQ ID NOs: 146-150 and 156-160; and a full length light chain antibody sequence having a sequence selected from the group of SEQ ID NOs: 141-145 and 151-155; altering at least one amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having fixed CDR3 sequences selected among the group consisting of SEQ ID NO: 29-42 and SEQ ID NO: 71-84 or minimal essential binding determinants as described in US2005/0255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the anti-ActRIIB antibodies described herein, which functional properties include, but are not limited to, specifically binding to human ActRIIB and inhibition of Smad activation.

The altered antibody may exhibit one or more, two or more, or three or more of the functional properties discussed above.

The functional properties of the altered antibodies can be assessed using standard assays available in the art and/or described herein, such as those set forth in the Examples (e.g. ELISAs).

In certain embodiments of the methods of engineering antibodies of the disclosure, mutations can be introduced randomly or selectively along all or part of an anti-ActRIIB antibody coding sequence and the resulting modified anti-ActRIIB antibodies can be screened for binding activity and/or other functional properties as described herein. Mutational methods have been described in the art. For example, WO02/092780 describes methods for creating and screening antibody mutations using saturation mutagenesis, synthetic ligation assembly, or a combination thereof. Alternatively, WO03/074679 describes methods of using computational screening methods to optimize physiochemical properties of antibodies.

Nucleic Acid Molecules Encoding Particular Antibodies

Another aspect of the disclosure pertains to nucleic acid molecules that encode the antibodies of the disclosure. Examples of full length light chain nucleotide sequences optimized for expression in a mammalian cell are shown in SEQ ID NOs: 161-165 and 171-175. Examples of full length heavy chain nucleotide sequences optimized for expression in a mammalian cell are shown in SEQ ID NOs: 166-170 and 176-180.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g. other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the disclosure can be, for example, DNA or RNA and may or may not contain intronic sequences. In an embodiment, the nucleic acid is a cDNA molecule. The nucleic acid may be present in a vector such as a phage display vector, or in a recombinant plasmid vector. The disclosure also provides the vectors referred to as pBW522 and pBW524 (deposited at DSMZ, Inhoffenstr. 7B, D-38124 Braunschweig, Germany on 18 Aug. 2009 under deposit numbers DSM22873 and DSM22874, respectively).

Nucleic acids of the disclosure can be obtained using standard molecular biology techniques. For antibodies expressed by hybridomas (e.g. hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g. using phage display techniques), nucleic acid encoding the antibody can be recovered from various phage clones that are members of the library.

Also included within the scope of the disclosure are variant nucleic acid sequences that comprise one or more deletions, additions or substitutions. In one embodiment, the disclosure comprises one or more of SEQ ID NOs: 113-140 or 161-180, which comprises a conservative nucleotide substitution. Due to the degeneracy of the genetic code, an amino acid may be encoded by more than one codon. Thus, it is possible to amend the nucleotide sequence, while the translated amino acid sequence remains the same.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g. Kabat, E. A., et al. [supra]) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g. Kabat, E. A., et al. [supra]) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g. encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g. Bird et al., 1988 Science 242:423-426; Huston et al., 1988 Proc. Natl. Acad. Sci. USA 85:5879-5883; McCafferty et al., 1990 Nature 348:552-554).

The nucleic acids of the disclosure may be used in gene delivery. That is, nucleic acid encoding the polypeptides (antibodies or functional proteins) of the disclosure may be directly delivered to a patient for translation in the patient.

The nucleic acid is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. Alternatively a retrovirus, such as a lentivirus may be used. For example, a nucleic acid molecule encoding a polypeptide of the disclosure may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

Generation of Particular Monoclonal Antibodies

Monoclonal antibodies (mAbs) can be produced by a variety of techniques, including conventional monoclonal antibody methodology e.g. the standard somatic cell hybridization technique of Kohler and Milstein (1975 Nature 256: 495). Many techniques for producing monoclonal antibody can be employed e.g. viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g. murine myeloma cells) and fusion procedures are also known.

Chimeric or humanized antibodies of the present disclosure can be prepared based on the sequence of a murine monoclonal antibody prepared as described above. DNA encoding the heavy and light chain immunoglobulins can be obtained from the murine hybridoma of interest and engineered to contain non-murine (e.g. human) immunoglobulin sequences using standard molecular biology techniques. For example, to create a chimeric antibody, the murine variable regions can be linked to human constant regions using methods known in the art (see e.g. U.S. Pat. No. 4,816,567). To create a humanized antibody, the murine CDR regions can be inserted into a human framework using methods known in the art (see e.g. U.S. Pat. Nos. 5,225,539; 5,530,101; 5,585,089; 5,693,762 and 6,180,370).

In a certain embodiment, the antibodies of the disclosure are human monoclonal antibodies. Such human monoclonal antibodies directed against ActRIIB can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy ($\mu$ and $\gamma$) and $\kappa$ light chain immunoglobulin sequences, together with targeted mutations that inactivate the endogenous $\mu$ and $\kappa$ chain loci (see e.g. Lonberg, et al., 1994 Nature 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal (Lonberg, N. et al., 1994 [supra]; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in theft entirety. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as WO92/103918, WO93/12227, WO94/25585, WO97/113852, WO98/24884; WO99/45962; and WO01/14424.

In another embodiment, human antibodies of the disclosure can be raised using a mouse that carries human immunoglobulin sequences on transgenes and transchromosomes such as a mouse that carries a human heavy chain trans gene and a human light chain transchromosome. Such mice, referred to herein as "KM mice", are described in detail in WO02/43478.

Still further, alternative transgenic animal systems expressing human immunoglobulin genes are available in the art and can be used to raise anti-ActRIIB antibodies of the disclosure. For example, an alternative transgenic system referred to as the Xenomouse (Abgenix, Inc.) can be used. Such mice are described in, e.g. U.S. Pat. Nos. 5,939,598; 6,075,181; 6,114,598; 6,150,584 and 6,162,963.

Moreover, alternative transchromosomic animal systems expressing human immunoglobulin genes are available in the art and can be used to raise anti-ActRIIB antibodies of the disclosure. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-ActRIIB antibodies of the disclosure.

Human recombinant antibodies of the disclosure can also be prepared using phage display methods for screening libraries of human immunoglobulin genes. Such phage display methods for isolating human antibodies are established in the art or described in the examples below. See for example: U.S. Pat. Nos. 5,223,409; 5,403,484; 5,571,698; 5,427,908; 5,580, 717; 5,969,108; 6,172,197; 5,885,793; 6,521,404; 6,544,731; 6,555,313; 6,582,915 and 6,593,081.

Human monoclonal antibodies of the disclosure can also be prepared using SCID mice into which human immune cells have been reconstituted such that a human antibody response can be generated upon immunization. Such mice are described in, for example, U.S. Pat. Nos. 5,476,996 and 5,698,767.

Generation of Hybridomas Producing Human Monoclonal Antibodies

To generate hybridomas producing human monoclonal antibodies of the disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the disclosure also can be produced in a host cell transfectoma using, for example, a combination of recombinant DNA techniques and gene transfection methods as is well known in the art (e.g. Morrison, S. (1985) Science 229:1202).

For example, to express the antibodies, or antibody fragments thereof, DNAs encoding partial or full-length light and heavy chains, can be obtained by standard molecular biology techniques (e.g. PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g. ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e. a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g. polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g. the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the disclosure may carry additional sequences, such as sequences that regulate replication of the vector in host cells (e.g. origins of replication) and selectable marker genes. The selectable marker gene facilitates selection of host cells into which the vector has been introduced (see, e.g. U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g. electroporation, calcium-phosphate precipitation, DEAE-dextran transfection and the like. It is theoretically possible to express the antibodies of the disclosure in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the disclosure include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g. as described in R. J. Kaufman and P. A. Sharp, 1982 Mol. Biol. 159:601-621), NSO myeloma cells, COS cells and SP2 cells. In one embodiment the host cells are CHO K1PD cells. In particular, for use with NSO myeloma cells, another expression system is the GS gene expression system shown in WO87/04462, WO89/01036 and EP 338,841. In one embodiment, mammalian host cells for expressing the recombinant antibodies of the disclosure include mammalian cell lines deficient for FUT8 gene expression, for example as described in U.S. Pat. No. 6,946,292B2. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present disclosure features an anti-ActRIIB antibody, or a fragment thereof, conjugated to a therapeutic moiety, such as a cytotoxin, a drug (e.g. an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g. kills) cells.

Cytotoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases, in various embodiments, expressed in tumor tissue such as cathepsins (e.g. cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G. 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the disclosure.

The antibody conjugates of the disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g. Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present disclosure features bispecific or multispecific molecules comprising an anti-ActRIIB antibody, or a fragment thereof, of the disclosure. An antibody of the disclosure, or antigen-binding regions thereof, can be derivatized or linked to another functional molecule, e.g. another peptide or protein (e.g. another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multi-specific molecules are also intended to be encompassed by the term "bispecific molecule" as used herein. To create a bispecific molecule of the disclosure, an antibody of the disclosure can be functionally linked (e.g. by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for ActRIIB and a second binding specificity for a second target epitope. For example, the second target epitope may be another epitope of ActRIIB different from the first target epitope.

Additionally, for the disclosure in which the bispecific molecule is multi-specific, the molecule can further include a third binding specificity, in addition to the first and second target epitope.

In one embodiment, the bispecific molecules of the disclosure comprise as a binding specificity at least one antibody, or an antibody fragment thereof, including, e.g. an Fab, Fab', F(ab)$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

Other antibodies which can be employed in the bispecific molecules of the disclosure are murine, chimeric and humanized monoclonal antibodies.

The bispecific molecules of the present disclosure can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g. Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (RIA), FACS analysis, bioassay (e.g. growth inhibition), or Western Blot assay. Each of these assays generally detects the presence of protein-antibody complexes of particular interest by employing a labeled reagent (e.g. an antibody) specific for the complex of interest.

Multivalent Antibodies

In another aspect, the present disclosure provides multivalent antibodies comprising at least two identical or different antigen-binding portions of the antibodies of the disclosure binding to ActRIIB. In one embodiment, the multivalent antibodies provides at least two, three or four antigen-binding portions of the antibodies. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the disclosure with an antibody that binds to the constant regions of the antibodies of the disclosure, for example the Fc or hinge region.

Pharmaceutical Compositions

In another aspect, the present disclosure provides a composition, e.g. a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g. two or more different) antibodies, or immunoconjugates or bispecific molecules of the disclosure. For example, a pharmaceutical composition of the disclosure can comprise a combination of antibodies that bind to different epitopes on the target antigen or that have complementary activities.

Pharmaceutical compositions of the disclosure also can be administered in combination therapy, i.e. combined with other agents. For example, the combination therapy can include an anti-ActRIIB antibody of the present disclosure combined with at least one other muscle mass/strength increasing agent, for example, IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g. by injection or infusion). Depending on the route of administration, the active compound, i.e. antibody, immunoconjuage, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" refers to a salt that retains the desired biological activity of the parent compound and does not impart any undesired toxicological effects (see e.g. Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of agents enumerated above, as required, followed by sterilization microfiltration. Generally, dispersions are prepared by incorporating the active compound into a sterile vehicle that contains a basic dispersion medium and the required other agents from those enumerated above. In the case of sterile powders for the preparation of sterile injectable solutions, the methods of preparation are vacuum drying and freeze-drying (lyophilization) that yield a powder of the active agent plus any additional desired agent from a previously sterile-filtered solution thereof.

The amount of active agent which can be combined with a carrier material to produce a single dosage form will vary depending upon the subject being treated, and the particular mode of administration. The amount of active agent which can be combined with a carrier material to produce a single dosage form will generally be that amount of the composition which produces a therapeutic effect. Generally, out of one hundred percent, this amount will range from about 0.01 percent to about ninety-nine percent of active agent, from about 0.1 percent to about 70 percent, or from about 1 percent to about 30 percent of active agent in combination with a pharmaceutically acceptable carrier.

Dosage regimens are adjusted to provide the optimum desired response (e.g. a therapeutic response). For example, a single bolus may be administered, several divided closes may be administered over time or the close may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the ranges of 1-10 mg/kg or 3-7 mg/kg. An example treatment regime entails administration once per week, once every two weeks, once every three weeks, once every four weeks, once a month, once every 3 months or once every three to 6 months. Alternatively, the antibody may be administered about once a year or once only. Such administration may be carried out intravenously or subcutaneously. Dosage regimens for an anti-ActRIIB antibody of the disclosure include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

The dosage should be one that causes an upregulation of muscle mass and/or strength. In various embodiments the effect is on skeletal muscle. In various embodiments, the dosage causes muscle hypertrophy with no more than a proportional increase in the size of internal organs (e.g. heart, lungs, liver, kidneys). Such a proportional increase may be compared by measuring either mass or volume.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months, every six months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml. For example, an ActRIIB antibody of the disclosure could be co-administered with an anti-myostatin antibody.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active agents in the pharmaceutical compositions of the present disclosure may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-ActRIIB antibody of the disclosure can result in a decrease in severity of disease symptoms, an increase in frequency and duration of disease symptom-free periods, or a prevention of impairment or disability clue to the disease affliction i.e. an increase in muscle mass and/or strength.

A composition of the present disclosure can be administered by one or more routes of administration using one or more of a variety of methods known in the art. As will be appreciated by the skilled artisan, the route and/or mode of administration will vary depending upon the desired results.

Routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In one embodiment the antibody is administered intravenously. In another embodiment the antibody is administered subcutaneously.

Alternatively, an antibody of the disclosure can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the disclosure can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well known implants and modules useful in the present disclosure include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art and include those made by MicroCHIPS™ (Bedford, Mass.).

In certain embodiments, the human monoclonal antibodies of the disclosure can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhance targeted drug delivery (see, e.g. V. V. Ranade, 1989 J. Clin Pharmacol. 29:685). Example targeting moieties include folate or biotin (see, e.g. U.S. Pat. No. 5,416,016); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

Uses and Methods of the Antibodies

The antibodies of the present disclosure have in vitro and in vivo diagnostic and therapeutic utilities. For example, these molecules can be administered to cells in culture, e.g. in vitro or ex vivo, or in a subject, e.g. in vivo, to treat, prevent or diagnose a variety of disorders. Thus the antibodies may be used in both the treatment of disease, prophylaxis and for delaying the onset of disease symptoms. The term "subject" as used herein is intended to include human and non-human animals. Non-human animals include all vertebrates, e.g. mammals and non-mammals, such as non-human primates, sheep, dogs, cats, cows, horses, chickens, amphibians, and reptiles.

The disclosure provides a method of treating a patient suffering from a pathological disorder (such as a muscle wasting disease or disorder) comprising administering a therapeutically effective amount of an anti-ActRIIB antibody.

The disclosure also provides an anti-ActRIIB antibody for use in therapy.

The disclosure also provides use of an anti-ActRIIB antibody in the manufacture of a medicament for the treatment of a pathological disorder.

The methods are particularly suitable for treating, preventing, ameliorating or diagnosing pathological disorders.

As used herein, a "pathological disorder" includes, but is not limited to, musculoskeletal diseases or disorders, such as muscle atrophy. There are many causes of muscle atrophy, including as a result of treatment with a glucocorticoid such as cortisol, dexamethasone, betamethasone, prednisone, methylprednisolone, or prednisolone. The muscle atrophy can also be a result of denervation due to nerve trauma or a result of degenerative, metabolic, or inflammatory neuropathy (e.g., Guillian-Barré syndrome, peripheral neuropathy, or exposure to environmental toxins or drugs).

In addition, the muscle atrophy can be a result of myopathy, such as myotonia; a congenital myopathy, including nemalene myopathy, multi/minicore myopathy and myotubular (centronuclear) myopathy; mitochondrial myopathy; familial periodic paralysis; inflammatory myopathy; metabolic myopathy, such as caused by a glycogen or lipid storage disease; dermatomyositisis; polymyositis; inclusion body myositis; myositis ossificans; rhabdomyolysis and myoglobinurias.

The myopathy may be caused by a muscular dystrophy syndrome, such as Duchenne, Becker, myotonic, fascioscapulohumeral, Emery-Dreifuss, oculopharyngeal, scapulohumeral, limb girdle, Fukuyama, a congenital muscular dystrophy, or hereditary distal myopathy. The musculoskeletal disease can also be osteoporosis, a bone fracture, short stature, or dwarfism.

In addition, the muscle atrophy can be a result of an adult motor neuron disease, infantile spinal muscular atrophy, amyotrophic lateral sclerosis, juvenile spinal muscular atrophy, autoimmune motor neuropathy with multifocal conductor block, paralysis due to stroke or spinal cord injury, skeletal immobilization due to trauma, prolonged bed rest, voluntary inactivity, involuntary inactivity, metabolic stress or nutritional insufficiency, cancer, AIDS, fasting, a thyroid gland disorder, diabetes, benign congenital hypotonia, central core disease, burn injury, chronic obstructive pulmonary disease, liver diseases (examples such as fibrosis, cirrhosis), sepsis, renal failure, congestive heart failure, ageing, space travel or time spent in a zero gravity environment.

Examples of age-related conditions that may be treated include, sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, frailty, memory loss, wrinkles, impaired kidney function, and age-related hearing loss; metabolic disorders, including Type II Diabetes, Metabolic Syndrome, hyperglycemia, and obesity. Of course, patients may simultaneously suffer from one or more of these conditions, for example, sarcopenia and pulmonary emphysema, or sarcopenia and impaired kidney function.

Other conditions that are considered to be "pathological disorders" as recited herein include acute and/or chronic renal disease or failure, liver fibrosis or cirrhosis, cancer such as breast cancer, Parkinson's Disease; conditions associated with neuronal death, such as ALS, brain atrophy, or dementia and anemia.

Further conditions include cachexia, cachexia associated with a rheumatoid arthritis and cachexia associated with cancer.

To date, very few reliable or effective therapies have been developed to treat these disorders.

Based on reported evidence of a role of activins binding to ActRIIB amongst other receptors (Werner and Alzheimer, Cytokine Growth Factors Rev 2006, 17(3):157-171), in contributing to liver, kidney and pulmonary fibrosis and of a role for myostatin, activins, or ActRIIB in cancers (Tsuchida et al, Endo J, 2008) the "pathological disorders" recited herein include liver, kidney and pulmonary fibrosis and cancers exemplified by but not restricted to rhabdomyosarcomas, bone-loss inducing cancers, hepatocellular carcinomas, gastrointestinal cancers.

The prevention may be complete, e.g., the total absence of an age-related condition or metabolic disorder. The prevention may also be partial, such that the likelihood of the occurrence of the age-related condition or metabolic disorder in a subject is less likely to occur than had the subject not received an antibody of the present disclosure.

An age-related condition as referred to herein may begin at the age of 50 years or older (i.e. 60, 70, 80 or older).

In one embodiment, a patient may be pre-treated with an anti-ActRIIB antibody prior to an anticipated period of enforced rest/inactivity. Such a period may occur when a patient is admitted to hospital, for example for surgery to the hip or leg. The inactivity may be localised, such as by casting of a broken limb or joint, or by administration of a paralytic agent.

In one embodiment, the patient being treated has a fracture to a limb (i.e. leg or arm) or joint (i.e. knee or hip). Thus, in one embodiment, the patient being treated has a fracture to one or more of the humerus, radius, ulnar, a carpal, a metacarpal, the clavical, scapular, femur, os coxae, patella, tibia, fibula, talus, calcaneus, a tarsal, a metatarsal, the ischium or the ileum. In another embodiment, the patient being treated has undergone, or will undergo surgery on one or more of the following joints: knee, hip, ankle, shoulder, elbow. Such surgery includes hip replacement and knee replacement.

Atrophy due to immobilisation may occur quickly, but normally occurs slowly. Therefore, in one embodiment, the patient, joint or limb has been immobilised, or will be immobilised, for 2 weeks or longer (i.e. 3 weeks, 4 weeks, 6 weeks, 8 weeks or longer). In one embodiment, the patient, joint or limb has been immobilised, or will be immobilised, for 1-8 weeks, 2-6 weeks or 3-5 weeks.

In a further embodiment, the patient may be one who has not responded to previous bone anabolic treatments. For example, the patient may not have responded to treatment with IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin. A simple way of measuring a patient's response to treatment may be timing how long it takes for a patient to climb a known height of stairs and comparing the results both before and after treatment.

The antibodies of the disclosure may be administered as the sole active agent or in conjunction with, e.g. as an adjuvant to or in combination to, other drugs e.g. IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a S ARM, GH agonists/mimetics or follistatin. For example, the antibodies of the disclosure may be used in combination with an IGF-1 mimetic as disclosed in WO2007/146689.

In accordance with the foregoing the present disclosure provides in a yet further aspect:

A method as defined above comprising co-administration, e.g. concomitantly or in sequence, of a therapeutically effective amount of an ActRIIB antagonist, e.g. an antibody of the disclosure, and at least one second drug substance, said second drug substance being IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin.

The disclosure further provides a therapeutic combination, e.g. a kit, comprising of a therapeutically effective amount of a) an ActRIIB antagonist, e.g. an antibody of the disclosure, and b) at least one second substance selected from an IGF-1, IGF-2 or variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics or follistatin, e.g. as indicated above. The kit may further comprise instructions for its administration.

Where the antibodies of the disclosure are administered in conjunction with another active agent, dosages of the co-administered combination compound will of course vary depending on the type of co-drug employed, on the specific drug employed, on the condition being treated and so forth.

In another embodiment, the antibodies of the disclosure are administered only to a patient population which is selected among patients suffering from muscle atrophy. In another embodiment, the antibodies of the disclosure are administered to patient populations suffering from skeletal muscle atrophy. In another embodiment, the antibodies of the disclosure are administered only to a patient population which is selected among a group of patients which respond to anti-ActRIIB treatment. Biomarkers that identify patients that have an increased likelihood of responding to anti-ActRIIB treatment may be any of the following without being limited to these: high levels of serum myostatin, GDF-11 or activins compared to a control patient.

In one embodiment, the antibodies of the disclosure can be used to detect levels of ActRIIB, or levels of cells that contain ActRIIB. This can be achieved, for example, by contacting a sample (such as an in vitro sample) and a control sample with the anti-ActRIIB antibody under conditions that allow for the formation of a complex between the antibody and ActRIIB Any complexes formed between the antibody and ActRIIB are detected and compared in the sample and the control. For example, standard detection methods, well known in the art, such as ELISA and flow cytometric assays, can be performed using the compositions of the disclosure.

Accordingly, in one aspect, the disclosure further provides methods for detecting the presence of ActRIIB (e.g. human ActRIIB) in a sample, or measuring the amount of ActRIIB, comprising contacting the sample, and a control sample, with an antibody of the disclosure, or an antigen binding region thereof, which specifically binds to ActRIIB, under conditions that allow for formation of a complex between the antibody or portion thereof and ActRIIB. The formation of a complex is then detected, wherein a difference in complex formation between the sample compared to the control sample is indicative of the presence of ActRIIB in the sample.

Also within the scope of the disclosure are kits consisting of the compositions (e.g. antibodies, human antibodies and bispecific molecules) of the disclosure and instructions for use. The kit can further contain at least one additional reagent, or one or more additional antibodies of the disclosure (e.g. an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will response to an anti-ActRIIB antibody treatment, as defined above. Such kits may comprise an antibody of the disclosure in lyophilised form, a diluent and instructions for use.

The disclosure having been fully described, it is further illustrated by the following examples and claims, which are illustrative and are not meant to be further limiting.

General

The term "comprising" means "including" as well as "consisting" e.g. a composition "comprising" X may consist exclusively of X or may include something additional e.g. X+Y.

The term "about" in relation to a numerical value x means, for example, x±10%.

MODES FOR CARRYING OUT PARTICULAR METHODS

Figure 1:
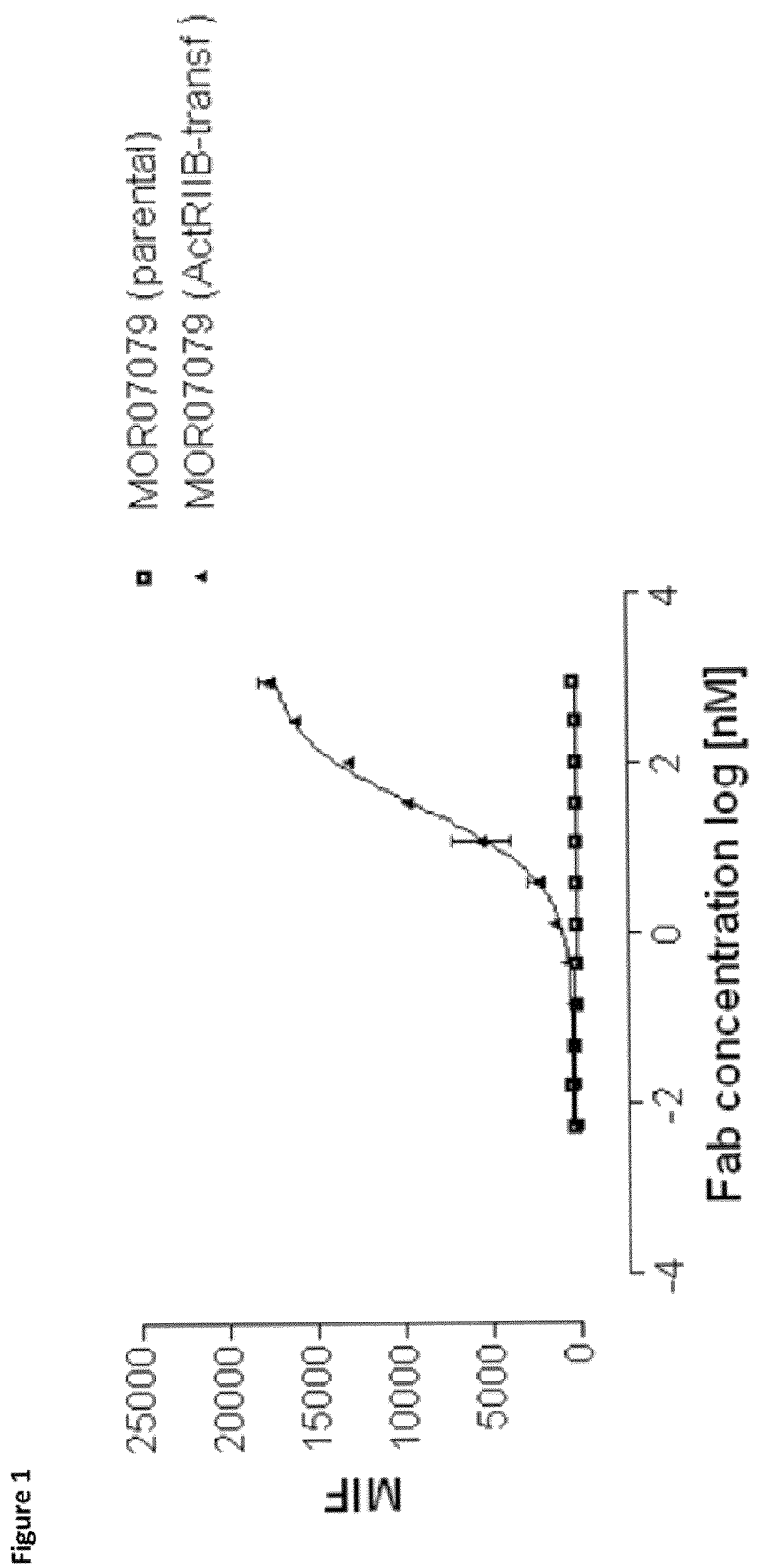
FIG. 1 shows EC50 determination of MOR07079 by FACS titration on parental and ActRIIB transfected HEK293T/17 cell lines.

Functional Assays
Reporter Gene Assay (RGA)
Cultivation of HEK293T/17 Cell Lines Parental HEK293T/17 cells are maintained in DMEM containing 10% FBS, 2 mM L-glutamine, penicillin (50 IE/ml), and streptomycin (50 μg/ml). Cells are grown in an incubator at 37° C. and 5% $CO_2$ and subcultured every 3-4 days. Cells are detached using Accutase™ and then transferred into a new flask containing fresh medium.

HEK293T/17 cells stably transfected with CAGA-12 luc are cultured as described above for parental HEK293T/17 cells but cell growth medium is supplemented with 4 mM L-glutamine and 3 μg/ml blasticidin in addition to FBS, penicillin and streptomycin.

Myostatin-Induced Luciferase Reporter Gene Assay

To determine the capacity of anti-ActRIIB antibodies to inhibit myostatin-induced signaling, a reporter gene assay using the stable reporter cell line HEK293T/17 CAGA-12 luc is performed. The CAGA-12 luciferase reporter construct carries the luciferase gene downstream of a minimal promoter and multiple CAGA boxes which are specific for phosphorylated Smad-2 and Smad-3. Addition of purified myostatin (but also of GDF-11, activin or TGFβ) induces Smad phosphorylation and thus binding to the CAGA-12 reporter and leads to luciferase gene expression.

At 90% confluency of HEK293T/17 CAGA-12 luc cells, cells are detached as described and diluted in culture medium to a concentration of $2.5 \times 10^5$ cells/ml. Subsequently, 100 μl cells per well are seeded into flat-bottomed 96-well plates and incubated at 37° C. and 5% $CO_2$ overnight.

The next day, the antibodies (Fab or IgG) and the recombinant human ActRIIB/Fc, which served as the positive control, are diluted in PBS to the desired concentrations. 20 μl of the antibody solutions are added to the seeded wells of the previous day and the cells cultivated for 1 hr to allow binding of the antibodies. Finally, 50 ng/ml myostatin is added to the wells and the cells further cultivated over night.

The next morning, 120 μl Bright-Glo luciferase reagent (Promega) is added to each well. After 2 min incubation time, the luminescence is read in a luminometer. The half maximal inhibitory concentration (IC50 values) is calculated after full titration of the respective antibodies.

Specificity ELISAs

The specificity of anti-ActRIIB Fab antibodies to human ActRIIB and crossreactivity to human ActRIIA and mouse ActRIIB is evaluated in an ELISA setting. Additionally, binding to related receptors (counter-targets: human TGF-βRII/Fc (R&D systems), mouse TGF-βRI (ALK-5)/Fc (R&D systems), human Activin RIB (ALK-4)/Fc (R&D systems)) is determined. For this 5 µg/ml (if not stated otherwise) of the recombinant proteins diluted in PBS are added to a black 96-well flat-bottom MaxiSorp™ plate and incubated over night at 4° C. for coating.

The next morning, the plates are washed with TBST and blocked with MTBST. After washing the plates several times, 5 µg/ml anti-ActRIIB Fab are added and incubated for 2.5 hrs. Subsequently antigen bound Fabs are detected by incubation with alkaline phosphatase conjugated goat-anti-human IgG Fab-specific, followed by addition of AttoPhos fluorescence substrate. Fluorescence emission at 535 nm is recorded with excitation at 430 nm in a TECAN Spectrafluor plate reader.

ActRIIB/Fc-Myostatin Binding Interaction ELISA

To assess whether the inhibitory Fabs act via blocking the myostatin binding site of human ActRIIB a hActRIIB/Fc-myostatin interaction ELISA is performed. For this, recombinant myostatin is diluted to 5 µg/ml in PBS and coated onto a black 96-well flat-bottom Maxisorp plate. The next morning the wells are blocked with MTBST. Meanwhile 50 µg/ml anti-ActRIIB Fabs are pre-incubated with 10 µg/ml ActRIIB/Fc in TBST for 1.5 hrs at room temperature and finally added to the coated and blocked wells (1.5 hr at room temperature). After washing with TBST buffer, detection of bound ActRIIB/Fc is performed using an unlabelled mouse anti-human Ig Fc-specific antibody and a POD-labelled sheep anti-mouse IgG detection antibody. After washing the wells several times with TBST buffer Quanta Blu™ Fluorogenic Peroxidase substrate is added. The fluorescence is read in a GENiosPro™ reader (excitation 320 nm, emission 430 nm).

Binding to Cells

Cells

Stable human ActRIIA- and human ActRIIB-transfected HEK293T/17 cells, generated using HEK293T/17 cells (ATCC) transfected with linearized pEGFP (Clontech)-ActRIIB(ECD) or -ActRIIA(ECD) and pPGK-puro (AddGene) using FuGENE6 (Roche), are maintained in DMEM containing 10% FBS, 2 mM L-glutamine, penicillin (50 IE/ml), streptomycin (50 µg/ml) and puromycin (2 µg/ml). Cells are grown in an incubator at 37° C. and 5% $CO_2$ and subcultured every 3-4 clays. Cells are detached using Accutase™ and then transferred into a new flask containing fresh media.

Human skeletal muscle cells (huSkMC) (Cambrex) are harvested at a confluency of about 70-90%. For those cells, culture medium, growth medium (GM) consisting of skeletal muscle basal medium (skBM; Lonza) supplemented with 20% FCS (Amimed), is aspirated, and the cells are washed with HEPES-BSS and incubated with Trypsin/EDTA. After the cells are detached, trypsin is neutralized with trypsin neutralizing solution. Cells are centrifuged at 220×g for 5 min and the pellet is resuspended in Skeletal Muscle Growth Media. Cells are then used for experiments or seeded for subculturing at a cell density of ~3500 cell/cm². Cells are grown in an incubator at 37° C. and 5% $CO_2$ and subcultured every 5-6 days.

FACS Titration on hActRIIB- and hActRIIA-Expressing Cells

The half maximal effective concentration (EC50) of the anti-ActRIIB antibodies is determined via binding to cellular hActRIIA and hActRIIB by FACS.

For this, serial dilutions of anti-ActRIIB Fab or IgG are incubated with $1 \times 10^4$ hActRIIA-transfected, hActRIIB-transfected or parental HEK293T/17 cells per well for 1 h at 4° C. After several washing steps cell-bound Fabs or IgGs are detected with phycoerythrin-conjugated goat anti-human IgG (H+L) secondary antibody. After one hour incubation at 4° C., the cells are washed again and resuspended in FACS buffer and fluorescence intensity of the cells is determined in a FACSArray™ instrument.

Binding to Primary Human Skeletal Muscle Cells

Anti-ActRIIB Fab or IgG as well as isotype control Fab or IgG (10 µg) are incubated with $10^5$ huSkMC in FACS buffer (PBS, 2% FCS, 1 mM EDTA) per tube for 1 h at 4° C. After washing steps, cell-bound Fabs or IgGs are detected with phycoerythrin-conjugated goat anti-human IgG (H+L) secondary antibody which had been diluted 1:200 in FACS buffer. After one hour incubation at 4° C. on a shaker, the cells are washed again and resuspended in FACS buffer and fluorescence intensity of the cells determined in the FACSCaliber™ instrument.

Affinity Determination

Affinity Determination of Selected Anti-Human ActRIIB Fabs Using Surface Plasmon Resonance (Biacore)

For direct antigen immobilisation standard EDC-NHS amine coupling chemistry is used. CM5 chips (Biacore, Sweden) are coated with approximately 6000 RU human- or mouse-ActRIIB/Fc, or approximately 1500 RU human-ActRIIA/Fc (according to the activity of the antigens) in 10 mM acetate buffer, pH 4.5. For the reference flow cell, a respective amount of HSA is used. Regeneration is done with 5 µl. 10 mM Glycine/HCl buffer pH1.5.

Alternatively, the antigens are not immobilized directly, but captured on a CM5 chip, which is modified with an anti-human-Fc antibody (Fc capture kit, GE Healthcare/Biacore). On the reference flow cell, capture antibody is immobilized, but no antigen captured. Regeneration is achieved using 2 injections of 5 µL 3M $MgCl_2$.

Kinetic measurements are done in Dulbecco's PBS at a flow rate of 20 µl/min using a serial dilution row of Fab samples. The Fab concentrations ranged from 15.6 to 500 nM. Injection time for each concentration is 1 min. The dissociation time is set to at least 2 min (or more, according to determined affinity). A blank injection of running buffer is used for double referencing. All sensorgrams are fitted globally using BIA evaluation software 3.2 (Biacore, Sweden).

CK Assay

Differentiation is initiated 24 hours after seeding by changing cells from GM to serum-free differentiation medium consisting of skeletal muscle basal medium (skBM). Cells are differentiated for 3 days in the absence and presence of myostatin (R&D systems) or other TGF-b proteins and tested antibodies at given concentrations. Cells are washed with PBS and then lysed with Reporter lysis buffer (Promega) and stored till measurement at −80° C. CK activity is measured using the CK (IFCC) reagent (Thermo Electron). The CK reagent is prepared according to the manufacturers instructions. Cell lysates are adjusted to room temperature, CK reagent is added and absorbance is immediately read at 340 nm for 20 min, reading interval 1 min. CK standard curves are freshly prepared using CK from rabbit muscle (Roche Diagnostics). Protein content is determined using BCA kit.

Animal Models

Nine-week-old female CB17/ICR-Prkdc$^{scid}$/Cr1 mice (n=10 per group, Charles River, Germany) are randomized with body weight and then treated intraperitoneally with anti-human ActRIIB antibodies (MOR8159, MOR8213) or IgG control antibody at a dose of 10 mg/kg (Study 1; comparison study), or with MOR8213 at doses of 25, 5, or 1 mg/kg (Study 2; dose response study) on day 0, 3, 7, 14, 21, 28 and 35 (once weekly with day 3). Body weights are determined two times per week. Six weeks (42 days) after administration, mice are euthanized with $CO_2$. Tibialis, gastrocnemius with plantaris, quadriceps and pectoralis are collected and weighed.

Treatment Protocol
Control antibody: anti-chicken lysozyme-hIgG,
Concentration: 2 mg/mL (study 1), 5 mg/mL (study 2), application volume: 5 mL/kg
Vehicle: 50 mM Citrate, 140 mM NaCl or PBS
anti-human ActRIIB antibodies: anti-ActRIIB-MOR8159 and MOR8213, hIgG,
Concentration: 2 mg/mL (study 1), 5 mg/mL (study 2), 1 mg/mL (study 2), 0.2 mg/mL (study 2), application volume: 5 mL/kg
Vehicle: 50 mM Citrate, 140 mM NaCl
Treatment Groups:
Study 1; Comparison of MOR08159 and MOR08213
1 IgG control, i.p. (anti-chicken lysozyme-IgG), 10 mg/kg
2 anti-ActRIIB-MOR8159, i.p., 10 mg/kg
3 anti-ActRIIB-MOR8213, i.p, 10 mg/kg
Study 2; dose response of MOR08213
1 IgG control, i.p. (anti-chicken lysozyme IgG), 25 mg/kg
2 anti-ActRIIB-MOR8213, i.p., 25 mg/kg
3 anti-ActRIIB-MOR8213, i.p., 5 mg/kg
4 anti-ActRIIB-MOR8213, i.p., 1 mg/kg
Maintenance Conditions Animals are housed in groups of four to five animals at 25° C. with a 12:12 h light-dark cycle. They are fed a standard laboratory diet containing 18.2% protein and 3.0% fat with energy of 15.8 MJ/kg (NAFAG 3890, Kliba). Food and water are provided ad libitum. Animal experimentation is carried out according to the regulations effective in the Canton of Basel-City, Switzerland.

Methods
Statistical Analysis

Results are expressed as mean+/−SEM. Statistical analysis is carried out using Dunnett's multiple comparison test following one-way analysis of variance. Treatment (anti-ActRIIB antibodies MOR8159 and MOR8213 are tested for difference to control (control antibody) and differences are considered to be significant when the probability value is <0.05: *:P<0.05, **: P<0.01, NS: no significance versus IgG control. Statistical analyses are performed by GraphPad Prism version 5.0 (GraphPad Software, Inc). Body weight are calculated by subtracting body weight at day 0, and muscle weight is normalized by body weight at day 0 (initial body weight).

Pannings, Antibody Identification and Characterization

Therapeutic antibodies against human ActRIIB protein are generated by selection of clones having high binding affinities, using as the source of antibody variant proteins a commercially available phage display library, the MorphoSys HuCAL GOLD® library.

HuCAL GOLD® library is a Fab library (Knappik et al., 2000) in which all six CDRs are diversified by appropriate methods, and which employs the CysDisplay™ technology for linking the Fab to the phage surface (WO01/05950).

HuCAL GOLD® phagemid library (Rothe et al., 2008) is used to select specific Fab antibody fragments.

Selection by Panning of ActRIIB-Specific Antibodies from the Library

For the selection of antibodies recognizing human ActRIIB several panning strategies are applied.

In summary, HuCAL GOLD® antibody-phages are divided into several pools comprising different VH master genes.

These pools are individually subjected to differential cell pannings whereby selection rounds on transiently human ActRIIB transfected cells alternated with selection rounds on recombinant human ActRIIB/Fc protein.

i. Whole Cell Panning

For the pannings, phage particles diluted in PBS are mixed with an equal volume of PBS/BSA and blocked. In parallel, also in pre-blocked tubes, $1 \times 10^7$ of the respective hActRIIB expressing cells per phage pool are resuspended in PBS/3% FCS/0.04% $NaN_3$ and blocked for one hour at 4° C. on a shaker. The blocked cells are spun down, resuspended in the pre-blocked phage particles and incubated for three hours. In the meantime, $1 \times 10^7$ hActRIIB knock-down cells per phage pool are prepared.

The phage-cell complexes are washed in PBS/BSA, followed by washing in PBS. Elution of phage particles from the hActRIIB expressing cells is performed by acidic elution with glycine buffer, pH 2.2. After centrifugation, the eluate is neutralized by adding unbuffered Tris.

After infection and subsequent centrifugation, the bacterial pellets are resuspended in 2×YT medium, plated onto LB/CAM/Glc agar plates and incubated overnight at 37° C. The next morning, the colonies are scraped off the plates and the phages are rescued and amplified.

ii. Solid Phase Panning

For solid phase panning recombinant human ActRIIB/Fc is coated onto a MaxiSorp™ plate at 4° C. over night. After washing with PBS the coated wells are blocked with 5% MPBST.

Prior to the selections, HuCAL GOLD® phage are pre-adsorbed in blocking buffer. The blocked phage are added to the coated antigen and incubated for 2 hrs at room temperature. Unspecific phage are washed off with PBST and PBS. Bound phage are eluted by addition of 20 mM DTT. The eluates are used for infection of an E. coli TG-1 culture. After infection, the bacteria are plated onto LB/CAM/Glc agar plates and incubated overnight at 37° C. The next morning, the colonies are scraped off the plates and the phage are rescued and amplified.

The most successful panning approach proved to be differential cell/protein pannings with first panning round on ActRIIB transfected HEK293T/17 cells followed by selection round on recombinant human ActRIIB/Fc and again on transfected cells.

Selected Fabs are analyzed for binding to parental or rhActRIIB transfected HEK293 cells.

MOR07079Fab binds in various embodiments to ActRIIB-transfected cells with an EC50 of 20 nM (FIG. 1). In a myostatin binding inhibition ELISA, MOR07079 Fab showed inhibitory activity and blocked rhActRIIB/Fc binding to myostatin. Strong myostatin binding inhibition in ELISA is reflected by myostatin inhibition in the reporter gene assay using HEK293-CAGA12 for MOR07079. Using the specificity ELISA, MOR07079 is shown to bind specifically to human and murine ActRIIB and not to the unrelated TGF-βRII, ALK4 and ALK5 receptors. MOR7079 is also shown to bind in various embodiments to ActRIIB compared to ActRIIA.

Production of HuCAL® Immunoglobulins i. Conversion of Fabs into the IgG Format

In order to express full length immunoglobulin (Ig), the variable domain fragments of heavy (VH) and light chains (VL) are subcloned from the pMORPH®X9_FH Fab expression vectors into the pMORPH®2_h_Ig vector series for human IgG2. Selected clones are also converted into the silent IgG1LALA format in which leucines at positions 234 and 235 are mutated to alanines to abrogate FcRγ binding and attenuate effector functions.

Appropriate restriction enzymes (Knappik et al., 2000) are used for subcloning of the VH and VL domain fragments into pMORPH®2_h_IgG2, pMORPH®2_h_IgG1LALA, pMORPH®2_h_Igκ, and pMORPH®2_h_Igλ2.

All DNA preparations are subjected to sequence analysis before transfection into HKB11 cells.

ii. Transient Expression and Purification of Human IgG

Eukaryotic HKB11 cells are transfected with IgG heavy and light chain expression vector DNA. Cell culture supernatant is harvested at 3 or 7 days post transfection and subjected to standard protein A affinity chromatography. If not otherwise stated, buffer exchange is performed to 1× Dulbecco's PBS (pH 7.2) and samples are sterile filtered (0.2 μm).

CDR-L3 and CDR-H2 Maturation Libraries

To increase affinity and biological activity of selected antibody fragments, CDR-L3 and CDR-H2 regions are optimized in parallel by cassette mutagenesis using trinucleotide directed mutagenesis (Virnekas et al., 1994, Nucleic Acids Res. 22:5600-5607), whereby the framework regions are kept constant (Nagy et al., 2002, Nature Medicine, 8:801-807). Prior to cloning of the maturation libraries, all parental Fab fragments are transferred from the expression vector pMORPH° X9 into the CysDisplay™ maturation vector pMORPH® 25 via the XbaI/EcoRI restriction sites. This vector provides the phage protein pIII fused N-terminally to a cysteine residue as well as a C-terminal cysteine fused to the Fd antibody chain and thus allows disulfide-linked display of the respective Fab fragments on the phage surface.

For generation of the CDR-H2 libraries the CDR-H2 region of each parental Fab is excised and replaced by the highly diversified CDR-H2 maturation cassette.

In parallel, the CDR-L3 region of the parental clones is replaced by a diversified CDR-L3 maturation cassette.

The sizes of the maturation libraries ranged from $4 \times 10^5$ to $1 \times 10^8$ clones. The vector background is below 1% in all cases. The quality control by sequencing of single clones revealed a high quality of each library.

For each CDR-L3 and CDR-H2 maturation library, antibody-displaying phage are prepared and phage titers determined by spot titration.

Panning Strategies for Affinity Maturation

The antibody-displaying phages from the following maturation libraries are subjected to separate pannings and screenings:

Lead 1: MOR07079 (L-CDR3 maturation)

Lead 1: MOR07079 (H-CDR2 maturation)

Maturation pannings using the respective antibodies are performed on biotinylated hActRIIB/Fc and on huSkMC.

Either $2 \times 10^{10}$ or $1 \times 10^{11}$ phages per subcode, rescued from the newly generated maturation libraries are used for the first selection rounds.

Several differential pannings are performed whereby selection rounds on recombinant biotinylated hActRIIB/Fc alternated with a selection round on huSkMC.

For the first and third round of the solution panning biotinylated recombinant hActRIIB/Fc is captured onto Streptavidin-coated Dynabeads. The following protocol is applied: for each phage pool, Streptavidin beads are washed with PBS and resuspended in blocking buffer. Phage particles diluted in PBS are mixed blocking buffer containing 0.1% Tween20 and kept on a rotating wheel. Preclearing of phage particles for removal of Streptavidin- or bead-binding phages is performed twice: Per phage pool blocked Streptavidin beads are added to the blocked phage particles and incubated on a rotating wheel. After separation of the beads via a magnetic device the phage supernatant is transferred to a fresh, pre-blocked reaction tube and pre-adsorption is repeated.

After the blocking procedure, the biotinylated hActRIIB/Fc antigen is added to the precleared and blocked phage particles and incubated on a rotating wheel. The phage-antigen complexes are captured using blocked streptavidin beads, added to the phage panning pools and incubated further. Phage particles bound to the streptavidin beads are collected. Beads are then washed with PBST and PBS. Elution of phage particles from the streptavidin beads is performed by addition of 20 mM DTT. The eluate is collected and used for infection of an E. coli TG-1 culture grown to an $OD_{600nm}$ of 0.6-0.8.

After infection and subsequent centrifugation, the bacterial pellets are resuspended in 2×YT medium, plated onto LB/CAM/Glc agar plates and incubated overnight at 37° C. The next morning, the colonies are scraped off the plates and the phages are rescued and amplified mainly as described (Krebs et al., 2001) with the exception that helper phage infected cells are grown at 22° C. over night in medium containing 0.25 mM IPTG. The third rounds of the solution pannings on biotinylated hActRIIB/Fc are performed according to the protocol of the first round except for decreasing amounts of antigen used and increased stringency of the washing conditions.

For the second round of panning (on huSkMC expressing endogenous hActRIIB), phage particles diluted in PBS are mixed with an equal volume of PBS/BSA and blocked. In parallel, for each subcode $9 \times 10^5$ huSkMC are blocked with PBS/FCS/0.02% $NaN_3$ at 4° C. The blocked cells are spun down, resuspended together with the pre-blocked phage particles and incubated further.

The phage-cell complexes are washed with PBS/BSA, followed by washing in PBS. Cells are centrifuged at 410×g for 2 min at 4° C. Acidic elution of phage particles from the hActRIIB expressing huSkMC is performed by a 10 min incubation step with glycine buffer, pH 2.2. After centrifugation, the eluate is neutralized by adding unbuffered Tris. The phage containing supernatant is used for infection of an E. coli TG-1 culture grown to an $OD_{600nm}$ of 0.6-0.8.

After infection and subsequent centrifugation, the bacterial pellets are resuspended in 2×YT medium, plated onto LB/CAM/Glc agar plates and incubated overnight at 37° C. The next morning, the colonies are scraped off the plates and the phages are rescued and amplified mainly as described (Krebs et al., 2001) with the exception that helper phage infected cells are grown at 22° C. over night in medium containing 0.25 mM IPTG.

The most successful panning approach which resulted in very potent binders proved to be the differential panning with the first and third round performed on biotinylated ActRIIB/Fc and the second round on huSkMC.

After sequencing, Fabs are selected for expression and purification, and the most promising further characterized.

Figure 2:
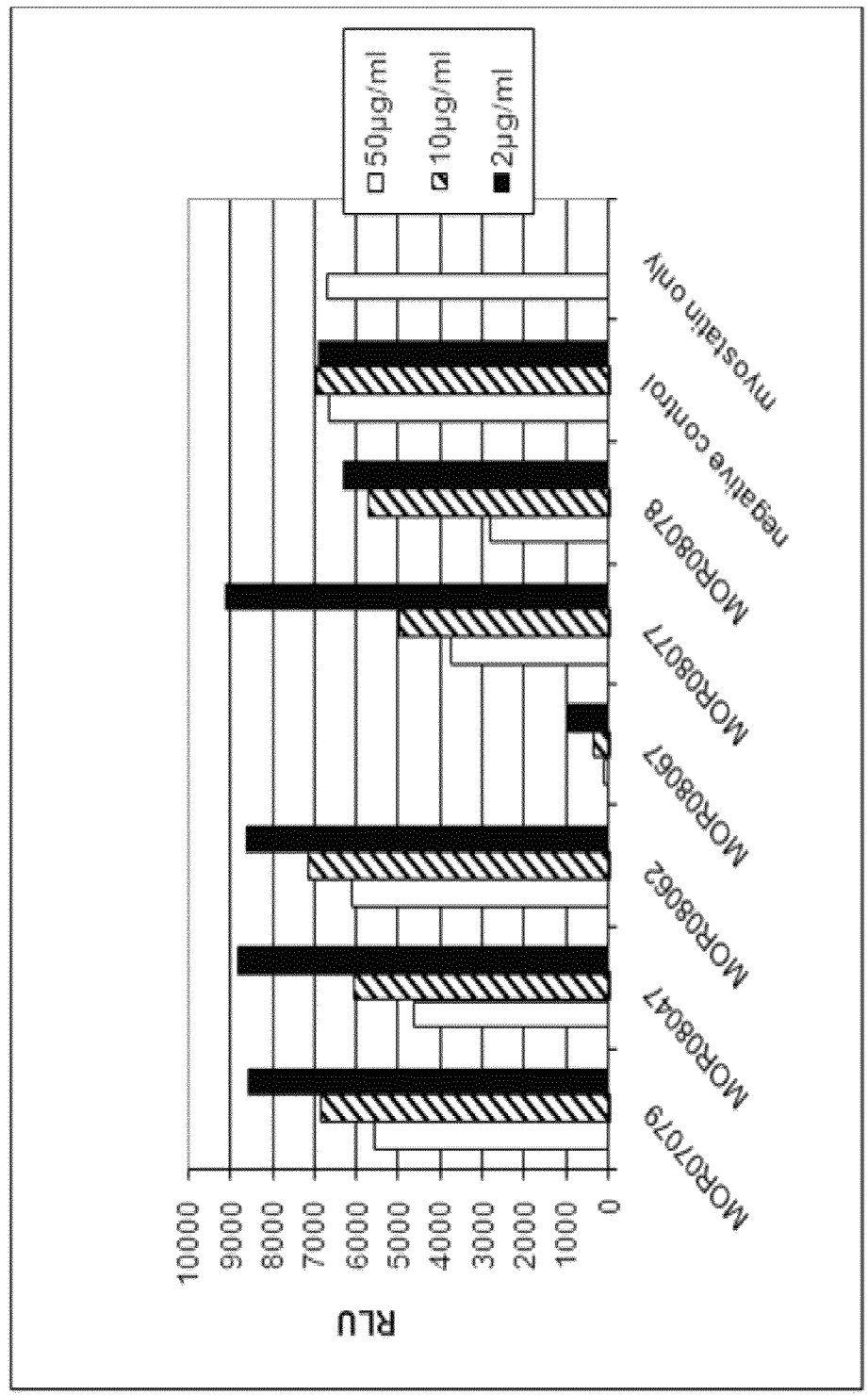
FIG. 2 shows inhibition of myostatin-induced luciferase expression in a reporter gene assay by multiples of anti-ActRIIB Fabs at 2, 10 and 50 μg/ml.

Most anti-ActRIIB antibodies showed binding to hActRIIB-transfected HEK293T/17 cells with EC50 values in the single up to low double digit nanomolar range. Several Fabs could displace myostatin from ActRIIB/Fc in a myostatin binding inhibition ELISA, but amongst those only MOR08067 displayed full inhibition of myostatin-induced activity in the reporter gene assay (FIG. 2).

Summarized affinities of the most promising Fab to human and mouse ActRIIB/Fc are listed in the table below (Table 1).

TABLE 1

Affinity data of anti-ActRIIB Fab-FH to ActRIIB antigens

| | KD determination (Biacore) | |
|---|---|---|
| Fab | human ActRIIB-Fc KD [nM] | mouse ActRIIB-Fc KD [nM] |
| MOR07079 | 51 | 62 |
| MOR08047 | 23 | 22 |
| MOR08062 | 15 | 17 |
| MOR08067 | <0.1 | <0.1 |
| MOR08077 | 11 | 13 |
| MOR08078 | 9 | 10 |

The Fab clone MOR08067 exhibited good inhibition in the myostatin induced RGA as well as binding to rhActRIIB transfected HEK293 cells. Affinity determination by Biacore revealed KD values to human and mouse ActRIIB/Fc below 100 pM. MOR08067 and other candidates are selected for further optimization by a cross cloning approach, while MOR08067, containing a potential N-linked glycosylation site is also subjected to a deglycosylation approach.

Optimization of Antibodies Derived from First Affinity Maturation a) Deglycosylation of MOR08067

According to sequence analysis this antibody contained a potential N-linked glycosylation site within the CDR-H2 of the heavy chain. This site is removed to yield MOR08156 and MOR08159. The characterization of these MOR08067-derivatives is described below.

b) Cross Cloning of Optimized Fabs

For a further functional improvement and removal of potential N-linked glycosylation sites in CDR-H2s and/or CDR-L3s, the independently optimized CDR-H2 and CDR-L3 regions from single affinity matured Fabs resulting from the first affinity maturation are combined while keeping each family separate. Descendants of MOR07079 entered cross cloning. Roughly 200 bacterial lysates are tested in FACS affinity ranking on HEK293T/17/ActRIIB and the most promising Fab clones, MOR08144 and MOR08213 are expressed, and purified.

c) Characterization of Optimized Antibodies

In the following sections, the deglycosylated progenies of MOR08067 (MOR08156, MOR08159) and the two cross clones derived from MOR08067 (MOR08144 and MOR08213) are described in detail.

Figure 3:
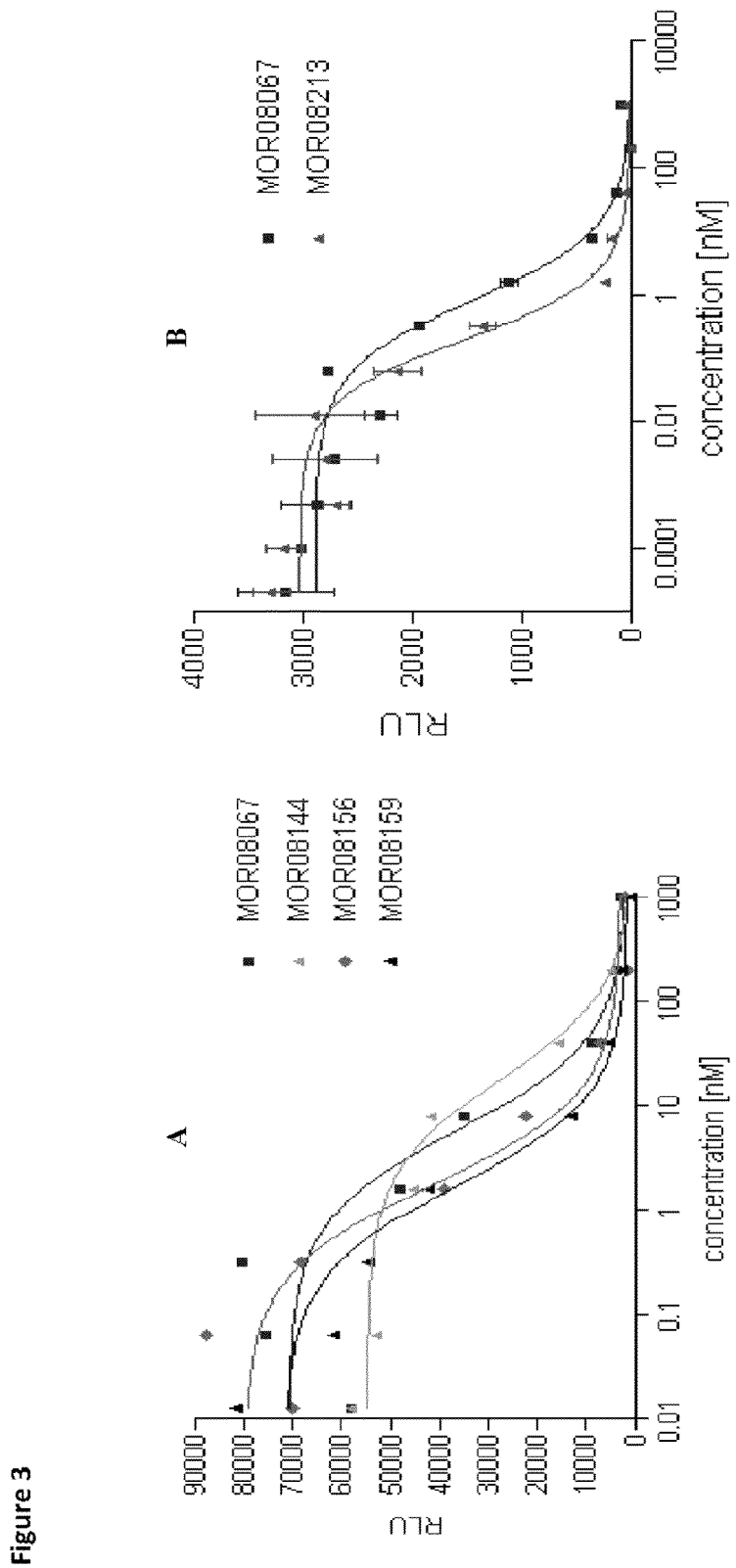
FIGS. 3 A and B show IC50 determination of Fabs [MOR08067, MOR08144, MO08156 and MOR08159 in FIG. 3A; and MOR08067 and MOR08213 in FIG. 3B] in myostatin-induced luciferase reporter gene assay.

The ability of optimized Fabs to inhibit myostatin signaling in the reporter gene assay is determined, with all binders being able to induce >95% inhibition at the highest concentration (FIG. 3).

In affinity determination experiments using Biacore, MOR08159 and MOR08213 are identified as highly potent binders to both human and mouse ActRIIB (Table 2). It became obvious the increased affinity of matured and optimized Fabs reflected increased potency in the myostatin-induced reporter gene assay.

TABLE 2

Affinity data of anti-ActRIIB Fabs to ActRIIB antigens

| | KD determination (Biacore) | |
|---|---|---|
| Fab | human ActRIIB-Fc KD [pM] | mouse ActRIIB-Fc KD [pM] |
| MOR08159 | 3.8 | 3.1 |
| MOR08213 | 13.2 | 13.5 |

IgG2 Conversion of Affinity Matured Fabs (1st Maturation)

The most promising Fabs derived from the first affinity maturation are selected for IgG2 conversion.

IgG2 expression is performed by transient transfection of HKB11 cells and the full length immunoglobulins are purified from the cell culture supernatants.

Upon conversion to IgG, all candidates retained their ability to dose-dependently inhibit myostatin-induced activity in the reporter gene assay (Table 3).

TABLE 3

IC50 determination of anti-ActRIIB IgGs in myostatin-induced luciferase reporter gene assay

| IgG | IC50 [nM] | % inhibition |
|---|---|---|
| MOR08067 | 2.57 | 86.5 |
| MOR08144 | 0.5 | 94.9 |
| MOR08156 | 0.19 | 97.4 |
| MOR08159 | 0.32 | 99 |
| MOR08213 | 0.32 | 98.6 |

Figure 4:
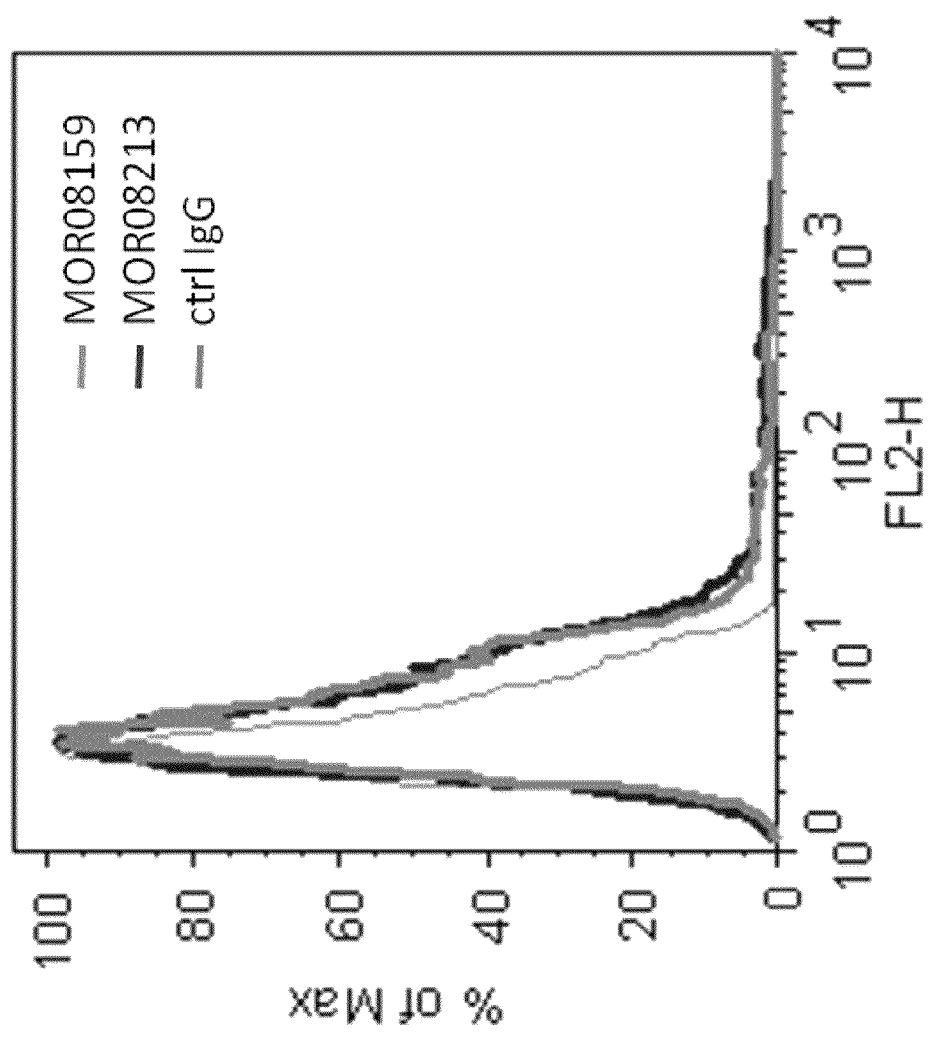
FIG. 4 shows antibody binding to primary human skeletal muscle cells.

MOR08159 and MOR08213 are tested for their ability to bind to human primary muscle myoblasts by FACS, and specific binding to those cells is reported, in line with low expression of ActRIIB on those cells (FIG. 4).

Figure 5:
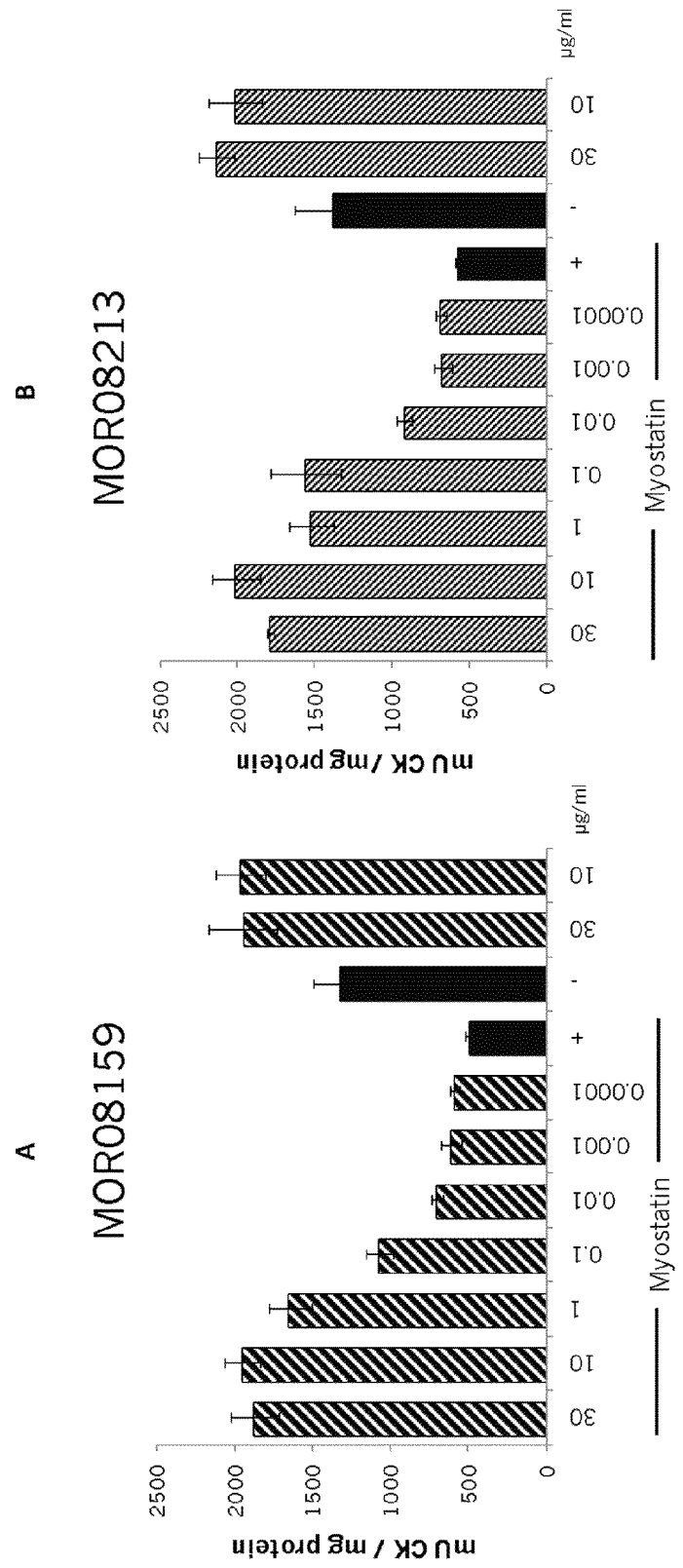
FIGS. 5 A and B show IC50 determination of IgG [MOR08159 in FIG. 5A; and MOR08213 in FIG. 5B] in myostatin-induced inhibition of skeletal muscle differentiation assay.

MOR08159 and MOR08213 displayed ability to fully reverse the myostatin-induced inhibition of primary skeletal myoblasts differentiation (FIG. 5). Those antibodies also increased differentiation above basal level in the absence of exogenous myostatin, due to their ability to neutralize endogenously produced ActRIIB ligands.

Second Affinity Maturation

Selection of Candidates for Second Affinity Maturation to further improve the efficacy.

i. Construction of the CDR-L3 and CDR-H2 Maturation Libraries

To increase both affinity and biological activity of the selected antibody fragments (e.g. MOR08067), CDR-L1 and CDR-H2 regions are optimized by cassette mutagenesis using trinucleotide directed mutagenesis (Virnekas et al. [supra]), whereby the framework regions are kept constant (Nagy et al. [supra]). Prior to cloning of the maturation libraries, all parental Fab fragments are transferred from the expression vector pMORPH® X9 into the CysDisplay™ maturation vector pMORPH® 25 via the XbaI/EcoRI restriction sites.

The sizes of all maturation libraries yielded always a minimum of $1 \times 10^7$ independent clones. The vector background is below 1% in all cases. Quality control by sequencing of single clones revealed a high quality of each library.

For each CDR-L1 and CDR-H2 maturation library, antibody-displaying phages are prepared and phage titers are determined by spot titration.

ii. Panning Strategies, Affinity Ranking and Screening for Improved Antibodies

Differential pannings for the second round of affinity maturation included parental HEK293T/17 cells and huSkMC expressing human ActRIIB endogenously at low levels. Additionally, recombinant biotinylated hActRIIB/Fc antigen is included in all panning strategies.

For ranking of the anti-ActRIIB Fabs, approximately 2700 bacterial lysates (~88 clones for each panning subcode) are affinity ranked on recombinant biotinylated hActRIIB/Fc antigen and membrane vesicle preparations of hActRIIB-transfected HEK293T/17 cells in an MSD-based method. Hits with high affinity ranking factor are sequenced.

In addition, randomly selected clones which did not show up as hits are evaluated in FACS affinity ranking. For this, bacterial lysates are screened using parental HEK293T/17 and/or hActRIIB-transfected HEK293T/17 cells. Cell-bound Fabs are detected with phycoerythrin-conjugated goat anti-human IgG (H+L) secondary antibody. The quantification of Fab expression in the lysates is performed in parallel.

All panning strategies yielded anti-ActRIIB specific antibodies. MOR08067 progenies could be identified after sequence analysis. All binders are matured in CDR-H2.

IgG2 Conversion and Characterization of IgG2 ($2^{nd}$ Maturation)

Again, the most promising Fabs derived from the second affinity maturation are selected for IgG2 conversion. IgG2 expression is performed by transient transfection of HKB11 cells and the full length immunoglobulins are purified from the cell culture supernatants.

All IgGs tested are able to fully reverse the myostatin-induced inhibition of primary skeletal myoblasts differentiation (table 4).

TABLE 4

IC50 determination of anti-ActRIIB IgGs in myostatin-induced inhibition of skeletal muscle differentiation assay

| IgG | CK assay IC50 [nM] |
| --- | --- |
| MOR08159 | 1.89 |
| MOR08213 | 1.7 |
| MOR08806 | 0.52 |
| MOR08807 | 5.02 |
| MOR09032 | 1.02 |
| MOR09058 | 2.3 |

We evaluated the ability of the anti-ActRIIB Ab to neutralize binding of myostatin as well as other TGFβ family ligands to ActRIIB on primary human skeletal myoblasts. In the myoblast differentiation assay, we assessed the various ligands potential to inhibit differentiation in the absence or presence of either MOR08159 or MOR08213.

Myostatin and GDF-11 are able to inhibit human myoblasts differentiation with similar efficiencies and to similar extents. In the presence of a single concentration of MOR08159 or MOR08213, myostatin and GDF-11 dose responses are shifted in a parallel manner. Activin A is also able to inhibit differentiation, however in the presence of MOR08159 or MOR08213, we observed a non parallel shift accompanied by a change in Emax and potency. BMP-2 response is unaffected by the presence of MOR08159 or MOR08213, suggesting that it does not occur via ActRIIB binding.

Characterization of Anti ActRIIB Antibodies in In Vivo Murine Studies.

Figure 6:
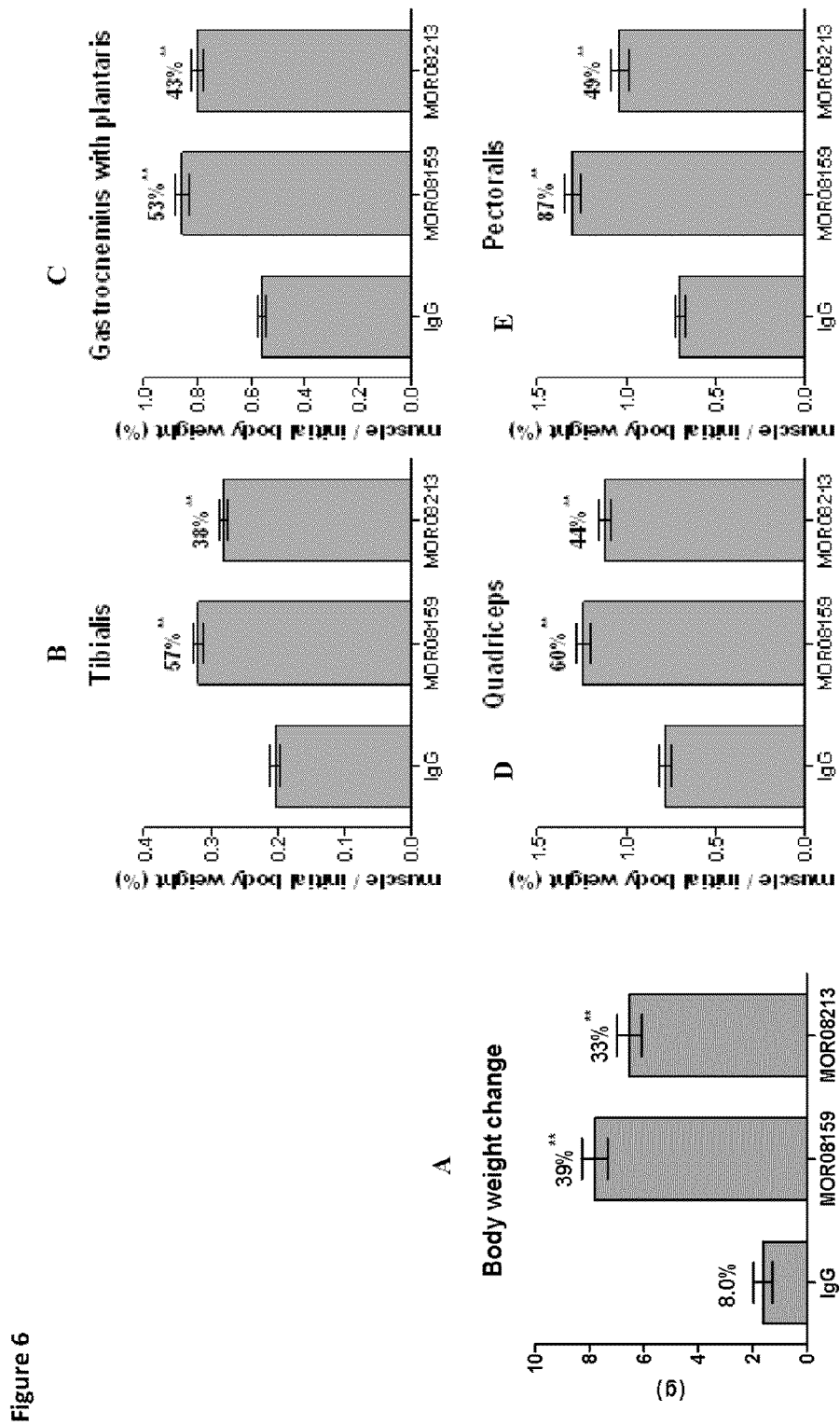
FIG. 6 shows mouse study: in vivo efficacy study in naive animals—6 weeks treatment with MOR08159 or MOR08213 at 10 mg/kg increased body and muscle weight. Changes are shown for (A) body weight (B) Tibialis, (C) Gastrocnemius with plantaris, (D) Quadriceps and (E) Pectoralis.

The ability of anti-ActRIIB antibodies to induce muscle hypertrophy is evaluated in SCID mice administered MOR08159 or MOR08213, 10 mg/kg i.p. weekly for 6 weeks (FIG. 6).

Both antibodies are able to induce a profound hypertrophy of all examined muscles at study end. Significant increase in overall bodyweight of anti-ActRIIB antibody treated mice is detected as early as after 1 week of treatment.

Figure 7:
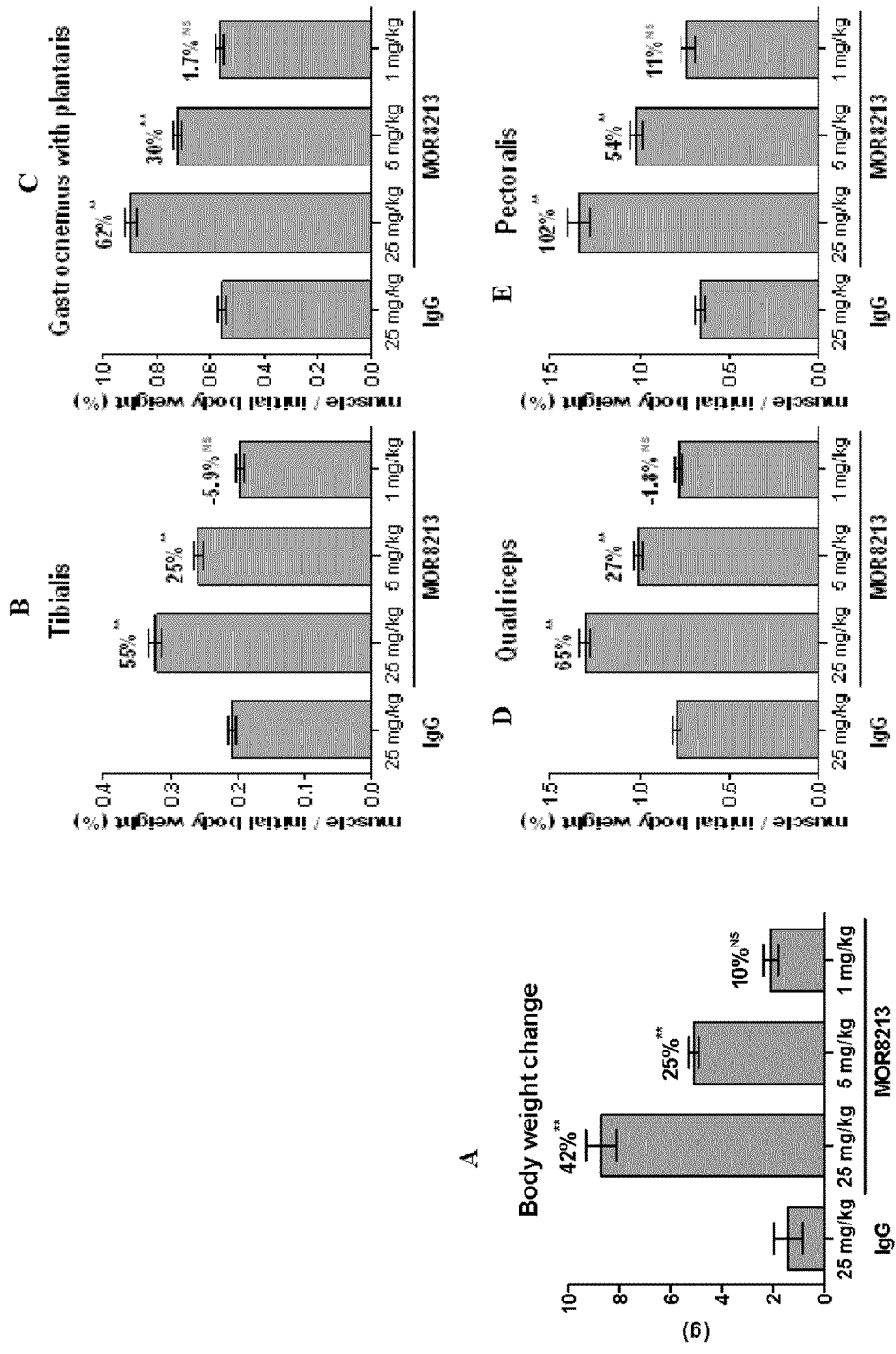
FIG. 7 shows mouse study: dose response in vivo efficacy study in naive animals—6 weeks treatment with MOR08213 at 25, 5, 1 mg/kg, dose-dependently increases body and muscle weight. Changes are shown for (A) body weight (B) Tibialis, (C) Gastrocnemius with plantaris, (D) Quadriceps and (E) Pectoralis.

MOR08213 is able to induce a dose-dependent profound hypertrophy of all examined muscles at 5 and 25 mg/kg while no significant changes are noticed at 1 mg/kg dose (FIG. 7).

Cross Blocking Studies

Stable human ActRIIB-transfected HEK293T/17 cells are maintained in DMEM containing 10% FBS, 2 mM L-glutamine, penicillin (50 IE/ml), streptomycin (50 µg/ml) and puromycin (2 µg/ml). Cells are grown in an incubator at 37° C. and 5% $CO_2$ and subcultured every 3-4 days. Cells are detached using Accutase™ and then transferred into a new flask containing fresh media.

The ability of the anti-ActRIIB antibodies to bind to the same epitope of human ActRIIB is assessed by FACS using hActRIIB-expressing cells.

For this, an anti-ActRIIB IgG is incubated with $1 \times 10^5$ hActRIIB-transfected cells per well for 1 h at 4° C. After washing, a different biotinylated anti-ActRIIB IgG or a control biotinylated IgG are incubated at equimolar concentration to the first anti-ActRIIB IgG for 1 h at 4° C. After washing, cell-bound biotonylated IgG are detected with streptavidin-APC (Biolegend). After one hour incubation at 4° C., the cells are washed again and resuspended in FACS buffer and fluorescence intensity of the cells is determined in a FACSArray™ instrument.

Figure 8:
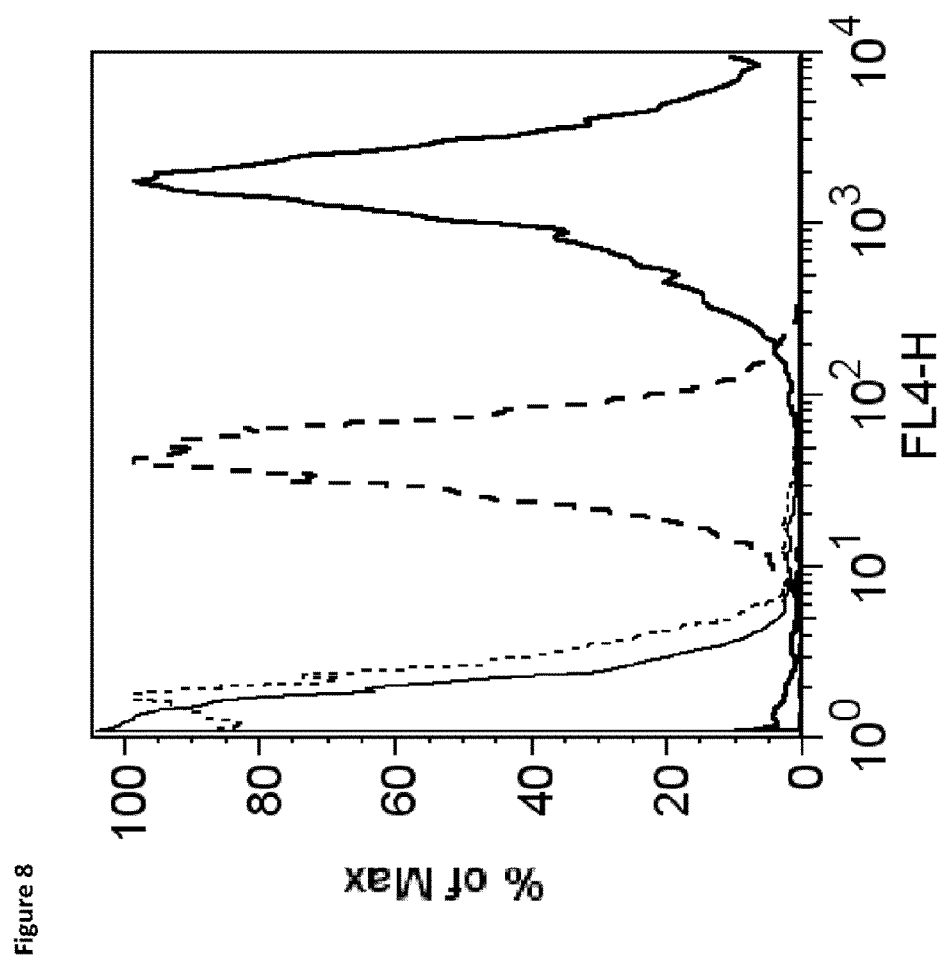
FIG. 8 shows a FACS output demonstrating cross-blocking between MOR08159 in the presence of MOR08213 (bold dashed) and MOR08159 alone (bold black), compared to isotype control alone (black) or isotype control in the presence of MOR08213 (dashed).

MOR08159 and MOR08213 are tested for their ability to jointly bind to human ActRIIB-transfected cells by FACS, and specific binding of MOR08159 alone (bold black) or in the presence of MOR08213 (bold dashed) is reported compared to isotype control (black) or isotype control in the presence of MOR08213 (dashed) (FIG. 8).

TABLE 5

IC50 and Emax determination of various ligand-induced inhibition of skeletal muscle differentiation assay in the presence or absence of MOR08159/MOR08213 (10 µg/ml)

| TGFβ family ligands | no Ab | | MOR08159 | | MOR08213 | |
| --- | --- | --- | --- | --- | --- | --- |
| | $IC_{50}$ (ng/ml) | $E_{max}$ (% control) | $IC_{50}$ (ng/ml) | $E_{max}$ (% control) | $IC_{50}$ (ng/ml) | $E_{max}$ (% control) |
| Myostatin | 8.5 ± 0.6 | 25.7 ± 1.5 | 42.7 ± 5.8 | 28.9 ± 4.8 | 35.1 ± 5.1 | 35.3 ± 4.5 |
| GDF-11 | 7.0 ± 1.2 | 23.2 ± 3.8 | 13.3 ± 0.9 | 22.1 ± 2.1 | 12.0 ± 1.0 | 27.1 ± 2.6 |
| Activin A | 14.7 ± 2.9 | 37.1 ± 3.9 | 34.7 ± 9.0 | 61.9 ± 5.4 | 41.9 ± 3.4 | 57.2 ± 1.9 |
| BMP-2 | 26.9 ± 2.6 | 2.6 ± 4.2 | 34.0 ± 2.6 | 5.1 ± 3.4 | 32.3 ± 1.4 | 4.8 ± 1.9 |

In the presence of MOR08213, binding of MOR08159 is significantly reduced suggesting that those two antibodies either bind to the same sites or to sites that may have some degree of overlap or that binding of MOR08213 to a distinct, but nearby site, might sterically hinder binding of MOR08159.

Epitope Mapping

Several complementary methods are used to determine the epitope to which the antibody MOR08159 binds. In this example, residue numbering is with reference to the full length ActRIIB amino acid sequence (SEQ ID NO: 181).

Dot Blot

A dot blot analysis of the MOR08159 epitope is carried out. Native and denatured (reduced and heat-denatured) ActRIIB is spotted on a nitrocellulose membrane, probed with MOR08159, and detected with a labeled anti-human antibody. Only native ActRIIB, but not reduced and heat-denatured ActRIIB is detected. The results indicated that the epitope is a conformational epitope.

Mutational Studies

A library of the extracellular domain of ActRIIB (aa 21-120) is generated by error-prone PCR and the variants are expressed in the periplasm of *E. coli*. The binding of about 30,000 (small fraction of the theoretical library size) of those variants to MOR08159 is tested by colony filter screeening and western staining. Variants which showed only weak or no binding to MOR08159 are further confirmed by ELISA. Expression level (detected with an anti-Flag antibody) and MOR08159 binding of the ActRIIB variants are compared to wild-type ActRIIB. If expression is at least 75% of wild type and binding to MOR08159 is less than 25%, the mutation is rated to be involved in MOR08159 binding. Only variants having a single point mutation, which is not obviously structure distorting (as e.g. the mutation of an S—S bridging cysteine would be) are considered.

Most mutations which prevented MOR08159 binding are found in a stretch from position K75 to D81, which indicates that this region is important for antibody binding. Mutations at positions W78, D80 and D81 are found to reduce MOR08159 binding significantly.

Cyclic Peptide Arrays

A collection of antigen derived cyclic peptides displayed on peptide microarrays are incubated with antibodies of interest. The determination of peptide-antibody binding is performed by RepliTope-analysis where the peptide microarray is incubated with the primary antibody followed by a fluorescently labelled secondary antibody directed against the Fc-part of the primary one. After several washing steps the peptide microarrays where dried using a microarray centrifuge and scanned in a high resolution microarray scanning system with appropriate wavelength settings.

The microarray is composed of three subarrays, each displaying cyclic peptides derived from ActRIIB (with Cys residue exchanged to Ser), which are scanned (peptide scan format 15/12). As control experiment, one incubation with unrelated antibody (ACE18543, isotope control) followed by fluorescently labelled secondary antibody (Cy-5 labelled anti-human IgG) is performed to determine false positive signals. Additionally, incubation with target antibody, followed by fluorescently labelled secondary antibody, is performed.

Antibody MOR08159 (ACE19819) is shown to recognise one epitope, which is found in three of the tested peptides (nos. 18-20).

| 18 | IELVKKGSWLDDFNS | (SEQ ID NO: 183) |
| 19 | VKKGSWLDDFNSYDR | (SEQ ID NO: 184) |
| 20 | GSWLDDFNSYDRQES | (SEQ ID NO: 185) |

The sequence common to these peptides to which MOR08159 is considered to bind is 76GCWLDDFNC84 (SEQ ID NO: 186).

A second region with weaker binding characteristics is also identified using this method. This second region has the sequence 49CEGEQDKRLHCYASW63 (SEQ ID NO: 187).

X-Ray Crystallography

Human ActRIIB aa20-120 and aa24-117 are expressed. In addition, MOR08159Fab and Fv regions are expressed and purified (all expression is carried out in *E. coli*). Using these proteins, four protein complexes are prepared, purified and crystallised (MOR08159Fab-ActRIIB 20-120, MOR08159Fab-ActRIIB 24-117, MOR08159Fv-ActRIIB 20-120, MOR08159Fv-ActRIIB 24-117).

The x-ray structure of free MOR08159Fab is resolved to 1.78 Å resolution. The x-ray structure of the Fv complex with ActRIIB-LBD is resolved to 3.35 Å resolution. Using the standard 3.9 Å distance cut-off to determine contact residues, it is confirmed that the sequence 76GCWLDDFNC84 is an important region with dominant binding contribution from the 78WLDDFN83 sequence (SEQ ID NO: 188). In addition, interaction is also found with the peptide region 49CEGE-QDKRLHCYASW63.

Figure 9:
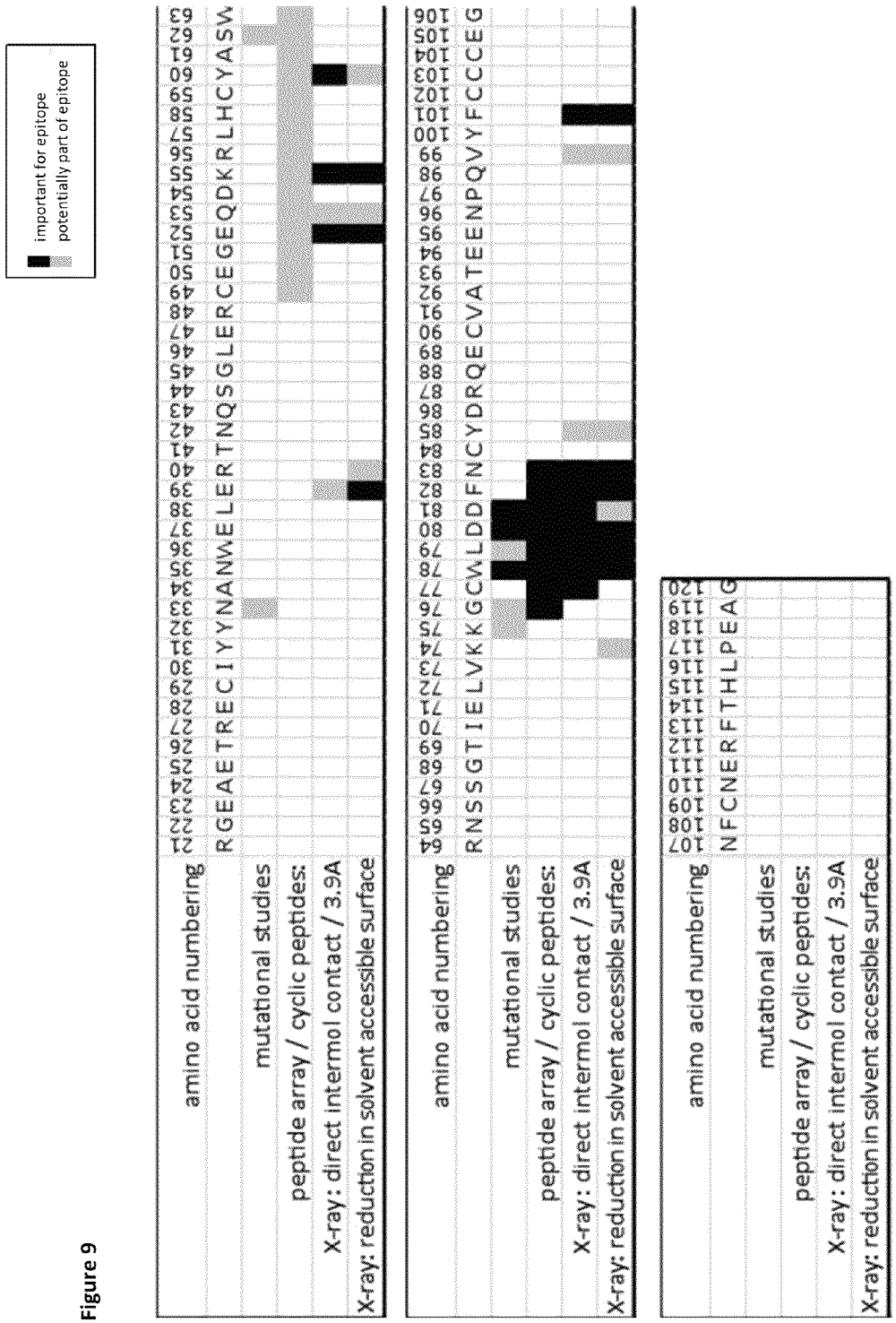
FIG. 9 shows an overview of ActRIIB residues (SEQ ID NO:181) to which MOR08159 binds, using various epitope determination techniques.

The results for the various epitope mapping experiments are summarised in FIG. 9.

Confirmation of Affinity by SET

Serial dilutions of antigen (extracellular domain of ActRIIB or ActRIIA) are prepared in PBS0.5% (w/v)BSA/0.02% (w/v)Tween 20 and antibody (MOR08159) is added to each antigen concentration to reach a constant antibody concentration. 100 µl/well of each dilution mix is distributed in duplicates to a 96-well polypropylene MTP (Greiner). Assay buffer served as negative control and a sample containing no antigen as positive control (Bmax). The plate is sealed and incubated overnight. A 96-well High Bind MTP (Meso Scale Discovery) is coated with 25 µl of 0.1 µg/ml mouse ActRIIB-Fc diluted in PBS. Also this plate is sealed and incubated over night at 4° C. After the incubation the antigen-coated High Bind MTP is washed with PBS/0.05%(w/v)Tween 20. Subsequently, the plate is blocked with PBS/5% (w/v) BSA. The washing steps are repeated and 50 µl/well of the antibody-antigen preparation from the polypropylene MTP is transferred into the antigen-coated High Bind MTP. The High Bind MTP is incubated for 25 min at room temperature. After three additional washing steps, 25 µl of 1 µg/ml Sulfo-Tag-labeled goat anti-human-detection antibody (Meso Scale Discovery) diluted in assay buffer is added to each well and incubated one hour at room temperature. After washing the plate, 50 µl of Read Buffer (Meso Scale Discovery) is transferred into each well. Electrochemiluminescence (ECL) signals are generated and detected by a Sector Imager 6000 reader (Meso Scale Discovery).

ECL values are plotted against the corresponding antigen concentrations. $K_D$ is determined by fitting the plot with the fit model described by Pichler J, et al. (J Immunol Methods; 1997, 201(2): 189-206).

The reported $K_D$ values and standard deviations are determined from the individual $K_D$ values obtained from independent experiments.

From these experiments a mean value for the dissociation equilibrium constant $K_D$ of 1.73 (±0.31) pM is determined for human ActRIIB, while a mean value for the dissociation equilibrium constant $K_D$ of 434 (+25) pM is determined for ActRIIA.

It will be understood that the disclosure has been described by way of example only and modifications may be made whilst remaining within the scope and spirit of the disclosure.

The invention claimed is:

1. An anti-ActRIIB antibody or functional fragment comprising an antigen binding portion thereof, wherein the antibody or functional fragment binds to the ligand-binding domain of ActRIIB, and wherein the antibody comprises a heavy chain variable region CDR1 comprising an amino acid sequence selected from the group consisting of SEQ ID NOs: 9 and 11; a heavy chain variable region CDR2 comprising an amino acid sequence selected from the group consisting of SEQ ID NOs: 23 and 25; a heavy chain variable region CDR3 comprising an amino acid sequence selected from the group consisting of SEQ ID NOs: 37 and 39; a light chain variable region CDR1 comprising an amino acid sequence selected from the group consisting of SEQ ID NOs: 51 and 53; a light chain variable region CDR2 comprising an amino acid sequence selected from the group consisting of SEQ ID NOs: 65 and 67; and a light chain variable region CDR3 comprising an amino acid sequence selected from the group consisting of SEQ ID NOs: 79 and 81.

2. The anti-ActRIIB antibody or functional fragment comprising an antigen binding portion thereof of claim 1, wherein the antibody or functional fragment binds to ActRIIB between amino acids 19-134 of SEQ ID NO: 181.

3. The anti-ActRIIB antibody or functional fragment comprising an antigen binding portion thereof of claim 1, wherein the antibody or functional fragment binds to ActRIIB with a $K_D$ of 1 nM or less.

4. The anti-ActRIIB antibody or functional fragment comprising an antigen binding portion thereof of claim 1, wherein the antibody or functional fragment binds to ActRIIB with a $K_D$ of 100 pM or less.

5. The anti-ActRIIB antibody or functional fragment comprising an antigen binding portion thereof of claim 1, wherein said antibody or functional fragment thereof inhibits myostatin binding to ActRIIB.

6. The anti-ActRIIB antibody or functional fragment comprising an antigen binding portion thereof of claim 1, wherein said antibody inhibits myostatin induced signalling as measured by a Smad dependent reporter gene assay.

7. The anti-ActRIIB antibody or functional fragment comprising an antigen binding portion thereof of claim 1, wherein said antibody binds to ActRIIB with a 10-fold or greater affinity than it binds to ActRIIA.

8. An anti-ActRIIB antibody or functional fragment comprising an antigen binding portion thereof, comprising:
(a) a heavy chain variable region CDR1 of SEQ ID NO: 9;
a heavy chain variable region CDR2 of SEQ ID NO: 23;
a heavy chain variable region CDR3 of SEQ ID NO: 37;
a light chain variable region CDR1 of SEQ ID NO: 51;
a light chain variable region CDR2 of SEQ ID NO: 65;
and a light chain variable region CDR3 of SEQ ID NO: 79; or
(b) a heavy chain variable region CDR1 of SEQ ID NO: 11;
a heavy chain variable region CDR2 of SEQ ID NO: 25;
a heavy chain variable region CDR3 of SEQ ID NO: 39;
a light chain variable region CDR1 of SEQ ID NO: 53;
a light chain variable region CDR2 of SEQ ID NO: 67;
and a light chain variable region CDR3 of SEQ ID NO: 81.

9. An anti-ActRIIB antibody or functional fragment comprising an antigen binding portion thereof comprising:
(a) the variable light chain sequence of SEQ ID NO: 93 and variable heavy chain sequence of SEQ ID NO: 107; or (b) the variable light chain sequence of SEQ ID NO: 95 and variable heavy chain sequence of SEQ ID NO: 109.

10. The antibody or functional fragment comprising an antigen binding portion thereof of claim 1, which binds to an epitope comprising or consisting of:
(a) amino acids 78-83 of SEQ ID NO: 181 (WLDDFN—SEQ ID NO:188); or
(b) amino acids 76-84 of SEQ ID NO: 181 (GCWLDDFNC—SEQ ID NO:186); or
(c) amino acids 75-85 of SEQ ID NO: 181 (KGCWLDDFNCY—SEQ ID NO:190); or
(d) amino acids 52-56 of SEQ ID NO: 181 (EQDKR—SEQ ID NO:189); or
(e) amino acids 49-63 of SEQ ID NO: 181 (CEGEQDKRLHCYASW—SEQ ID NO:187); or
(f) amino acids 78-83 of SEQ ID NO: 181 (WLDDFN) and amino acids 52-56 of SEQ ID NO: 181 (EQDKR).

11. The antibody or functional fragment comprising an antigen binding portion thereof of claim 1, wherein said antibody is of the IgG1 isotype.

12. The antibody or functional fragment comprising an antigen binding portion thereof of claim 1, which has altered effector function through mutation of the Fc region.

13. An isolated polynucleotide sequence encoding the variable heavy chain and/or variable light chain of an antibody or functional fragment comprising an antigen binding portion thereof, wherein the antibody or functional fragment binds to the ligand-binding domain of ActRIIB, and wherein the antibody comprises a heavy chain variable region CDR1 comprising an amino acid sequence selected from the group consisting of SEQ ID NOs: 9 and 11; a heavy chain variable region CDR2 comprising an amino acid sequence selected from the group consisting of SEQ ID NOs: 23 and 25; a heavy chain variable region CDR3 comprising an amino acid sequence selected from the group consisting of SEQ ID NOs: 37 and 39; a light chain variable region CDR1 comprising an amino acid sequence selected from the group consisting of SEQ ID NOs: 51 and 53; a light chain variable region CDR2 comprising an amino acid sequence selected from the group consisting of SEQ ID NOs: 65 and 67; and a light chain variable region CDR3 comprising an amino acid sequence selected from the group consisting of SEQ ID NOs: 79 and 81.

14. A cloning or expression vector comprising one or more copies of an isolated polynucleotide sequence of claim 13.

15. A host cell comprising one or more copies of the vector of claim 14.

16. A process for the production of an antibody or functional fragment comprising an antigen binding portion thereof, comprising culturing a host cell comprising a cloning or expression vector encoding the antibody or functional fragment comprising an antigen binding portion thereof of claim 1, and isolating the antibody or functional fragment comprising an antigen binding portion thereof.

17. A pharmaceutical composition comprising an antibody or functional fragment comprising an antigen binding portion thereof of claim 1.

18. A pharmaceutical composition of claim 17, further comprising a pharmaceutically acceptable diluent or carrier.

19. A pharmaceutical composition of claim 17, further comprising one or more additional active agents.

20. A pharmaceutical composition of claim 19, wherein said additional active agent is selected from IGF-1, IGF-2 or active variants of IGF-1 or IGF-2, an anti-myostatin antibody, a myostatin propeptide, a myostatin decoy protein that binds ActRIIB but does not activate it, a beta 2 agonist, a Ghrelin agonist, a SARM, GH agonists/mimetics, and follistatin.

21. A method of increasing muscle mass in a patient suffering from a musculoskeletal disease or disorder; acute and/or chronic renal disease or failure; liver fibrosis or cirrhosis; cancer; breast cancer; Parkinson's Disease; conditions associated with neuronal death; ALS; brain atrophy; dementia; anemia; liver, kidney and pulmonary fibrosis; one or more age-related condition; rhabdomyosarcoma; bone-loss inducing cancer; hepatocellular carcinoma; and/or gastrointestinal cancer, comprising the step of:
administering an effective dose of an antibody or functional fragment comprising an antigen binding portion thereof of claim 1 to said patient.

22. A pharmaceutical composition comprising the antibody of claim 1.

23. A method of ameliorating the muscle wasting effects of enforced inactivity or time spent in a zero gravity environment comprising administering an effective dose of the antibody or functional fragment comprising an antigen binding portion thereof of claim 1, prior to said period of enforced inactivity or time spent in a zero gravity environment.

24. The method of claim 21, wherein the patient being treated has a fracture to a limb or joint.

25. The method of claim 23, wherein the patient has undergone or is about to undergo, hip or knee replacement surgery.

26. An antibody encoded by pBW524 (DSM22874).

27. An anti-ActRIIB antibody or functional fragment comprising an antigen binding portion thereof, comprising: a variable heavy chain sequence and a variable light chain sequence, wherein the variable light chain sequence comprises SEQ ID NO: 93.

28. An anti-ActRIIB antibody or functional fragment comprising an antigen binding portion thereof, comprising: a variable heavy chain sequence and a variable light chain sequence, wherein the variable heavy chain sequence comprises: a heavy chain variable region CDR1 comprising SEQ ID NO: 9; a heavy chain variable region CDR2 comprising SEQ ID NO: 23; and a heavy chain variable region CDR3 comprising SEQ ID NO: 37.

29. An anti-ActRIIB antibody or functional fragment comprising an antigen binding portion thereof comprising: a variable heavy chain sequence and a variable light chain sequence, wherein the variable heavy chain sequence comprises SEQ ID NO: 107.

30. An anti-ActRIIB antibody or functional fragment comprising an antigen binding portion thereof, comprising: a variable heavy chain sequence and a variable light chain sequence, wherein the variable light chain sequence comprises: a light chain variable region CDR1 comprising SEQ ID NO: 51, a light chain variable region CDR2 comprising SEQ ID NO: 65; and a light chain variable region CDR3 comprising SEQ ID NO: 79.

31. A method of increasing muscle mass in a patient in need thereof, comprising the step of:
administering an effective dose of an antibody or functional fragment comprising an antigen binding portion thereof of claim 1 to said patient.

32. A method of increasing muscle mass in a human being, comprising the step of:
administering an effective dose of an antibody or functional fragment comprising an antigen binding portion thereof of claim 1 to said human being.

33. An anti-ActRIIB antibody or functional fragment comprising an antigen binding portion thereof, comprising:
a heavy chain variable region CDR1 of SEQ ID NO: 9; a heavy chain variable region CDR2 of SEQ ID NO: 23; a heavy chain variable region CDR3 of SEQ ID NO: 37; a light chain variable region CDR1 of SEQ ID NO: 51; a light chain variable region CDR2 of SEQ ID NO: 65; and a light chain variable region CDR3 of SEQ ID NO: 79.

34. An anti-ActRIIB antibody or functional fragment comprising an antigen binding portion thereof, comprising:
a heavy chain variable region CDR1 of SEQ ID NO: 11; a heavy chain variable region CDR2 of SEQ ID NO: 25; a heavy chain variable region CDR3 of SEQ ID NO: 39; a light chain variable region CDR1 of SEQ ID NO: 53; a light chain variable region CDR2 of SEQ ID NO: 67; and a light chain variable region CDR3 of SEQ ID NO: 81.

* * * * *

SEQUENCE LISTING

```
<160> NUMBER OF SEQ ID NOS: 190

<210> SEQ ID NO 1
<211> LENGTH: 10
<212> TYPE: PRT
<213> ORGANISM: Artificial
<220> FEATURE:
<223> OTHER INFORMATION: CDR

<400> SEQUENCE: 1

Gly Tyr Thr Phe Thr Ser Ser Tyr Ile Asn
1               5                   10

<210> SEQ ID NO 2
<211> LENGTH: 10
<212> TYPE: PRT
<213> ORGANISM: Artificial
<220> FEATURE:
<223> OTHER INFORMATION: CDR

<400> SEQUENCE: 2

Gly Tyr Thr Phe Thr Ser Ser Tyr Ile Asn
1               5                   10

<210> SEQ ID NO 3
<211> LENGTH: 10
<212> TYPE: PRT
<213> ORGANISM: Artificial
<220> FEATURE:
<223> OTHER INFORMATION: CDR

<400> SEQUENCE: 3

Gly Tyr Thr Phe Thr Ser Ser Tyr Ile Asn
1               5                   10

<210> SEQ ID NO 4
<211> LENGTH: 10
<212> TYPE: PRT
<213> ORGANISM: Artificial
<220> FEATURE:
<223> OTHER INFORMATION: CDR

<400> SEQUENCE: 4

Gly Tyr Thr Phe Thr Ser Ser Tyr Ile Asn
1               5                   10

<210> SEQ ID NO 5
<211> LENGTH: 10
<212> TYPE: PRT
<213> ORGANISM: Artificial
<220> FEATURE:
<223> OTHER INFORMATION: CDR

<400> SEQUENCE: 5

Gly Tyr Thr Phe Thr Ser Ser Tyr Ile Asn
1               5                   10

<210> SEQ ID NO 6
<211> LENGTH: 10
<212> TYPE: PRT
<213> ORGANISM: Artificial
<220> FEATURE:
```

<223> OTHER INFORMATION: CDR

<400> SEQUENCE: 6

Gly Tyr Thr Phe Thr Ser Ser Tyr Ile Asn
1               5                   10

<210> SEQ ID NO 7
<211> LENGTH: 10
<212> TYPE: PRT
<213> ORGANISM: Artificial
<220> FEATURE:
<223> OTHER INFORMATION: CDR

<400> SEQUENCE: 7

Gly Tyr Thr Phe Thr Ser Ser Tyr Ile Asn
1               5                   10

<210> SEQ ID NO 8
<211> LENGTH: 10
<212> TYPE: PRT
<213> ORGANISM: Artificial
<220> FEATURE:
<223> OTHER INFORMATION: CDR

<400> SEQUENCE: 8

Gly Tyr Thr Phe Thr Ser Ser Tyr Ile Asn
1               5                   10

<210> SEQ ID NO 9
<211> LENGTH: 10
<212> TYPE: PRT
<213> ORGANISM: Artificial
<220> FEATURE:
<223> OTHER INFORMATION: CDR

<400> SEQUENCE: 9

Gly Tyr Thr Phe Thr Ser Ser Tyr Ile Asn
1               5                   10

<210> SEQ ID NO 10
<211> LENGTH: 10
<212> TYPE: PRT
<213> ORGANISM: Artificial
<220> FEATURE:
<223> OTHER INFORMATION: CDR

<400> SEQUENCE: 10

Gly Tyr Thr Phe Thr Ser Ser Tyr Ile Asn
1               5                   10

<210> SEQ ID NO 11
<211> LENGTH: 10
<212> TYPE: PRT
<213> ORGANISM: Artificial
<220> FEATURE:
<223> OTHER INFORMATION: CDR

<400> SEQUENCE: 11

Gly Tyr Thr Phe Thr Ser Ser Tyr Ile Asn
1               5                   10

<210> SEQ ID NO 12
<211> LENGTH: 10
<212> TYPE: PRT
<213> ORGANISM: Artificial
<220> FEATURE:
<223> OTHER INFORMATION: CDR

<400> SEQUENCE: 12

Gly Tyr Thr Phe Thr Ser Ser Tyr Ile Asn
1               5                   10

<210> SEQ ID NO 13
<211> LENGTH: 10
<212> TYPE: PRT
<213> ORGANISM: Artificial
<220> FEATURE:
<223> OTHER INFORMATION: CDR

<400> SEQUENCE: 13

Gly Tyr Thr Phe Thr Ser Ser Tyr Ile Asn
1               5                   10

<210> SEQ ID NO 14
<211> LENGTH: 10
<212> TYPE: PRT
<213> ORGANISM: Artificial
<220> FEATURE:
<223> OTHER INFORMATION: CDR

<400> SEQUENCE: 14

Gly Tyr Thr Phe Thr Ser Ser Tyr Ile Asn
1               5                   10

<210> SEQ ID NO 15
<211> LENGTH: 17
<212> TYPE: PRT
<213> ORGANISM: Artificial
<220> FEATURE:
<223> OTHER INFORMATION: CDR

<400> SEQUENCE: 15

Thr Ile Asn Pro Val Ser Gly Asn Thr Ser Tyr Ala Gln Lys Phe Gln
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: CDR

<400> SEQUENCE: 16

Thr Ile Asn Pro Val Ser Gly Asn Thr Ser Tyr Ala Gln Lys Phe Gln
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: CDR

<400> SEQUENCE: 17

Thr Ile Asn Pro Val Ser Gly Asn Thr Ser Tyr Ala Gln Lys Phe Gln
1               5                   10                  15

Gly

<210> SEQ ID NO 18
<211> LENGTH: 17
<212> TYPE: PRT

```
<213> ORGANISM: Artificial
<220> FEATURE:
<223> OTHER INFORMATION: CDR

<400> SEQUENCE: 18

Thr Ile Asn Pro Val Ser Gly Asn Thr Ser Tyr Ala Gln Lys Phe Gln
1               5                   10                  15
Gly

<210> SEQ ID NO 19
<211> LENGTH: 17
<212> TYPE: PRT
<213> ORGANISM: Artificial
<220> FEATURE:
<223> OTHER INFORMATION: CDR

<400> SEQUENCE: 19

Met Ile Asn Ala Pro Ile Gly Thr Thr Arg Tyr Ala Gln Lys Phe Gln
1               5                   10                  15
Gly

<210> SEQ ID NO 20
<211> LENGTH: 17
<212> TYPE: PRT
<213> ORGANISM: Artificial
<220> FEATURE:
<223> OTHER INFORMATION: CDR

<400> SEQUENCE: 20

Gln Ile Asn Ala Ala Ser Gly Met Thr Arg Tyr Ala Gln Lys Phe Gln
1               5                   10                  15
Gly

<210> SEQ ID NO 21
<211> LENGTH: 17
<212> TYPE: PRT
<213> ORGANISM: Artificial
<220> FEATURE:
<223> OTHER INFORMATION: CDR

<400> SEQUENCE: 21

Met Ile Asn Ala Pro Ile Gly Thr Thr Arg Tyr Ala Gln Lys Phe Gln
1               5                   10                  15
Gly

<210> SEQ ID NO 22
<211> LENGTH: 17
<212> TYPE: PRT
<213> ORGANISM: Artificial
<220> FEATURE:
<223> OTHER INFORMATION: CDR

<400> SEQUENCE: 22

Thr Ile Asn Pro Val Ser Gly Asn Thr Arg Tyr Ala Gln Lys Phe Gln
1               5                   10                  15
Gly

<210> SEQ ID NO 23
<211> LENGTH: 17
<212> TYPE: PRT
<213> ORGANISM: Artificial
<220> FEATURE:
<223> OTHER INFORMATION: CDR

<400> SEQUENCE: 23
```

Thr Ile Asn Pro Val Ser Gly Ser Thr Ser Tyr Ala Gln Lys Phe Gln
1               5                   10                  15
Gly

<210> SEQ ID NO 24
<211> LENGTH: 17
<212> TYPE: PRT
<213> ORGANISM: Artificial
<220> FEATURE:
<223> OTHER INFORMATION: CDR

<400> SEQUENCE: 24

Gln Ile Asn Ala Ala Ser Gly Met Thr Arg Tyr Ala Gln Lys Phe Gln
1               5                   10                  15
Gly

<210> SEQ ID NO 25
<211> LENGTH: 17
<212> TYPE: PRT
<213> ORGANISM: Artificial
<220> FEATURE:
<223> OTHER INFORMATION: CDR

<400> SEQUENCE: 25

Asn Ile Asn Ala Ala Ala Gly Ile Thr Leu Tyr Ala Gln Lys Phe Gln
1               5                   10                  15
Gly

<210> SEQ ID NO 26
<211> LENGTH: 17
<212> TYPE: PRT
<213> ORGANISM: Artificial
<220> FEATURE:
<223> OTHER INFORMATION: CDR

<400> SEQUENCE: 26

Thr Ile Asn Pro Pro Thr Gly Gly Thr Tyr Tyr Ala Gln Lys Phe Gln
1               5                   10                  15
Gly

<210> SEQ ID NO 27
<211> LENGTH: 17
<212> TYPE: PRT
<213> ORGANISM: Artificial
<220> FEATURE:
<223> OTHER INFORMATION: CDR

<400> SEQUENCE: 27

Gly Ile Asn Pro Pro Ala Gly Thr Thr Ser Tyr Ala Gln Lys Phe Gln
1               5                   10                  15
Gly

<210> SEQ ID NO 28
<211> LENGTH: 17
<212> TYPE: PRT
<213> ORGANISM: Artificial
<220> FEATURE:
<223> OTHER INFORMATION: CDR

<400> SEQUENCE: 28

Asn Ile Asn Pro Ala Thr Gly His Ala Asp Tyr Ala Gln Lys Phe Gln
1               5                   10                  15
Gly

```
<210> SEQ ID NO 29
<211> LENGTH: 6
<212> TYPE: PRT
<213> ORGANISM: Artificial
<220> FEATURE:
<223> OTHER INFORMATION: CDR

<400> SEQUENCE: 29

Gly Gly Trp Phe Asp Tyr
1               5

<210> SEQ ID NO 30
<211> LENGTH: 6
<212> TYPE: PRT
<213> ORGANISM: Artificial
<220> FEATURE:
<223> OTHER INFORMATION: CDR

<400> SEQUENCE: 30

Gly Gly Trp Phe Asp Tyr
1               5

<210> SEQ ID NO 31
<211> LENGTH: 6
<212> TYPE: PRT
<213> ORGANISM: Artificial
<220> FEATURE:
<223> OTHER INFORMATION: CDR

<400> SEQUENCE: 31

Gly Gly Trp Phe Asp Tyr
1               5

<210> SEQ ID NO 32
<211> LENGTH: 6
<212> TYPE: PRT
<213> ORGANISM: Artificial
<220> FEATURE:
<223> OTHER INFORMATION: CDR

<400> SEQUENCE: 32

Gly Gly Trp Phe Asp Tyr
1               5

<210> SEQ ID NO 33
<211> LENGTH: 6
<212> TYPE: PRT
<213> ORGANISM: Artificial
<220> FEATURE:
<223> OTHER INFORMATION: CDR

<400> SEQUENCE: 33

Gly Gly Trp Phe Asp Tyr
1               5

<210> SEQ ID NO 34
<211> LENGTH: 6
<212> TYPE: PRT
<213> ORGANISM: Artificial
<220> FEATURE:
<223> OTHER INFORMATION: CDR

<400> SEQUENCE: 34

Gly Gly Trp Phe Asp Tyr
1               5
```

```
<210> SEQ ID NO 35
<211> LENGTH: 6
<212> TYPE: PRT
<213> ORGANISM: Artificial
<220> FEATURE:
<223> OTHER INFORMATION: CDR

<400> SEQUENCE: 35

Gly Gly Trp Phe Asp Tyr
1               5

<210> SEQ ID NO 36
<211> LENGTH: 6
<212> TYPE: PRT
<213> ORGANISM: Artificial
<220> FEATURE:
<223> OTHER INFORMATION: CDR

<400> SEQUENCE: 36

Gly Gly Trp Phe Asp Tyr
1               5

<210> SEQ ID NO 37
<211> LENGTH: 6
<212> TYPE: PRT
<213> ORGANISM: Artificial
<220> FEATURE:
<223> OTHER INFORMATION: CDR

<400> SEQUENCE: 37

Gly Gly Trp Phe Asp Tyr
1               5

<210> SEQ ID NO 38
<211> LENGTH: 6
<212> TYPE: PRT
<213> ORGANISM: Artificial
<220> FEATURE:
<223> OTHER INFORMATION: CDR

<400> SEQUENCE: 38

Gly Gly Trp Phe Asp Tyr
1               5

<210> SEQ ID NO 39
<211> LENGTH: 6
<212> TYPE: PRT
<213> ORGANISM: Artificial
<220> FEATURE:
<223> OTHER INFORMATION: CDR

<400> SEQUENCE: 39

Gly Gly Trp Phe Asp Tyr
1               5

<210> SEQ ID NO 40
<211> LENGTH: 6
<212> TYPE: PRT
<213> ORGANISM: Artificial
<220> FEATURE:
<223> OTHER INFORMATION: CDR

<400> SEQUENCE: 40

Gly Gly Trp Phe Asp Tyr
1               5

<210> SEQ ID NO 41
<211> LENGTH: 6
```

```
<212> TYPE: PRT
<213> ORGANISM: Artificial
<220> FEATURE:
<223> OTHER INFORMATION: CDR

<400> SEQUENCE: 41

Gly Gly Trp Phe Asp Tyr
1               5

<210> SEQ ID NO 42
<211> LENGTH: 6
<212> TYPE: PRT
<213> ORGANISM: Artificial
<220> FEATURE:
<223> OTHER INFORMATION: CDR

<400> SEQUENCE: 42

Gly Gly Trp Phe Asp Tyr
1               5

<210> SEQ ID NO 43
<211> LENGTH: 14
<212> TYPE: PRT
<213> ORGANISM: Artificial
<220> FEATURE:
<223> OTHER INFORMATION: CDR

<400> SEQUENCE: 43

Thr Gly Thr Ser Ser Asp Val Gly Ser Tyr Asn Tyr Val Asn
1               5                   10

<210> SEQ ID NO 44
<211> LENGTH: 14
<212> TYPE: PRT
<213> ORGANISM: Artificial
<220> FEATURE:
<223> OTHER INFORMATION: CDR

<400> SEQUENCE: 44

Thr Gly Thr Ser Ser Asp Val Gly Ser Tyr Asn Tyr Val Asn
1               5                   10

<210> SEQ ID NO 45
<211> LENGTH: 14
<212> TYPE: PRT
<213> ORGANISM: Artificial
<220> FEATURE:
<223> OTHER INFORMATION: CDR

<400> SEQUENCE: 45

Thr Gly Thr Ser Ser Asp Val Gly Ser Tyr Asn Tyr Val Asn
1               5                   10

<210> SEQ ID NO 46
<211> LENGTH: 14
<212> TYPE: PRT
<213> ORGANISM: Artificial
<220> FEATURE:
<223> OTHER INFORMATION: CDR

<400> SEQUENCE: 46

Thr Gly Thr Ser Ser Asp Val Gly Ser Tyr Asn Tyr Val Asn
1               5                   10

<210> SEQ ID NO 47
<211> LENGTH: 14
<212> TYPE: PRT
<213> ORGANISM: Artificial
```

```
<220> FEATURE:
<223> OTHER INFORMATION: CDR

<400> SEQUENCE: 47

Thr Gly Thr Ser Ser Asp Val Gly Ser Tyr Asn Tyr Val Asn
1               5                   10

<210> SEQ ID NO 48
<211> LENGTH: 14
<212> TYPE: PRT
<213> ORGANISM: Artificial
<220> FEATURE:
<223> OTHER INFORMATION: CDR

<400> SEQUENCE: 48

Thr Gly Thr Ser Ser Asp Val Gly Ser Tyr Asn Tyr Val Asn
1               5                   10

<210> SEQ ID NO 49
<211> LENGTH: 14
<212> TYPE: PRT
<213> ORGANISM: Artificial
<220> FEATURE:
<223> OTHER INFORMATION: CDR

<400> SEQUENCE: 49

Thr Gly Thr Ser Ser Asp Val Gly Ser Tyr Asn Tyr Val Asn
1               5                   10

<210> SEQ ID NO 50
<211> LENGTH: 14
<212> TYPE: PRT
<213> ORGANISM: Artificial
<220> FEATURE:
<223> OTHER INFORMATION: CDR

<400> SEQUENCE: 50

Thr Gly Thr Ser Ser Asp Val Gly Ser Tyr Asn Tyr Val Asn
1               5                   10

<210> SEQ ID NO 51
<211> LENGTH: 14
<212> TYPE: PRT
<213> ORGANISM: Artificial
<220> FEATURE:
<223> OTHER INFORMATION: CDR

<400> SEQUENCE: 51

Thr Gly Thr Ser Ser Asp Val Gly Ser Tyr Asn Tyr Val Asn
1               5                   10

<210> SEQ ID NO 52
<211> LENGTH: 14
<212> TYPE: PRT
<213> ORGANISM: Artificial
<220> FEATURE:
<223> OTHER INFORMATION: CDR

<400> SEQUENCE: 52

Thr Gly Thr Ser Ser Asp Val Gly Ser Tyr Asn Tyr Val Asn
1               5                   10

<210> SEQ ID NO 53
<211> LENGTH: 14
<212> TYPE: PRT
<213> ORGANISM: Artificial
<220> FEATURE:
<223> OTHER INFORMATION: CDR
```

```
<400> SEQUENCE: 53

Thr Gly Thr Ser Ser Asp Val Gly Ser Tyr Asn Tyr Val Asn
 1               5                  10

<210> SEQ ID NO 54
<211> LENGTH: 14
<212> TYPE: PRT
<213> ORGANISM: Artificial
<220> FEATURE:
<223> OTHER INFORMATION: CDR

<400> SEQUENCE: 54

Thr Gly Thr Ser Ser Asp Val Gly Ser Tyr Asn Tyr Val Asn
 1               5                  10

<210> SEQ ID NO 55
<211> LENGTH: 14
<212> TYPE: PRT
<213> ORGANISM: Artificial
<220> FEATURE:
<223> OTHER INFORMATION: CDR

<400> SEQUENCE: 55

Thr Gly Thr Ser Ser Asp Val Gly Ser Tyr Asn Tyr Val Asn
 1               5                  10

<210> SEQ ID NO 56
<211> LENGTH: 14
<212> TYPE: PRT
<213> ORGANISM: Artificial
<220> FEATURE:
<223> OTHER INFORMATION: CDR

<400> SEQUENCE: 56

Thr Gly Thr Ser Ser Asp Val Gly Ser Tyr Asn Tyr Val Asn
 1               5                  10

<210> SEQ ID NO 57
<211> LENGTH: 11
<212> TYPE: PRT
<213> ORGANISM: Artificial
<220> FEATURE:
<223> OTHER INFORMATION: CDR

<400> SEQUENCE: 57

Leu Met Ile Tyr Gly Val Ser Lys Arg Pro Ser
 1               5                  10

<210> SEQ ID NO 58
<211> LENGTH: 11
<212> TYPE: PRT
<213> ORGANISM: Artificial
<220> FEATURE:
<223> OTHER INFORMATION: CDR

<400> SEQUENCE: 58

Leu Met Ile Tyr Gly Val Ser Lys Arg Pro Ser
 1               5                  10

<210> SEQ ID NO 59
<211> LENGTH: 11
<212> TYPE: PRT
<213> ORGANISM: Artificial
<220> FEATURE:
<223> OTHER INFORMATION: CDR

<400> SEQUENCE: 59
```

Leu Met Ile Tyr Gly Val Ser Lys Arg Pro Ser
1               5                   10

<210> SEQ ID NO 60
<211> LENGTH: 11
<212> TYPE: PRT
<213> ORGANISM: Artificial
<220> FEATURE:
<223> OTHER INFORMATION: CDR

<400> SEQUENCE: 60

Leu Met Ile Tyr Gly Val Ser Lys Arg Pro Ser
1               5                   10

<210> SEQ ID NO 61
<211> LENGTH: 11
<212> TYPE: PRT
<213> ORGANISM: Artificial
<220> FEATURE:
<223> OTHER INFORMATION: CDR

<400> SEQUENCE: 61

Leu Met Ile Tyr Gly Val Ser Lys Arg Pro Ser
1               5                   10

<210> SEQ ID NO 62
<211> LENGTH: 11
<212> TYPE: PRT
<213> ORGANISM: Artificial
<220> FEATURE:
<223> OTHER INFORMATION: CDR

<400> SEQUENCE: 62

Leu Met Ile Tyr Gly Val Ser Lys Arg Pro Ser
1               5                   10

<210> SEQ ID NO 63
<211> LENGTH: 11
<212> TYPE: PRT
<213> ORGANISM: Artificial
<220> FEATURE:
<223> OTHER INFORMATION: CDR

<400> SEQUENCE: 63

Leu Met Ile Tyr Gly Val Ser Lys Arg Pro Ser
1               5                   10

<210> SEQ ID NO 64
<211> LENGTH: 11
<212> TYPE: PRT
<213> ORGANISM: Artificial
<220> FEATURE:
<223> OTHER INFORMATION: CDR

<400> SEQUENCE: 64

Leu Met Ile Tyr Gly Val Ser Lys Arg Pro Ser
1               5                   10

<210> SEQ ID NO 65
<211> LENGTH: 11
<212> TYPE: PRT
<213> ORGANISM: Artificial
<220> FEATURE:
<223> OTHER INFORMATION: CDR

<400> SEQUENCE: 65

Leu Met Ile Tyr Gly Val Ser Lys Arg Pro Ser

```
<210> SEQ ID NO 66
<211> LENGTH: 11
<212> TYPE: PRT
<213> ORGANISM: Artificial
<220> FEATURE:
<223> OTHER INFORMATION: CDR

<400> SEQUENCE: 66

Leu Met Ile Tyr Gly Val Ser Lys Arg Pro Ser
1               5                   10

<210> SEQ ID NO 67
<211> LENGTH: 11
<212> TYPE: PRT
<213> ORGANISM: Artificial
<220> FEATURE:
<223> OTHER INFORMATION: CDR

<400> SEQUENCE: 67

Leu Met Ile Tyr Gly Val Ser Lys Arg Pro Ser
1               5                   10

<210> SEQ ID NO 68
<211> LENGTH: 11
<212> TYPE: PRT
<213> ORGANISM: Artificial
<220> FEATURE:
<223> OTHER INFORMATION: CDR

<400> SEQUENCE: 68

Leu Met Ile Tyr Gly Val Ser Lys Arg Pro Ser
1               5                   10

<210> SEQ ID NO 69
<211> LENGTH: 11
<212> TYPE: PRT
<213> ORGANISM: Artificial
<220> FEATURE:
<223> OTHER INFORMATION: CDR

<400> SEQUENCE: 69

Leu Met Ile Tyr Gly Val Ser Lys Arg Pro Ser
1               5                   10

<210> SEQ ID NO 70
<211> LENGTH: 11
<212> TYPE: PRT
<213> ORGANISM: Artificial
<220> FEATURE:
<223> OTHER INFORMATION: CDR

<400> SEQUENCE: 70

Leu Met Ile Tyr Gly Val Ser Lys Arg Pro Ser
1               5                   10

<210> SEQ ID NO 71
<211> LENGTH: 9
<212> TYPE: PRT
<213> ORGANISM: Artificial
<220> FEATURE:
<223> OTHER INFORMATION: CDR

<400> SEQUENCE: 71

Gln Ala Trp Thr Ser Lys Met Ala Gly
1               5
```

```
<210> SEQ ID NO 72
<211> LENGTH: 9
<212> TYPE: PRT
<213> ORGANISM: Artificial
<220> FEATURE:
<223> OTHER INFORMATION: CDR

<400> SEQUENCE: 72

Ser Ser Tyr Thr Arg Met Gly His Pro
1               5

<210> SEQ ID NO 73
<211> LENGTH: 10
<212> TYPE: PRT
<213> ORGANISM: Artificial
<220> FEATURE:
<223> OTHER INFORMATION: CDR

<400> SEQUENCE: 73

Ala Thr Tyr Gly Lys Gly Val Thr Pro Pro
1               5                   10

<210> SEQ ID NO 74
<211> LENGTH: 10
<212> TYPE: PRT
<213> ORGANISM: Artificial
<220> FEATURE:
<223> OTHER INFORMATION: CDR

<400> SEQUENCE: 74

Gly Thr Phe Ala Gly Gly Ser Tyr Tyr Gly
1               5                   10

<210> SEQ ID NO 75
<211> LENGTH: 9
<212> TYPE: PRT
<213> ORGANISM: Artificial
<220> FEATURE:
<223> OTHER INFORMATION: CDR

<400> SEQUENCE: 75

Gln Ala Trp Thr Ser Lys Met Ala Gly
1               5

<210> SEQ ID NO 76
<211> LENGTH: 9
<212> TYPE: PRT
<213> ORGANISM: Artificial
<220> FEATURE:
<223> OTHER INFORMATION: CDR

<400> SEQUENCE: 76

Gln Ala Trp Thr Ser Lys Met Ala Gly
1               5

<210> SEQ ID NO 77
<211> LENGTH: 10
<212> TYPE: PRT
<213> ORGANISM: Artificial
<220> FEATURE:
<223> OTHER INFORMATION: CDR

<400> SEQUENCE: 77

Gly Thr Phe Ala Gly Gly Ser Tyr Tyr Gly
1               5                   10

<210> SEQ ID NO 78
```

```
<211> LENGTH: 10
<212> TYPE: PRT
<213> ORGANISM: Artificial
<220> FEATURE:
<223> OTHER INFORMATION: CDR

<400> SEQUENCE: 78

Gly Thr Phe Ala Gly Gly Ser Tyr Tyr Gly
1               5                   10

<210> SEQ ID NO 79
<211> LENGTH: 10
<212> TYPE: PRT
<213> ORGANISM: Artificial
<220> FEATURE:
<223> OTHER INFORMATION: CDR

<400> SEQUENCE: 79

Gly Thr Phe Ala Gly Gly Ser Tyr Tyr Gly
1               5                   10

<210> SEQ ID NO 80
<211> LENGTH: 10
<212> TYPE: PRT
<213> ORGANISM: Artificial
<220> FEATURE:
<223> OTHER INFORMATION: CDR

<400> SEQUENCE: 80

Gly Thr Phe Ala Gly Gly Ser Tyr Tyr Gly
1               5                   10

<210> SEQ ID NO 81
<211> LENGTH: 10
<212> TYPE: PRT
<213> ORGANISM: Artificial
<220> FEATURE:
<223> OTHER INFORMATION: CDR

<400> SEQUENCE: 81

Gly Thr Phe Ala Gly Gly Ser Tyr Tyr Gly
1               5                   10

<210> SEQ ID NO 82
<211> LENGTH: 10
<212> TYPE: PRT
<213> ORGANISM: Artificial
<220> FEATURE:
<223> OTHER INFORMATION: CDR

<400> SEQUENCE: 82

Gly Thr Phe Ala Gly Gly Ser Tyr Tyr Gly
1               5                   10

<210> SEQ ID NO 83
<211> LENGTH: 10
<212> TYPE: PRT
<213> ORGANISM: Artificial
<220> FEATURE:
<223> OTHER INFORMATION: CDR

<400> SEQUENCE: 83

Gly Thr Phe Ala Gly Gly Ser Tyr Tyr Gly
1               5                   10

<210> SEQ ID NO 84
<211> LENGTH: 10
<212> TYPE: PRT
```

```
<213> ORGANISM: Artificial
<220> FEATURE:
<223> OTHER INFORMATION: CDR

<400> SEQUENCE: 84

Gly Thr Phe Ala Gly Gly Ser Tyr Tyr Gly
1               5                   10

<210> SEQ ID NO 85
<211> LENGTH: 112
<212> TYPE: PRT
<213> ORGANISM: Artificial
<220> FEATURE:
<223> OTHER INFORMATION: VL

<400> SEQUENCE: 85

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ala Trp Thr Ser Lys
                85                  90                  95

Met Ala Gly Val Phe Gly Gly Gly Thr Lys Leu Thr Val Leu Gly Gln
            100                 105                 110

<210> SEQ ID NO 86
<211> LENGTH: 112
<212> TYPE: PRT
<213> ORGANISM: Artificial
<220> FEATURE:
<223> OTHER INFORMATION: VL

<400> SEQUENCE: 86

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Arg Met
                85                  90                  95

Gly His Pro Val Phe Gly Gly Gly Thr Lys Leu Thr Val Leu Gly Gln
            100                 105                 110

<210> SEQ ID NO 87
<211> LENGTH: 113
<212> TYPE: PRT
<213> ORGANISM: Artificial
<220> FEATURE:
<223> OTHER INFORMATION: VL

<400> SEQUENCE: 87
```

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Thr Tyr Gly Lys Gly
                85                  90                  95

Val Thr Pro Pro Val Phe Gly Gly Gly Thr Lys Leu Thr Val Leu Gly
            100                 105                 110

Gln

<210> SEQ ID NO 88
<211> LENGTH: 113
<212> TYPE: PRT
<213> ORGANISM: Artificial
<220> FEATURE:
<223> OTHER INFORMATION: VL

<400> SEQUENCE: 88

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 89
<211> LENGTH: 112
<212> TYPE: PRT
<213> ORGANISM: Artificial
<220> FEATURE:
<223> OTHER INFORMATION: VL

<400> SEQUENCE: 89

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
```

```
                 65                  70                  75                  80
Gln Ala Glu Asp Glu Ala Asp Tyr Tyr Cys Gln Ala Trp Thr Ser Lys
                 85                  90                  95

Met Ala Gly Val Phe Gly Gly Gly Thr Lys Leu Thr Val Leu Gly Gln
                100                 105                 110

<210> SEQ ID NO 90
<211> LENGTH: 112
<212> TYPE: PRT
<213> ORGANISM: Artificial
<220> FEATURE:
<223> OTHER INFORMATION: VL

<400> SEQUENCE: 90

Asp Ile Ala Leu Thr Gln Pro Ala Ser Val Ser Gly Ser Pro Gly Gln
1                 5                  10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
                35                  40                  45

Met Ile Tyr Gly Val Ser Lys Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ala Trp Thr Ser Lys
                85                  90                  95

Met Ala Gly Val Phe Gly Gly Gly Thr Lys Leu Thr Val Leu Gly Gln
                100                 105                 110

<210> SEQ ID NO 91
<211> LENGTH: 113
<212> TYPE: PRT
<213> ORGANISM: Artificial
<220> FEATURE:
<223> OTHER INFORMATION: VL

<400> SEQUENCE: 91

Asp Ile Ala Leu Thr Gln Pro Ala Ser Val Ser Gly Ser Pro Gly Gln
1                 5                  10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
                35                  40                  45

Met Ile Tyr Gly Val Ser Lys Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln

<210> SEQ ID NO 92
<211> LENGTH: 113
<212> TYPE: PRT
<213> ORGANISM: Artificial
<220> FEATURE:
<223> OTHER INFORMATION: VL
```

<400> SEQUENCE: 92

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln
```

<210> SEQ ID NO 93
<211> LENGTH: 113
<212> TYPE: PRT
<213> ORGANISM: Artificial
<220> FEATURE:
<223> OTHER INFORMATION: VL

<400> SEQUENCE: 93

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln
```

<210> SEQ ID NO 94
<211> LENGTH: 113
<212> TYPE: PRT
<213> ORGANISM: Artificial
<220> FEATURE:
<223> OTHER INFORMATION: VL

<400> SEQUENCE: 94

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln
```

<210> SEQ ID NO 95
<211> LENGTH: 113
<212> TYPE: PRT
<213> ORGANISM: Artificial
<220> FEATURE:
<223> OTHER INFORMATION: VL

<400> SEQUENCE: 95

```
Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30

Asn Tyr Val Asn Trp Tyr Gln Gln His Pro Gly Lys Ala Pro Lys Leu
             35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln
```

<210> SEQ ID NO 96
<211> LENGTH: 113
<212> TYPE: PRT
<213> ORGANISM: Artificial
<220> FEATURE:
<223> OTHER INFORMATION: VL

<400> SEQUENCE: 96

```
Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30

Asn Tyr Val Asn Trp Tyr Gln Gln His Pro Gly Lys Ala Pro Lys Leu
             35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln
```

<210> SEQ ID NO 97
<211> LENGTH: 113

```
<212> TYPE: PRT
<213> ORGANISM: Artificial
<220> FEATURE:
<223> OTHER INFORMATION: VL

<400> SEQUENCE: 97

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 98
<211> LENGTH: 113
<212> TYPE: PRT
<213> ORGANISM: Artificial
<220> FEATURE:
<223> OTHER INFORMATION: VL

<400> SEQUENCE: 98

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln

<210> SEQ ID NO 99
<211> LENGTH: 115
<212> TYPE: PRT
<213> ORGANISM: Artificial
<220> FEATURE:
<223> OTHER INFORMATION: VH

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
```

```
                    35                  40                  45
Gly Thr Ile Asn Pro Val Ser Gly Asn Thr Ser Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Gly Gly Trp Phe Asp Tyr Trp Gly Gln Gly Thr Leu Val Thr
                100                 105                 110
Val Ser Ser
        115

<210> SEQ ID NO 100
<211> LENGTH: 115
<212> TYPE: PRT
<213> ORGANISM: Artificial
<220> FEATURE:
<223> OTHER INFORMATION: VH

<400> SEQUENCE: 100

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Ser
                20                  25                  30
Tyr Ile Asn Trp Val Arg Gln Ala Pro Gly Gln Gly Leu Glu Trp Met
            35                  40                  45
Gly Thr Ile Asn Pro Val Ser Gly Asn Thr Ser Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Gly Gly Trp Phe Asp Tyr Trp Gly Gln Gly Thr Leu Val Thr
                100                 105                 110
Val Ser Ser
        115

<210> SEQ ID NO 101
<211> LENGTH: 115
<212> TYPE: PRT
<213> ORGANISM: Artificial
<220> FEATURE:
<223> OTHER INFORMATION: VH

<400> SEQUENCE: 101

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Ser
                20                  25                  30
Tyr Ile Asn Trp Val Arg Gln Ala Pro Gly Gln Gly Leu Glu Trp Met
            35                  40                  45
Gly Thr Ile Asn Pro Val Ser Gly Asn Thr Ser Tyr Ala Gln Lys Phe
        50                  55                  60
Gln Gly Arg Val Thr Met Thr Arg Asp Thr Ser Ile Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Gly Gly Trp Phe Asp Tyr Trp Gly Gln Gly Thr Leu Val Thr
```

-continued

Val Ser Ser
       115

<210> SEQ ID NO 102
<211> LENGTH: 115
<212> TYPE: PRT
<213> ORGANISM: Artificial
<220> FEATURE:
<223> OTHER INFORMATION: VH

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Asn Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
       115

<210> SEQ ID NO 103
<211> LENGTH: 115
<212> TYPE: PRT
<213> ORGANISM: Artificial
<220> FEATURE:
<223> OTHER INFORMATION: VH

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Met Ile Asn Ala Pro Ile Gly Thr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
       115

<210> SEQ ID NO 104
<211> LENGTH: 115
<212> TYPE: PRT
<213> ORGANISM: Artificial
<220> FEATURE:
<223> OTHER INFORMATION: VH -continued

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gln Ile Asn Ala Ala Ser Gly Met Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 105
<211> LENGTH: 115
<212> TYPE: PRT
<213> ORGANISM: Artificial
<220> FEATURE:
<223> OTHER INFORMATION: VH

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Met Ile Asn Ala Pro Ile Gly Thr Thr Arg Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 106
<211> LENGTH: 115
<212> TYPE: PRT
<213> ORGANISM: Artificial
<220> FEATURE:
<223> OTHER INFORMATION: VH

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Asn Thr Arg Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
                100                 105                 110

Val Ser Ser
        115

<210> SEQ ID NO 107
<211> LENGTH: 115
<212> TYPE: PRT
<213> ORGANISM: Artificial
<220> FEATURE:
<223> OTHER INFORMATION: VH

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Thr Ile Asn Pro Val Ser Gly Ser Thr Ser Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
                100                 105                 110

Val Ser Ser
        115

<210> SEQ ID NO 108
<211> LENGTH: 115
<212> TYPE: PRT
<213> ORGANISM: Artificial
<220> FEATURE:
<223> OTHER INFORMATION: VH

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Gln Ile Asn Ala Ala Ser Gly Met Thr Arg Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
                100                 105                 110

Val Ser Ser
        115

<210> SEQ ID NO 109
<211> LENGTH: 115
<212> TYPE: PRT
<213> ORGANISM: Artificial
<220> FEATURE:
<223> OTHER INFORMATION: VH

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Asn Ile Asn Ala Ala Gly Ile Thr Leu Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 110
<211> LENGTH: 115
<212> TYPE: PRT
<213> ORGANISM: Artificial
<220> FEATURE:
<223> OTHER INFORMATION: VH

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Thr Ile Asn Pro Pro Thr Gly Gly Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 111
<211> LENGTH: 115
<212> TYPE: PRT
<213> ORGANISM: Artificial
<220> FEATURE:
<223> OTHER INFORMATION: VH

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Pro Ala Gly Thr Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 112
<211> LENGTH: 115
<212> TYPE: PRT
<213> ORGANISM: Artificial
<220> FEATURE:
<223> OTHER INFORMATION: VH

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Pro Ala Thr Gly His Ala Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 113
<211> LENGTH: 336
<212> TYPE: DNA
<213> ORGANISM: Artificial
<220> FEATURE:
<223> OTHER INFORMATION: VL

<400> SEQUENCE: 113
gatatcgcac tgacccagcc agcttcagtg agcggctcac caggtcagag cattaccatc       60
tcgtgtacgg gtactagcag cgatgttggt tcttataatt atgtgaattg gtaccagcag      120
catcccggga aggcgccgaa acttatgatt tatggtgttt ctaagcgtcc ctcaggcgtg      180
agcaaccgtt ttagcggatc caaaagcggc aacaccgcga gcctgaccat tagcggcctg      240
caagcggaag acgaagcgga ttattattgc caggcttgga cttctaagat ggctggtgtg      300
tttggcggcg gcacgaagtt aaccgttctt ggccag                                336

<210> SEQ ID NO 114
<211> LENGTH: 336
<212> TYPE: DNA
<213> ORGANISM: Artificial
<220> FEATURE:
<223> OTHER INFORMATION: VL

<400> SEQUENCE: 114
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc tcttcttata ctcgtatggg tcatcctgtg     300
tttggcggcg gcacgaagtt aaccgttctt ggccag                               336

<210> SEQ ID NO 115
<211> LENGTH: 339
<212> TYPE: DNA
<213> ORGANISM: Artificial
<220> FEATURE:
<223> OTHER INFORMATION: VL

<400> SEQUENCE: 115
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc gctacttatg gtaagggtgt tactcctcct     300
gtgtttggcg gcggcacgaa gttaaccgtt cttggccag                            339

<210> SEQ ID NO 116
<211> LENGTH: 339
<212> TYPE: DNA
<213> ORGANISM: Artificial
<220> FEATURE:
<223> OTHER INFORMATION: VL

<400> SEQUENCE: 116
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtt cttggccag                            339

<210> SEQ ID NO 117
<211> LENGTH: 336
<212> TYPE: DNA
<213> ORGANISM: Artificial
<220> FEATURE:
<223> OTHER INFORMATION: VL

<400> SEQUENCE: 117
gatatcgcac tgacccagcc agcttcagtg agcggctcac caggtcagag cattaccatc      60
tcgtgtacgg gtactagcag cgatgttggt tcttataatt atgtgaattg gtaccagcag     120

```
catcccggga aggcgccgaa acttatgatt tatggtgttt ctaagcgtcc ctcaggcgtg    180
agcaaccgtt ttagcggatc caaaagcggc aacaccgcga gcctgaccat tagcggcctg    240
caagcggaag acgaagcgga ttattattgc caggcttgga cttctaagat ggctggtgtg    300
tttggcggcg gcacgaagtt aaccgttctt ggccag                              336
```

<210> SEQ ID NO 118
<211> LENGTH: 336
<212> TYPE: DNA
<213> ORGANISM: Artificial
<220> FEATURE:
<223> OTHER INFORMATION: VL

<400> SEQUENCE: 118

```
gatatcgcac tgacccagcc agcttcagtg agcggctcac caggtcagag cattaccatc    60
tcgtgtacgg gtactagcag cgatgttggt tcttataatt atgtgaattg gtaccagcag    120
catcccggga aggcgccgaa acttatgatt tatggtgttt ctaagcgtcc ctcaggcgtg    180
agcaaccgtt ttagcggatc caaaagcggc aacaccgcga gcctgaccat tagcggcctg    240
caagcggaag acgaagcgga ttattattgc caggcttgga cttctaagat ggctggtgtg    300
tttggcggcg gcacgaagtt aaccgttctt ggccag                              336
```

<210> SEQ ID NO 119
<211> LENGTH: 339
<212> TYPE: DNA
<213> ORGANISM: Artificial
<220> FEATURE:
<223> OTHER INFORMATION: VL

<400> SEQUENCE: 119

```
gatatcgcac tgacccagcc agcttcagtg agcggctcac caggtcagag cattaccatc    60
tcgtgtacgg gtactagcag cgatgttggt tcttataatt atgtgaattg gtaccagcag    120
catcccggga aggcgccgaa acttatgatt tatggtgttt ctaagcgtcc ctcaggcgtg    180
agcaaccgtt ttagcggatc caaaagcggc aacaccgcga gcctgaccat tagcggcctg    240
caagcggaag acgaagcgga ttattattgc ggtacttttg ctggtggttc ttattatggt    300
gtgtttggcg gcggcacgaa gttaaccgtt cttggccag                           339
```

<210> SEQ ID NO 120
<211> LENGTH: 339
<212> TYPE: DNA
<213> ORGANISM: Artificial
<220> FEATURE:
<223> OTHER INFORMATION: VL

<400> SEQUENCE: 120

```
gatatcgcac tgacccagcc agcttcagtg agcggctcac caggtcagag cattaccatc    60
tcgtgtacgg gtactagcag cgatgttggt tcttataatt atgtgaattg gtaccagcag    120
catcccggga aggcgccgaa acttatgatt tatggtgttt ctaagcgtcc ctcaggcgtg    180
agcaaccgtt ttagcggatc caaaagcggc aacaccgcga gcctgaccat tagcggcctg    240
caagcggaag acgaagcgga ttattattgc ggtacttttg ctggtggttc ttattatggt    300
gtgtttggcg gcggcacgaa gttaaccgtt cttggccag                           339
```

<210> SEQ ID NO 121
<211> LENGTH: 339
<212> TYPE: DNA
<213> ORGANISM: Artificial

```
<220> FEATURE:
<223> OTHER INFORMATION: VL

<400> SEQUENCE: 121
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtt cttggccag                            339

<210> SEQ ID NO 122
<211> LENGTH: 339
<212> TYPE: DNA
<213> ORGANISM: Artificial
<220> FEATURE:
<223> OTHER INFORMATION: VL

<400> SEQUENCE: 122
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtt cttggccag                            339

<210> SEQ ID NO 123
<211> LENGTH: 339
<212> TYPE: DNA
<213> ORGANISM: Artificial
<220> FEATURE:
<223> OTHER INFORMATION: VL

<400> SEQUENCE: 123
gatatcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtt cttggccag                            339

<210> SEQ ID NO 124
<211> LENGTH: 339
<212> TYPE: DNA
<213> ORGANISM: Artificial
<220> FEATURE:
<223> OTHER INFORMATION: VL

<400> SEQUENCE: 124
gatatcgcac tgacccagcc agcttcagtg agcggctcac caggtcagag cattaccatc      60
tcgtgtactg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
```

```
gtgtttggcg gcggcacgaa gttaaccgtt cttggccag                      339

<210> SEQ ID NO 125
<211> LENGTH: 339
<212> TYPE: DNA
<213> ORGANISM: Artificial
<220> FEATURE:
<223> OTHER INFORMATION: VL

<400> SEQUENCE: 125
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339

<210> SEQ ID NO 126
<211> LENGTH: 339
<212> TYPE: DNA
<213> ORGANISM: Artificial
<220> FEATURE:
<223> OTHER INFORMATION: VL

<400> SEQUENCE: 126
gatatcgcac tgacccagcc agcttcagtg agcggctcac caggtcagag cattaccatc    60
tcgtgtacgg gtactagcag cgatgttggt tcttataatt atgtgaattg gtaccagcag   120
catcccggga aggcgccgaa acttatgatt tatggtgttt ctaagcgtcc ctcaggcgtg   180
agcaaccgtt ttagcggatc caaaagcggc aacaccgcga gcctgaccat tagcggcctg   240
caagcggaag acgaagcgga ttattattgc ggtacttttg ctggtggttc ttattatggt   300
gtgtttggcg gcggcacgaa gttaaccgtt cttggccag                          339

<210> SEQ ID NO 127
<211> LENGTH: 345
<212> TYPE: DNA
<213> ORGANISM: Artificial
<220> FEATURE:
<223> OTHER INFORMATION: VH

<400> SEQUENCE: 127
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcact atcaatccgg tttctggcaa tacgtcttac   180
gcgcagaagt tcagggccg gtgaccatg acccgtgata ccagcattag caccgcgtat    240
atggaactga gcagcctgcg tagcgaagat acggccgtgt attattgcgc gcgtggtggt   300
tggtttgatt attggggcca aggcacccctg gtgacggtta gctca                 345

<210> SEQ ID NO 128
<211> LENGTH: 345
<212> TYPE: DNA
<213> ORGANISM: Artificial
<220> FEATURE:
<223> OTHER INFORMATION: VH

<400> SEQUENCE: 128
caggtgcaat tggttcagag cggcgcggaa gtgaaaaaac cgggcgcgag cgtgaaagtg    60
```

```
agctgcaaag cctccggata tacctttact tcttcttata ttaattgggt ccgccaagcc    120
cctgggcagg gtctcgagtg gatgggcact atcaatccgg tttctggcaa tacgtcttac    180
gcgcagaagt tcagggccg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 129
<211> LENGTH: 345
<212> TYPE: DNA
<213> ORGANISM: Artificial
<220> FEATURE:
<223> OTHER INFORMATION: VH

<400> SEQUENCE: 129
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcact atcaatccgg tttctggcaa tacgtcttac    180
gcgcagaagt tcagggccg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 130
<211> LENGTH: 345
<212> TYPE: DNA
<213> ORGANISM: Artificial
<220> FEATURE:
<223> OTHER INFORMATION: VH

<400> SEQUENCE: 130
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcact atcaatccgg tttctggcaa tacgtcttac    180
gcgcagaagt tcagggccg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 131
<211> LENGTH: 345
<212> TYPE: DNA
<213> ORGANISM: Artificial
<220> FEATURE:
<223> OTHER INFORMATION: VH

<400> SEQUENCE: 131
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcatg attaatgctc ctattggtac tactcgttat    180
gctcagaagt tcagggtcg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 132
<211> LENGTH: 345
```

```
<212> TYPE: DNA
<213> ORGANISM: Artificial
<220> FEATURE:
<223> OTHER INFORMATION: VH

<400> SEQUENCE: 132
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggccag attaatgctg cttctggtat gactcgttat    180
gctcagaagt ttcagggtcg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 133
<211> LENGTH: 345
<212> TYPE: DNA
<213> ORGANISM: Artificial
<220> FEATURE:
<223> OTHER INFORMATION: VH

<400> SEQUENCE: 133
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcatg attaatgctc ctattggtac tactcgttat    180
gctcagaagt ttcagggtcg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 134
<211> LENGTH: 345
<212> TYPE: DNA
<213> ORGANISM: Artificial
<220> FEATURE:
<223> OTHER INFORMATION: VH

<400> SEQUENCE: 134
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcact atcaatccgg tttctggcaa tacgcgttac    180
gcgcagaagt ttcagggccg ggtgaccatg acccgtgata ccagcattag caccgcgtat    240
atggaactga gcagcctgcg tagcgaagat acggccgtgt attattgcgc gcgtggtggt    300
tggtttgatt attggggcca aggcaccctg gtgacggtta gctca                   345

<210> SEQ ID NO 135
<211> LENGTH: 345
<212> TYPE: DNA
<213> ORGANISM: Artificial
<220> FEATURE:
<223> OTHER INFORMATION: VH

<400> SEQUENCE: 135
caggtgcaat tggttcagag cggcgcggaa gtgaaaaaac cgggcgcgag cgtgaaagtg     60
agctgcaaag cctccggata tacctttact tcttcttata ttaattgggt ccgccaagcc    120
cctgggcagg gtctcgagtg gatgggcact atcaatccgg tttctggctc tacgtcttac    180
gcgcagaagt ttcagggccg ggtgaccatg acccgtgata ccagcattag caccgcgtat    240
```

```
atggaactga gcagcctgcg tagcgaagat acggccgtgt attattgcgc gcgtggtggt    300
tggtttgatt attggggcca aggcaccctg gtgacggtta gctca                    345
```

<210> SEQ ID NO 136
<211> LENGTH: 345
<212> TYPE: DNA
<213> ORGANISM: Artificial
<220> FEATURE:
<223> OTHER INFORMATION: VH

<400> SEQUENCE: 136

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggccag attaatgctg cttctggtat gactcgttat   180
gctcagaagt ttcagggtcg ggtcaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                   345
```

<210> SEQ ID NO 137
<211> LENGTH: 345
<212> TYPE: DNA
<213> ORGANISM: Artificial
<220> FEATURE:
<223> OTHER INFORMATION: VH

<400> SEQUENCE: 137

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcaat attaatgctg ctgctggtat tactctttat   180
gctcagaagt ttcagggtcg ggtcaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                   345
```

<210> SEQ ID NO 138
<211> LENGTH: 345
<212> TYPE: DNA
<213> ORGANISM: Artificial
<220> FEATURE:
<223> OTHER INFORMATION: VH

<400> SEQUENCE: 138

```
caggtgcaat tggttcagag cggcgcggaa gtgaaaaaac cgggcgcgag cgtgaaagtg    60
agctgcaaag cctccggata tacctttact tcttcttata ttaattgggt ccgccaagcc   120
cctgggcagg gtctcgagtg gatgggcact attaatcctc ctactggagg tacttattat   180
gctcagaagt ttcagggtcg ggtgaccatg acccgtgata ccagcattag caccgcgtat   240
atggaactga gcagcctgcg tagcgaagat acggccgtgt attattgcgc gcgtggtggt   300
tggtttgatt attggggcca aggcaccctg gtgacggtta gctca                   345
```

<210> SEQ ID NO 139
<211> LENGTH: 345
<212> TYPE: DNA
<213> ORGANISM: Artificial
<220> FEATURE:
<223> OTHER INFORMATION: VH

<400> SEQUENCE: 139

```
caggtgcaat tggttcagag cggcgcggaa gtgaaaaaac cgggcgcgag cgtgaaagtg      60
agctgcaaag cctccggata tacctttact tcttcttata ttaattgggt ccgccaagcc     120
cctgggcagg gtctcgagtg gatgggcggt attaatcctc ctgctggtac tacttcttat     180
gctcagaagt ttcagggtcg ggtcaccatg acccgtgata ccagcattag caccgcgtat     240
atggaactga gcagcctgcg tagcgaagat acggccgtgt attattgcgc gcgtggtggt     300
tggtttgatt attggggcca aggcaccctg gtgacggtta gctca                    345

<210> SEQ ID NO 140
<211> LENGTH: 345
<212> TYPE: DNA
<213> ORGANISM: Artificial
<220> FEATURE:
<223> OTHER INFORMATION: VH

<400> SEQUENCE: 140
caggtgcaat tggttcagag cggcgcggaa gtgaaaaaac cgggcgcgag cgtgaaagtg      60
agctgcaaag cctccggata tacctttact tcttcttata ttaattgggt ccgccaagcc     120
cctgggcagg gtctcgagtg gatgggcaat attaatcctg ctactggtca tgctgattat     180
gctcagaagt ttcagggtcg ggtgaccatg acccgtgata ccagcattag caccgcgtat     240
atggaactga gcagcctgcg tagcgaagat acggccgtgt attattgcgc gcgtggtggt     300
tggtttgatt attggggcca aggcaccctg gtgacggtta gctca                    345

<210> SEQ ID NO 141
<211> LENGTH: 217
<212> TYPE: PRT
<213> ORGANISM: Artificial
<220> FEATURE:
<223> OTHER INFORMATION: light chain

<400> SEQUENCE: 141

Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 142
<211> LENGTH: 217
<212> TYPE: PRT
<213> ORGANISM: Artificial
<220> FEATURE:
<223> OTHER INFORMATION: light chain

<400> SEQUENCE: 142

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 143
<211> LENGTH: 217
<212> TYPE: PRT
<213> ORGANISM: Artificial
<220> FEATURE:
<223> OTHER INFORMATION: light chain

<400> SEQUENCE: 143

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 144
<211> LENGTH: 217
<212> TYPE: PRT
<213> ORGANISM: Artificial
<220> FEATURE:
<223> OTHER INFORMATION: light chain

<400> SEQUENCE: 144

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Ser Tyr
                 20                  25                  30

Asn Tyr Val Asn Trp Tyr Gln Gln His Pro Gly Lys Ala Pro Lys Leu
             35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
                 85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205
```

```
Lys Thr Val Ala Pro Thr Glu Cys Ser
    210                 215

<210> SEQ ID NO 145
<211> LENGTH: 217
<212> TYPE: PRT
<213> ORGANISM: Artificial
<220> FEATURE:
<223> OTHER INFORMATION: light chain

<400> SEQUENCE: 145

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 146
<211> LENGTH: 445
<212> TYPE: PRT
<213> ORGANISM: Artificial
<220> FEATURE:
<223> OTHER INFORMATION: heavy chain

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Arg Leu Arg Ser Asp Asp Thr Ala Val Tyr Tyr Cys
             85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 147
<211> LENGTH: 445
<212> TYPE: PRT
<213> ORGANISM: Artificial
<220> FEATURE:
<223> OTHER INFORMATION: heavy chain

<400> SEQUENCE: 147

Gln Val Gln Leu Val Gln Ser Gly Ala Glu Val Lys Lys Pro Gly Ala
```

-continued

```
1               5               10              15
Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
                35                  40                  45

Gly Gln Ile Asn Ala Ala Ser Gly Met Thr Arg Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
                115                 120                 125

Ser Ser Lys Ser Thr Ser Gly Gly Thr Ala Ala Leu Gly Cys Leu Val
                130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205

Val Asp Lys Arg Val Glu Pro Lys Ser Cys Asp Lys Thr His Thr Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
                275                 280                 285

Pro Arg Glu Glu Gln Tyr Asn Ser Thr Tyr Arg Val Val Ser Val Leu
                290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430
```

His Tyr Thr Gln Lys Ser Leu Ser Leu Ser Pro Gly Lys
            435                 440                 445

<210> SEQ ID NO 148
<211> LENGTH: 445
<212> TYPE: PRT
<213> ORGANISM: Artificial
<220> FEATURE:
<223> OTHER INFORMATION: heavy chain

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Ala Ala Gly Ile Thr Leu Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys

```
                         355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 149
<211> LENGTH: 445
<212> TYPE: PRT
<213> ORGANISM: Artificial
<220> FEATURE:
<223> OTHER INFORMATION: heavy chain

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Pro Ala Gly Thr Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445
```

<210> SEQ ID NO 150
<211> LENGTH: 445
<212> TYPE: PRT
<213> ORGANISM: Artificial
<220> FEATURE:
<223> OTHER INFORMATION: heavy chain

<400> SEQUENCE: 150

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Asn Ile Asn Pro Ala Thr Gly His Ala Asp Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
                195                 200                 205
```

-continued

Val Asp Lys Arg Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 151
<211> LENGTH: 217
<212> TYPE: PRT
<213> ORGANISM: Artificial
<220> FEATURE:
<223> OTHER INFORMATION: light chain

<400> SEQUENCE: 151

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe

```
              130                 135                 140
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 152
<211> LENGTH: 217
<212> TYPE: PRT
<213> ORGANISM: Artificial
<220> FEATURE:
<223> OTHER INFORMATION: light chain

<400> SEQUENCE: 152

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
                20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 153
<211> LENGTH: 217
<212> TYPE: PRT
<213> ORGANISM: Artificial
<220> FEATURE:
<223> OTHER INFORMATION: light chain

<400> SEQUENCE: 153

Gln Ser Ala Leu Thr Gln Pro Ala Ser Val Ser Gly Ser Pro Gly Gln
```

```
1               5                   10                  15
Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
            85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
            165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215

<210> SEQ ID NO 154
<211> LENGTH: 217
<212> TYPE: PRT
<213> ORGANISM: Artificial
<220> FEATURE:
<223> OTHER INFORMATION: light chain

<400> SEQUENCE: 154

Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
            35                  40                  45

Met Ile Tyr Gly Val Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gly Thr Phe Ala Gly Gly
            85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
            130                 135                 140

Tyr Pro Gly Ala Val Thr Val Ala Trp Lys Ala Asp Ser Ser Pro Val
145                 150                 155                 160
```

```
Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 155
<211> LENGTH: 217
<212> TYPE: PRT
<213> ORGANISM: Artificial
<220> FEATURE:
<223> OTHER INFORMATION: light chain

<400> SEQUENCE: 155

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Tyr Val Asn Trp Tyr Gln Gln His Pro Gly Lys Ala Pro Lys Leu
        35                  40                  45

Met Ile Tyr Gly Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Thr Phe Ala Gly Gly
                85                  90                  95

Ser Tyr Tyr Gly Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 156
<211> LENGTH: 441
<212> TYPE: PRT
<213> ORGANISM: Artificial
<220> FEATURE:
<223> OTHER INFORMATION: heavy chain

<400> SEQUENCE: 156

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30
```

-continued

```
Tyr Ile Asn Trp Val Arg Gln Ala Pro Gly Gln Gly Leu Glu Trp Met
    35                  40                  45
Gly Thr Ile Asn Pro Val Ser Gly Ser Thr Ser Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Ala Arg Gly Gly Trp Phe Asp Tyr Trp Gly Gln Gly Thr Leu Val Thr
            100                 105                 110
Val Ser Ser Ala Ser Thr Lys Gly Pro Ser Val Phe Pro Leu Ala Pro
        115                 120                 125
Cys Ser Arg Ser Thr Ser Glu Ser Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Asn Phe Gly
            180                 185                 190
Thr Gln Thr Tyr Thr Cys Asn Val Asp His Lys Pro Ser Asn Thr Lys
        195                 200                 205
Val Asp Lys Thr Val Glu Arg Lys Cys Cys Val Glu Cys Pro Pro Cys
    210                 215                 220
Pro Ala Pro Pro Val Ala Gly Pro Ser Val Phe Leu Phe Pro Pro Lys
225                 230                 235                 240
Pro Lys Asp Thr Leu Met Ile Ser Arg Thr Pro Glu Val Thr Cys Val
                245                 250                 255
Val Val Asp Val Ser His Glu Asp Pro Glu Val Gln Phe Asn Trp Tyr
            260                 265                 270
Val Asp Gly Val Glu Val His Asn Ala Lys Thr Lys Pro Arg Glu Glu
        275                 280                 285
Gln Phe Asn Ser Thr Phe Arg Val Val Ser Val Leu Thr Val Val His
    290                 295                 300
Gln Asp Trp Leu Asn Gly Lys Glu Tyr Lys Cys Lys Val Ser Asn Lys
305                 310                 315                 320
Gly Leu Pro Ala Pro Ile Glu Lys Thr Ile Ser Lys Thr Lys Gly Gln
                325                 330                 335
Pro Arg Glu Pro Gln Val Tyr Thr Leu Pro Pro Ser Arg Glu Glu Met
            340                 345                 350
Thr Lys Asn Gln Val Ser Leu Thr Cys Leu Val Lys Gly Phe Tyr Pro
        355                 360                 365
Ser Asp Ile Ala Val Glu Trp Glu Ser Asn Gly Gln Pro Glu Asn Asn
    370                 375                 380
Tyr Lys Thr Thr Pro Pro Met Leu Asp Ser Asp Gly Ser Phe Phe Leu
385                 390                 395                 400
Tyr Ser Lys Leu Thr Val Asp Lys Ser Arg Trp Gln Gln Gly Asn Val
                405                 410                 415
Phe Ser Cys Ser Val Met His Glu Ala Leu His Asn His Tyr Thr Gln
            420                 425                 430
Lys Ser Leu Ser Leu Ser Pro Gly Lys
        435                 440
```

-continued

```
<210> SEQ ID NO 157
<211> LENGTH: 441
<212> TYPE: PRT
<213> ORGANISM: Artificial
<220> FEATURE:
<223> OTHER INFORMATION: heavy chain

<400> SEQUENCE: 157
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Ser |
| | | | 20 | | | | | 25 | | | | | 30 | | |
| Tyr | Ile | Asn | Trp | Val | Arg | Gln | Ala | Pro | Gly | Gln | Gly | Leu | Glu | Trp | Met |
| | | 35 | | | | | 40 | | | | | 45 | | | |
| Gly | Gln | Ile | Asn | Ala | Ala | Ser | Gly | Met | Thr | Arg | Tyr | Ala | Gln | Lys | Phe |
| 50 | | | | | 55 | | | | | 60 | | | | | |
| Gln | Gly | Arg | Val | Thr | Met | Thr | Arg | Asp | Thr | Ser | Ile | Ser | Thr | Ala | Tyr |
| 65 | | | | 70 | | | | | 75 | | | | | 80 | |
| Met | Glu | Leu | Ser | Arg | Leu | Arg | Ser | Asp | Asp | Thr | Ala | Val | Tyr | Tyr | Cys |
| | | | 85 | | | | | 90 | | | | | 95 | | |
| Ala | Arg | Gly | Gly | Trp | Phe | Asp | Tyr | Trp | Gly | Gln | Gly | Thr | Leu | Val | Thr |
| | | 100 | | | | | 105 | | | | | 110 | | | |
| Val | Ser | Ser | Ala | Ser | Thr | Lys | Gly | Pro | Ser | Val | Phe | Pro | Leu | Ala | Pro |
| | | 115 | | | | | 120 | | | | | 125 | | | |
| Cys | Ser | Arg | Ser | Thr | Ser | Glu | Ser | Thr | Ala | Ala | Leu | Gly | Cys | Leu | Val |
| 130 | | | | | 135 | | | | | 140 | | | | | |
| Lys | Asp | Tyr | Phe | Pro | Glu | Pro | Val | Thr | Val | Ser | Trp | Asn | Ser | Gly | Ala |
| 145 | | | | 150 | | | | | 155 | | | | | 160 | |
| Leu | Thr | Ser | Gly | Val | His | Thr | Phe | Pro | Ala | Val | Leu | Gln | Ser | Ser | Gly |
| | | | | 165 | | | | | 170 | | | | | 175 | |
| Leu | Tyr | Ser | Leu | Ser | Ser | Val | Val | Thr | Val | Pro | Ser | Ser | Asn | Phe | Gly |
| | | | 180 | | | | | 185 | | | | | 190 | | |
| Thr | Gln | Thr | Tyr | Thr | Cys | Asn | Val | Asp | His | Lys | Pro | Ser | Asn | Thr | Lys |
| | | 195 | | | | | 200 | | | | | 205 | | | |
| Val | Asp | Lys | Thr | Val | Glu | Arg | Lys | Cys | Cys | Val | Glu | Cys | Pro | Pro | Cys |
| 210 | | | | | 215 | | | | | 220 | | | | | |
| Pro | Ala | Pro | Pro | Val | Ala | Gly | Pro | Ser | Val | Phe | Leu | Phe | Pro | Pro | Lys |
| 225 | | | | 230 | | | | | 235 | | | | | 240 | |
| Pro | Lys | Asp | Thr | Leu | Met | Ile | Ser | Arg | Thr | Pro | Glu | Val | Thr | Cys | Val |
| | | | | 245 | | | | | 250 | | | | | 255 | |
| Val | Val | Asp | Val | Ser | His | Glu | Asp | Pro | Glu | Val | Gln | Phe | Asn | Trp | Tyr |
| | | | 260 | | | | | 265 | | | | | 270 | | |
| Val | Asp | Gly | Val | Glu | Val | His | Asn | Ala | Lys | Thr | Lys | Pro | Arg | Glu | Glu |
| | | 275 | | | | | 280 | | | | | 285 | | | |
| Gln | Phe | Asn | Ser | Thr | Phe | Arg | Val | Val | Ser | Val | Leu | Thr | Val | Val | His |
| | 290 | | | | | 295 | | | | | 300 | | | | |
| Gln | Asp | Trp | Leu | Asn | Gly | Lys | Glu | Tyr | Lys | Cys | Lys | Val | Ser | Asn | Lys |
| 305 | | | | | 310 | | | | | 315 | | | | | 320 |
| Gly | Leu | Pro | Ala | Pro | Ile | Glu | Lys | Thr | Ile | Ser | Lys | Thr | Lys | Gly | Gln |
| | | | | 325 | | | | | 330 | | | | | 335 | |
| Pro | Arg | Glu | Pro | Gln | Val | Tyr | Thr | Leu | Pro | Pro | Ser | Arg | Glu | Glu | Met |
| | | | 340 | | | | | 345 | | | | | 350 | | |
| Thr | Lys | Asn | Gln | Val | Ser | Leu | Thr | Cys | Leu | Val | Lys | Gly | Phe | Tyr | Pro |
| | | 355 | | | | | 360 | | | | | 365 | | | |
| Ser | Asp | Ile | Ala | Val | Glu | Trp | Glu | Ser | Asn | Gly | Gln | Pro | Glu | Asn | Asn |
| | | 370 | | | | | 375 | | | | | 380 | | | |

```
Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 158
<211> LENGTH: 441
<212> TYPE: PRT
<213> ORGANISM: Artificial
<220> FEATURE:
<223> OTHER INFORMATION: heavy chain

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Asn Ile Asn Ala Ala Gly Ile Thr Leu Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300
```

```
Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 159
<211> LENGTH: 441
<212> TYPE: PRT
<213> ORGANISM: Artificial
<220> FEATURE:
<223> OTHER INFORMATION: heavy chain

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Gly Ile Asn Pro Pro Ala Gly Thr Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
```

```
                225                 230                 235                 240
Pro Lys Asp Thr Leu Met Ile Ser Arg Thr Pro Glu Val Thr Cys Val
                    245                 250                 255

Val Val Asp Val Ser His Glu Asp Pro Glu Val Gln Phe Asn Trp Tyr
                260                 265                 270

Val Asp Gly Val Glu Val His Asn Ala Lys Thr Lys Pro Arg Glu Glu
            275                 280                 285

Gln Phe Asn Ser Thr Phe Arg Val Val Ser Val Leu Thr Val Val His
        290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
                340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
        370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
                420                 425                 430

Lys Ser Leu Ser Leu Ser Pro Gly Lys
            435                 440

<210> SEQ ID NO 160
<211> LENGTH: 441
<212> TYPE: PRT
<213> ORGANISM: Artificial
<220> FEATURE:
<223> OTHER INFORMATION: heavy chain

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30

Tyr Ile Asn Trp Val Arg Gln Ala Pro Gly Gln Gly Leu Glu Trp Met
            35                  40                  45

Gly Asn Ile Asn Pro Ala Thr Gly His Ala Asp Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160
```

```
Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 161
<211> LENGTH: 651
<212> TYPE: DNA
<213> ORGANISM: Artificial
<220> FEATURE:
<223> OTHER INFORMATION: light chain

<400> SEQUENCE: 161

| | | | | | | |
|---|---|---|---|---|---|---|
| cagagcgccc | tgacccagcc | cgccagcgtg | tccggcagcc | caggccagtc | tatcacaatc | 60 |
| agctgcaccg | gcacctccag | cgacgtgggc | agctacaact | acgtgaactg | gtatcagcag | 120 |
| caccccggca | aggcccccaa | gctgatgatc | tacggcgtga | gcaagaggcc | cagcggcgtg | 180 |
| tccaacaggt | tcagcggcag | caagagcggc | aacaccgcca | gcctgacaat | cagtgggctg | 240 |
| caggctgagg | acgaggccga | ctactactgc | ggcacctttg | ccggcggatc | atactacggc | 300 |
| gtgttcggcg | agggaccaa | gctgaccgtg | ctgggccagc | ctaaggctgc | ccccagcgtg | 360 |
| accctgttcc | cccccagcag | cgaggagctg | caggccaaca | aggccaccct | ggtgtgcctg | 420 |
| atcagcgact | tctacccagg | cgccgtgacc | gtggcctgga | aggccgacag | cagccccgtg | 480 |

```
aaggccggcg tggagaccac caccccagc aagcagagca acaacaagta cgccgccagc    540
agctacctga gcctgacccc cgagcagtgg aagagccaca ggtcctacag ctgccaggtg    600
acccacgagg gcagcaccgt ggaaaagacc gtggccccaa ccgagtgcag c             651
```

<210> SEQ ID NO 162  
<211> LENGTH: 651  
<212> TYPE: DNA  
<213> ORGANISM: Artificial  
<220> FEATURE:  
<223> OTHER INFORMATION: light chain

<400> SEQUENCE: 162

```
cagagcgccc tgacccagcc cgccagcgtg tccggcagcc caggccagtc tatcacaatc    60
agctgcaccg gcacctccag cgacgtgggc agctacaact acgtgaactg gtatcagcag    120
caccccggca aggcccccaa gctgatgatc tacggcgtga gcaagaggcc cagcggcgtg    180
tccaacaggt tcagcggcag caagagcggc aacaccgcca gcctgacaat cagtgggctg    240
caggctgagg acgaggccga ctactactgc ggcacctttg ccggcggatc atactacggc    300
gtgttcggcg gagggaccaa gctgaccgtg ctgggccagc ctaaggctgc ccccagcgtg    360
accctgttcc cccccagcag cgaggagctg caggccaaca aggccaccct ggtgtgcctg    420
atcagcgact ctacccagg cgccgtgacc gtggcctgga aggccgacag cagcccgtg    480 aaggccggcg tggagaccac caccccagc aagcagagca acaacaagta cgccgccagc    540
agctacctga gcctgacccc cgagcagtgg aagagccaca ggtcctacag ctgccaggtg    600
acccacgagg gcagcaccgt ggaaaagacc gtggccccaa ccgagtgcag c             651
```

<210> SEQ ID NO 163  
<211> LENGTH: 651  
<212> TYPE: DNA  
<213> ORGANISM: Artificial  
<220> FEATURE:  
<223> OTHER INFORMATION: light chain

<400> SEQUENCE: 163

```
cagagcgcac tgacccagcc agcttcagtg agcggctcac aggtcagag cattaccatc     60 tcgtgtacgg gtactagcag cgatgttggt tcttataatt atgtgaattg gtaccagcag    120
catcccggga aggcgccgaa acttatgatt tatggtgttt ctaagcgtcc ctcaggcgtg    180
agcaaccgtt ttagcggatc caaaagcggc aacaccgcga gcctgaccat tagcggcctg    240
caagcggaag acgaagcgga ttattattgc ggtactttg ctggtggttc ttattatggt    300
gtgtttggcg gcggcacgaa gttaaccgtc ctaggtcagc ccaaggctgc ccctcggtc    360 actctgttcc cgccctcctc tgaggagctt caagccaaca aggccacact ggtgtgtctc    420
ataagtgact ctacccggg agccgtgaca gtggcctgga aggcagatag cagcccgtc    480 aaggcgggag tggagaccac cacccctcc aaacaaagca acaacaagta cgcggccagc    540
agctatctga gcctgacgcc tgagcagtgg aagtcccaca gaagctacag ctgccaggtc    600
acgcatgaag ggagcaccgt ggagaagaca gtggcccta cagaatgttc a             651
```

<210> SEQ ID NO 164  
<211> LENGTH: 651  
<212> TYPE: DNA  
<213> ORGANISM: Artificial  
<220> FEATURE:  
<223> OTHER INFORMATION: light chain

<400> SEQUENCE: 164

```
cagagcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtc ctaggtcagc ccaaggctgc cccctcggtc     360
actctgttcc cgccctcctc tgaggagctt caagccaaca aggccacact ggtgtgtctc     420
ataagtgact tctacccggg agccgtgaca gtggcctgga aggcagatag cagccccgtc     480
aaggcgggag tggagaccac cacaccctcc aaacaaagca caacaagta cgcggccagc      540 agctatctga gcctgacgcc tgagcagtgg aagtcccaca aagctacag ctgccaggtc       600 acgcatgaag ggagcaccgt ggagaagaca gtggccccta cagaatgttc a              651
```

<210> SEQ ID NO 165
<211> LENGTH: 651
<212> TYPE: DNA
<213> ORGANISM: Artificial
<220> FEATURE:
<223> OTHER INFORMATION: light chain

<400> SEQUENCE: 165

```
cagagcgcac tgacccagcc agcttcagtg agcggctcac caggtcagag cattaccatc      60
tcgtgtacgg gtactagcag cgatgttggt tcttataatt atgtgaattg gtaccagcag     120
catcccggga aggcgccgaa acttatgatt tatggtgttt ctaagcgtcc ctcaggcgtg     180
agcaaccgtt ttagcggatc caaaagcggc aacaccgcga gcctgaccat tagcggcctg     240
caagcggaag acgaagcgga ttattattgc ggtacttttg ctggtggttc ttattatggt     300
gtgtttggcg gcggcacgaa gttaaccgtc ctaggtcagc ccaaggctgc cccctcggtc     360
actctgttcc cgccctcctc tgaggagctt caagccaaca aggccacact ggtgtgtctc     420
ataagtgact tctacccggg agccgtgaca gtggcctgga aggcagatag cagccccgtc     480
aaggcgggag tggagaccac cacaccctcc aaacaaagca acaacaagta cgcggccagc     540
agctatctga gcctgacgcc tgagcagtgg aagtcccaca aagctacag ctgccaggtc       600 acgcatgaag ggagcaccgt ggagaagaca gtggccccta cagaatgttc a              651
```

<210> SEQ ID NO 166
<211> LENGTH: 1335
<212> TYPE: DNA
<213> ORGANISM: Artificial
<220> FEATURE:
<223> OTHER INFORMATION: heavy chain

<400> SEQUENCE: 166

```
caggtgcagc tggtgcagag cggagctgag gtgaagaagc caggcgccag cgtcaaggtg      60
tcctgcaagg ccagcggcta caccttcacc agcagctaca tcaactgggt ccgccaggct     120
cctgggcagg gactggagtg gatgggcacc atcaaccccg tgtccggcag caccagctac     180
gcccagaagt tccagggcag agtcaccatg accaggaca ccagcatcag caccgcctac      240
atggagctgt ccaggctgag aagcgacgac accgccgtgt actactgcgc caggggcggc     300
tggttcgact actgggggcca gggcaccctg gtgaccgtgt cctcagctag caccaagggc     360
ccagccgtgt tccccctggc ccccagcagc aagagcacct ccggcggcac agccgccctg     420
ggctgcctgg tgaaggacta cttccccgag cccgtgaccg tgtcctggaa cagcggagcc     480
```

```
ctgaccagcg gcgtgcacac cttccccgcc gtgctgcaga gcagcggcct gtacagcctg      540
tccagcgtgg tgacagtgcc cagcagcagc ctgggcaccc agacctacat ctgcaacgtg      600
aaccacaagc ccagcaacac caaggtggac aagagagtgg agcccaagag ctgcgacaag      660
acccacacct gccccccctg cccagccccc gaagctgcag gcggcccttc cgtgttcctg      720
ttccccccca agcccaagga caccctgatg atcagcagga ccccgaggt gacctgcgtg       780 gtggtggacg tgagccacga ggacccagag gtgaagttca actggtacgt ggacggcgtg      840
gaggtgcaca cgccaagac caagcccaga gaggagcagt acaacagcac ctacagggtg       900
gtgtccgtgc tgaccgtgct gcaccaggac tggctgaacg gcaaagaata caagtgcaag      960
gtctccaaca aggccctgcc tgcccccatc gaaaagacca tcagcaaggc caagggccag      1020
ccacgggagc cccaggtgta caccctgccc ccttctcggg aggagatgac caagaaccag      1080
gtgtccctga cctgtctggt gaagggcttc taccccagcg acatcgccgt ggagtgggag      1140
agcaacggcc agcccgagaa caactacaag accaccccc cagtgctgga cagcgacggc       1200
agcttcttcc tgtacagcaa gctgaccgtg gacaagagca ggtggcagca gggcaacgtg      1260
ttcagctgca gcgtgatgca cgaggccctg cacaaccact acacccagaa gagcctgagc      1320
ctgtcacccg gcaag                                                      1335

<210> SEQ ID NO 167
<211> LENGTH: 1335
<212> TYPE: DNA
<213> ORGANISM: Artificial
<220> FEATURE:
<223> OTHER INFORMATION: heavy chain

<400> SEQUENCE: 167
caggtgcagc tggtgcagag cggagctgag gtgaagaagc caggcgccag cgtcaaggtg      60
tcctgcaagg ccagcggcta caccttcacc agcagctaca tcaactgggt gcgccaggct      120
ccagggcagg gactggagtg gatgggccag atcaacgccg ccagcggcat gaccagatac      180
gcccagaagt tccagggcag agtcacaatg accaggggaca cctctatcag caccgcctac      240
atggagctgt ccaggctgag aagcgacgac accgccgtgt actactgcgc caggggcggc      300
tggttcgact actgggggcca gggcacccctg gtgaccgtgt cctcagctag caccaagggc      360
cccagcgtgt tccccctggc ccccagcagc aagagcacct ccggcggcac agccgccctg      420
ggctgcctgg tgaaggacta cttccccgag cccgtgaccg tgtcctggaa cagcggagcc      480
ctgaccagcg gcgtgcacac cttccccgcc gtgctgcaga gcagcggcct gtacagcctg      540
tccagcgtgg tgacagtgcc cagcagcagc ctgggcaccc agacctacat ctgcaacgtg      600
aaccacaagc ccagcaacac caaggtggac aagagagtgg agcccaagag ctgcgacaag      660
acccacacct gccccccctg cccagccccc gaagctgcag gcggcccttc cgtgttcctg      720
ttccccccca agcccaagga caccctgatg atcagcagga ccccgaggt gacctgcgtg       780 gtggtggacg tgagccacga ggacccagag gtgaagttca actggtacgt ggacggcgtg      840
gaggtgcaca cgccaagac caagcccaga gaggagcagt acaacagcac ctacagggtg       900
gtgtccgtgc tgaccgtgct gcaccaggac tggctgaacg gcaaagaata caagtgcaag      960
gtctccaaca aggccctgcc tgcccccatc gaaaagacca tcagcaaggc caagggccag      1020
ccacgggagc cccaggtgta caccctgccc ccttctcggg aggagatgac caagaaccag      1080
gtgtccctga cctgtctggt gaagggcttc taccccagcg acatcgccgt ggagtgggag      1140
agcaacggcc agcccgagaa caactacaag accaccccc cagtgctgga cagcgacggc       1200
```

| | | |
|---|---|---|
| agcttcttcc tgtacagcaa gctgaccgtg gacaagagca ggtggcagca gggcaacgtg | 1260 | |
| ttcagctgca gcgtgatgca cgaggccctg cacaaccact acacccagaa gagcctgagc | 1320 | |
| ctgtcacccg gcaag | 1335 | |

<210> SEQ ID NO 168
<211> LENGTH: 1335
<212> TYPE: DNA
<213> ORGANISM: Artificial
<220> FEATURE:
<223> OTHER INFORMATION: heavy chain

<400> SEQUENCE: 168

| | | |
|---|---|---|
| caggtgcaat tggttcagag cggcgcggaa gtgaaaaaac cgggcgcgag cgtgaaagtg | 60 | |
| agctgcaaag cctccggata tacctttact tcttcttata ttaattgggt ccgccaagcc | 120 | |
| cctgggcagg gtctcgagtg gatgggcaat attaatgctg ctgctggtat tactctttat | 180 | |
| gctcagaagt ttcagggtcg ggtcaccatg acccgtgata ccagcattag caccgcgtat | 240 | |
| atggaactga gccgcctgcg tagcgatgat acggccgtgt attattgcgc gcgtggtggt | 300 | |
| tggtttgatt attggggcca aggcaccctg gtgacggtta gctcagcctc caccaagggt | 360 | |
| ccatcggtct tccccctggc accctcctcc aagagcacct ctgggggcac agcggccctg | 420 | |
| ggctgcctgg tcaaggacta cttccccgaa ccggtgacgg tgtcgtggaa ctcaggcgcc | 480 | |
| ctgaccagcg gcgtgcacac cttcccggct gtcctacagt cctcaggact ctactccctc | 540 | |
| agcagcgtgg tgaccgtgcc ctccagcagc ttgggcaccc agacctacat ctgcaacgtg | 600 | |
| aatcacaagc ccagcaacac caaggtggac aagagagttg agcccaaatc ttgtgacaaa | 660 | |
| actcacacat gcccaccgtg cccagcacct gaagcagcgg ggggaccgtc agtcttcctc | 720 | |
| ttccccccaa aacccaagga caccctcatg atctcccgga cccctgaggt cacatgcgtg | 780 | |
| gtggtggacg tgagccacga agaccctgag gtcaagttca actggtacgt ggacggcgtg | 840 | |
| gaggtgcata atgccaagac aaagccgcgg gaggagcagt acaacagcac gtaccgggtg | 900 | |
| gtcagcgtcc tcaccgtcct gcaccaggac tggctgaatg gcaaggagta caagtgcaag | 960 | |
| gtctccaaca aagccctccc agcccccatc gagaaaacca tctccaaagc caaagggcag | 1020 | |
| ccccgagaac acaggtgta cccctgccc ccatcccggg aggagatgac caagaaccag | 1080 | |
| gtcagcctga cctgcctggt caaaggcttc tatcccagcg acatcgccgt ggagtgggag | 1140 | |
| agcaatgggc agccggagaa caactacaag accacgcctc ccgtgctgga ctccgacggc | 1200 | |
| tccttcttcc tctacagcaa gctcaccgtg gacaagagca ggtggcagca ggggaacgtc | 1260 | |
| ttctcatgct ccgtgatgca tgaggctctg cacaaccact acacgcagaa gagcctctcc | 1320 | |
| ctgtctccgg gtaaa | 1335 | |

<210> SEQ ID NO 169
<211> LENGTH: 1335
<212> TYPE: DNA
<213> ORGANISM: Artificial
<220> FEATURE:
<223> OTHER INFORMATION: heavy chain

<400> SEQUENCE: 169

| | | |
|---|---|---|
| caggtgcaat tggttcagag cggcgcggaa gtgaaaaaac cgggcgcgag cgtgaaagtg | 60 | |
| agctgcaaag cctccggata tacctttact tcttcttata ttaattgggt ccgccaagcc | 120 | |
| cctgggcagg gtctcgagtg gatgggcggt attaatcctc tgctggtac tacttcttat | 180 | |
| gctcagaagt ttcagggtcg ggtcaccatg acccgtgata ccagcattag caccgcgtat | 240 | |

```
atggaactga gccgcctgcg tagcgatgat acggccgtgt attattgcgc gcgtggtggt      300
tggtttgatt attggggcca aggcaccctg gtgacggtta gctcagcctc caccaagggt      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaagcagcgg ggggaccgtc agtcttcctc      720
ttccccccaa aacccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgggtg      900
gtcagcgtcc tcaccgtcct gcaccaggac tggctgaatg gcaaggagta caagtgcaag      960
gtctccaaca aagccctccc agcccccatc gagaaaacca tctccaaagc caaagggcag     1020
ccccgagaac cacaggtgta caccctgccc ccatcccggg aggagatgac caagaaccag     1080
gtcagcctga cctgcctggt caaaggcttc tatcccagcg acatcgccgt ggagtgggag     1140
agcaatgggc agccggagaa caactacaag accacgcctc ccgtgctgga ctccgacggc     1200
tccttcttcc tctacagcaa gctcaccgtg gacaagagca ggtggcagca ggggaacgtc     1260
ttctcatgct ccgtgatgca tgaggctctg cacaaccact acacgcagaa gagcctctcc     1320
ctgtctccgg gtaaa                                                      1335

<210> SEQ ID NO 170
<211> LENGTH: 1335
<212> TYPE: DNA
<213> ORGANISM: Artificial
<220> FEATURE:
<223> OTHER INFORMATION: heavy chain

<400> SEQUENCE: 170
caggtgcaat tggttcagag cggcgcggaa gtgaaaaaac cgggcgcgag cgtgaaagtg       60
agctgcaaag cctccggata tacctttact tcttcttata ttaattgggt ccgccaagcc      120
cctgggcagg gtctcgagtg gatgggcaat attaatcctg ctactggtca tgctgattat      180
gctcagaagt ttcagggtcg ggtgaccatg acccgtgata ccagcattag caccgcgtat      240
atggaactga gccgcctgcg tagcgatgat acggccgtgt attattgcgc gcgtggtggt      300
tggtttgatt attggggcca aggcaccctg gtgacggtta gctcagcctc caccaagggt      360
ccatcggtct tccccctggc accctcctcc aagagcacct ctgggggcac agcggccctg      420
ggctgcctgg tcaaggacta cttccccgaa ccggtgacgg tgtcgtggaa ctcaggcgcc      480
ctgaccagcg gcgtgcacac cttcccggct gtcctacagt cctcaggact ctactccctc      540
agcagcgtgg tgaccgtgcc ctccagcagc ttgggcaccc agacctacat ctgcaacgtg      600
aatcacaagc ccagcaacac caaggtggac aagagagttg agcccaaatc ttgtgacaaa      660
actcacacat gcccaccgtg cccagcacct gaagcagcgg ggggaccgtc agtcttcctc      720
ttccccccaa aacccaagga caccctcatg atctcccgga cccctgaggt cacatgcgtg      780
gtggtggacg tgagccacga agaccctgag gtcaagttca actggtacgt ggacggcgtg      840
gaggtgcata atgccaagac aaagccgcgg gaggagcagt acaacagcac gtaccgggtg      900
gtcagcgtcc tcaccgtcct gcaccaggac tggctgaatg gcaaggagta caagtgcaag      960
```

```
gtctccaaca aagccctccc agccccatc gagaaaacca tctccaaagc caaagggcag    1020
ccccgagaac cacaggtgta caccctgccc ccatcccggg aggagatgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagcc ggtggcagca ggggaacgtc    1260
ttctcatgct ccgtgatgca tgaggctctg cacaaccact acacgcagaa gagcctctcc    1320
ctgtctccgg gtaaa                                                     1335
```

<210> SEQ ID NO 171
<211> LENGTH: 651
<212> TYPE: DNA
<213> ORGANISM: Artificial
<220> FEATURE:
<223> OTHER INFORMATION: light chain

<400> SEQUENCE: 171

```
cagagcgccc tgacccagcc cgccagcgtg tccggcagcc caggccagtc tatcacaatc     60
agctgcaccg gcacctccag cgacgtgggc agctacaact acgtgaactg gtatcagcag    120
caccccggca aggcccccaa gctgatgatc tacggcgtga gcaagaggcc cagcggcgtg    180
tccaacaggt tcagcggcag caagagcggc aacaccgcca gcctgacaat cagtgggctg    240
caggctgagg acgaggccga ctactactgc ggcacctttg ccggcggatc atactacggc    300
gtgttcggcg agggaccaa gctgaccgtg ctgggccagc ctaaggctgc ccccagcgtg    360
accctgttcc cccccagcag cgaggagctg caggccaaca aggccaccct ggtgtgcctg    420
atcagcgact tctacccagg cgccgtgacc gtggcctgga aggccgacag cagccccgtg    480
aaggccggcg tggagaccac cacccccagc aagcagagca acaacaagta cgccgccagc    540
agctacctga gcctgacccc cgagcagtgg aagagccaca ggtcctacag ctgccaggtg    600
acccacgagg gcagcaccgt ggaaaagacc gtggcccccaa ccgagtgcag c            651
```

<210> SEQ ID NO 172
<211> LENGTH: 651
<212> TYPE: DNA
<213> ORGANISM: Artificial
<220> FEATURE:
<223> OTHER INFORMATION: light chain

<400> SEQUENCE: 172

```
cagagcgccc tgacccagcc cgccagcgtg tccggcagcc caggccagtc tatcacaatc     60
agctgcaccg gcacctccag cgacgtgggc agctacaact acgtgaactg gtatcagcag    120
caccccggca aggcccccaa gctgatgatc tacggcgtga gcaagaggcc cagcggcgtg    180
tccaacaggt tcagcggcag caagagcggc aacaccgcca gcctgacaat cagtgggctg    240
caggctgagg acgaggccga ctactactgc ggcacctttg ccggcggatc atactacggc    300
gtgttcggcg agggaccaa gctgaccgtg ctgggccagc ctaaggctgc ccccagcgtg    360
accctgttcc cccccagcag cgaggagctg caggccaaca aggccaccct ggtgtgcctg    420
atcagcgact tctacccagg cgccgtgacc gtggcctgga aggccgacag cagccccgtg    480
aaggccggcg tggagaccac cacccccagc aagcagagca acaacaagta cgccgccagc    540
agctacctga gcctgacccc cgagcagtgg aagagccaca ggtcctacag ctgccaggtg    600
acccacgagg gcagcaccgt ggaaaagacc gtggcccccaa ccgagtgcag c            651
```

<210> SEQ ID NO 173
<211> LENGTH: 651
<212> TYPE: DNA
<213> ORGANISM: Artificial
<220> FEATURE:
<223> OTHER INFORMATION: light chain

<400> SEQUENCE: 173

| | | | | | |
|---|---|---|---|---|---|
| cagagcgcac | tgacccagcc | agcttcagtg | agcggctcac | caggtcagag | cattaccatc | 60 |
| tcgtgtacgg | gtactagcag | cgatgttggt | tcttataatt | atgtgaattg | gtaccagcag | 120 |
| catcccggga | aggcgccgaa | acttatgatt | tatggtgttt | ctaagcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | ggtacttttg | ctggtggttc | ttattatggt | 300 |
| gtgtttggcg | gcggcacgaa | gttaaccgtc | ctaggtcagc | ccaaggctgc | ccctcggtc | 360 |
| actctgttcc | cgccctcctc | tgaggagctt | caagccaaca | aggccacact | ggtgtgtctc | 420 |
| ataagtgact | tctacccggg | agccgtgaca | gtggcctgga | aggcagatag | cagccccgtc | 480 |
| aaggcgggag | tggagaccac | cacaccctcc | aaacaaagca | acaacaagta | cgcggccagc | 540 |
| agctatctga | gcctgacgcc | tgagcagtgg | aagtcccaca | gaagctacag | ctgccaggtc | 600 |
| acgcatgaag | ggagcaccgt | ggagaagaca | gtggccccta | cagaatgttc | a | 651 |

<210> SEQ ID NO 174
<211> LENGTH: 651
<212> TYPE: DNA
<213> ORGANISM: Artificial
<220> FEATURE:
<223> OTHER INFORMATION: light chain

<400> SEQUENCE: 174

| | | | | | |
|---|---|---|---|---|---|
| cagagcgcac | tgacccagcc | agcttcagtg | agcggctcac | caggtcagag | cattaccatc | 60 |
| tcgtgtacgg | gtactagcag | cgatgttggt | tcttataatt | atgtgaattg | gtaccagcag | 120 |
| catcccggga | aggcgccgaa | acttatgatt | tatggtgttt | ctaagcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | ggtacttttg | ctggtggttc | ttattatggt | 300 |
| gtgtttggcg | gcggcacgaa | gttaaccgtc | ctaggtcagc | ccaaggctgc | ccctcggtc | 360 |
| actctgttcc | cgccctcctc | tgaggagctt | caagccaaca | aggccacact | ggtgtgtctc | 420 |
| ataagtgact | tctacccggg | agccgtgaca | gtggcctgga | aggcagatag | cagccccgtc | 480 |
| aaggcgggag | tggagaccac | cacaccctcc | aaacaaagca | acaacaagta | cgcggccagc | 540 |
| agctatctga | gcctgacgcc | tgagcagtgg | aagtcccaca | gaagctacag | ctgccaggtc | 600 |
| acgcatgaag | ggagcaccgt | ggagaagaca | gtggccccta | cagaatgttc | a | 651 |

<210> SEQ ID NO 175
<211> LENGTH: 651
<212> TYPE: DNA
<213> ORGANISM: Artificial
<220> FEATURE:
<223> OTHER INFORMATION: light chain

<400> SEQUENCE: 175

| | | | | | |
|---|---|---|---|---|---|
| cagagcgcac | tgacccagcc | agcttcagtg | agcggctcac | caggtcagag | cattaccatc | 60 |
| tcgtgtacgg | gtactagcag | cgatgttggt | tcttataatt | atgtgaattg | gtaccagcag | 120 |
| catcccggga | aggcgccgaa | acttatgatt | tatggtgttt | ctaagcgtcc | ctcaggcgtg | 180 |
| agcaaccgtt | ttagcggatc | caaaagcggc | aacaccgcga | gcctgaccat | tagcggcctg | 240 |

-continued

| | |
|---|---|
| caagcggaag acgaagcgga ttattattgc ggtacttttg ctggtggttc ttattatggt | 300 |
| gtgtttggcg gcggcacgaa gttaaccgtc ctaggtcagc ccaaggctgc ccctcggtc | 360 |
| actctgttcc cgcccctcctc tgaggagctt caagccaaca aggccacact ggtgtgtctc | 420 |
| ataagtgact tctacccggg agccgtgaca gtggcctgga aggcagatag cagccccgtc | 480 |
| aaggcgggag tggagaccac cacaccctcc aaacaaagca caacaagta cgcggccagc | 540 |
| agctatctga gcctgacgcc tgagcagtgg aagtcccaca gaagctacag ctgccaggtc | 600 |
| acgcatgaag ggagcaccgt ggagaagaca gtggccccta cagaatgttc a | 651 |

<210> SEQ ID NO 176
<211> LENGTH: 1323
<212> TYPE: DNA
<213> ORGANISM: Artificial
<220> FEATURE:
<223> OTHER INFORMATION: heavy chain

<400> SEQUENCE: 176

| | |
|---|---|
| caggtgcagc tggtgcagag cggagctgag gtgaagaagc caggcgccag cgtcaaggtg | 60 |
| tcctgcaagg ccagcggcta caccttcacc agcagctaca tcaactgggt ccgccaggct | 120 |
| cctgggcagg gactggagtg gatgggcacc atcaaccccg tgtccggcag caccagctac | 180 |
| gcccagaagt tccagggcag agtcaccatg accaggaca ccagcatcag caccgcctac | 240 |
| atggagctgt ccaggctgag aagcgacgac accgccgtgt actactgcgc caggggcggc | 300 |
| tggttcgact actggggcca gggcaccctg gtgaccgtgt cctcagctag caccaagggc | 360 |
| cccagcgtgt tccccctggc ccctgcagc agaagcacca gcgagagcac agccgccctg | 420 |
| ggctgcctgt gaaggacta cttccccgag ccagtgaccg tgtcctggaa cagcggagcc | 480 |
| ctgaccagcg gcgtgcacac cttccccgcc gtgctgcaga gcagcggcct gtacagcctg | 540 |
| tccagcgtgg tgaccgtgcc cagcagcaac ttcggcaccc agacctacac ctgcaacgtg | 600 |
| gaccacaagc ccagcaacac caaggtggac aagaccgtgg agaggaagtg ctgcgtggag | 660 |
| tgccccccct gcccagcccc ccagtggcc ggaccctccg tgttcctgtt ccccccaag | 720 |
| cccaaggaca ccctgatgat cagcaggacc cccgaggtga cctgcgtggt ggtggacgtg | 780 |
| agccacgagg acccagaggt gcagttcaac tggtacgtgg acggcgtgga ggtgcacaac | 840 |
| gccaagacca gcccagaga ggaacagttt aacagcacct tcagggtggt gtccgtgctg | 900 |
| accgtggtgc accaggactg gctgaacggc aaagagtaca agtgcaaggt ctccaacaag | 960 |
| ggcctgccag ccccatcga gaaaaccatc agcaagacca agggccagcc acgggagccc | 1020 |
| caggtgtaca ccctgccccc cagccgggag gaaatgacca gaaccaggt gtccctgacc | 1080 |
| tgtctggtga agggcttcta ccccagcgac atcgccgtgg agtgggagag caacggccag | 1140 |
| cccgagaaca actacaagac caccccccc atgctggaca cgacggcag cttcttcctg | 1200 |
| tacagcaagc tgacagtgga caagagcagg tggcagcagg gcaacgtgtt cagctgcagc | 1260 |
| gtgatgcacg aggccctgca caaccactac acccagaaga gcctgagcct gtccccggc | 1320 |
| aag | 1323 |

<210> SEQ ID NO 177
<211> LENGTH: 1323
<212> TYPE: DNA
<213> ORGANISM: Artificial
<220> FEATURE:
<223> OTHER INFORMATION: heavy chain

<400> SEQUENCE: 177

```
caggtgcagc tggtgcagag cggagctgag gtgaagaagc caggcgccag cgtcaaggtg      60
tcctgcaagg ccagcggcta caccttcacc agcagctaca tcaactgggt gcgccaggct     120
ccagggcagg gactggagtg gatgggccag atcaacgccg ccagcggcat gaccagatac     180
gcccagaagt tccagggcag agtcacaatg accagggaca cctctatcag caccgcctac     240
atggagctgt ccaggctgag aagcgacgac accgccgtgt actactgcgc caggggcggc     300
tggttcgact actggggcca gggcaccctg gtgaccgtgt cctcagctag caccaagggc     360
cccagcgtgt tccccctggc ccctgcagc agaagcacca gcgagagcac agccgccctg     420
ggctgcctgg tgaaggacta cttccccgag ccagtgaccg tgtcctggaa cagcggagcc     480
ctgaccagcg gcgtgcacac cttccccgcc gtgctgcaga gcagcggcct gtacagcctg     540
tccagcgtgg tgaccgtgcc cagcagcaac ttcggcaccc agacctacac ctgcaacgtg     600
gaccacaagc ccagcaacac caaggtggac aagaccgtgg agaggaagtg ctgcgtggag     660
tgccccccct gcccagcccc cccagtggcc ggaccctccg tgttcctgtt ccccccaag      720
cccaaggaca ccctgatgat cagcaggacc cccgaggtga cctgcgtggt ggtggacgtg     780
agccacgagg acccagaggt gcagttcaac tggtacgtgg acggcgtgga ggtgcacaac     840
gccaagacca gcccagaga ggaacagttt aacagcacct tcagggtggt gtccgtgctg     900
accgtggtgc accaggactg gctgaacggc aagagtaca agtgcaaggt ctccaacaag     960
ggcctgccag cccccatcga gaaaaccatc agcaagacca agggccagcc acgggagccc    1020
caggtgtaca ccctgccccc cagccgggag gaaatgacca gaaccaggt gtccctgacc    1080
tgtctggtga agggcttcta ccccagcgac atcgccgtgg agtgggagag caacggccag    1140
cccgagaaca actacaagac cacccccccc atgctggaca cgacggcag cttcttcctg    1200
tacagcaagc tgacagtgga caagagcagg tggcagcagg gcaacgtgtt cagctgcagc    1260
gtgatgcacg aggccctgca caaccactac acccagaaga gcctgagcct gtcccccggc    1320
aag                                                                  1323

<210> SEQ ID NO 178
<211> LENGTH: 1323
<212> TYPE: DNA
<213> ORGANISM: Artificial
<220> FEATURE:
<223> OTHER INFORMATION: heavy chain

<400> SEQUENCE: 178
caggtgcaat tggttcagag cggcgcggaa gtgaaaaaac cgggcgcgag cgtgaaagtg      60
agctgcaaag cctccggata cctttact tcttcttata ttaattgggt ccgccaagcc      120
cctgggcagg gtctcgagtg gatgggcaat attaatgctg ctgctggtat tactctttat     180
gctcagaagt ttcagggtcg ggtcaccatg accgtgata ccagcattag caccgcgtat     240
atggaactga gccgcctgcg tagcgatgat acggccgtgt attattgcgc gcgtggtggt     300
tggtttgatt attggggcca aggcaccctg gtgacggtta gctcagcttc caccaagggc     360
cccagcgtgt tccccctggc ccctgcagc agaagcacca gcgagagcac agccgccctg     420
ggctgcctgg tgaaggacta cttccccgag cccgtgaccg tgagctggaa cagcggagcc     480
ctgaccagcg gcgtgcacac cttccccgcc gtgctgcaga gcagcggcct gtacagcctg     540
agcagcgtgg tgaccgtgcc cagcagcaac ttcggcaccc agacctacac ctgcaacgtg     600
gaccacaagc ccagcaacac caaggtggac aagaccgtgg agcggaagtg ctgcgtggag     660
tgcccccct gccctgcccc tcctgtggcc ggaccctccg tgttcctgtt ccccccaag      720
```

| | |
|---|---|
| cccaaggaca ccctgatgat cagccggacc cccgaggtga cctgcgtggt ggtggacgtg | 780 |
| agccacgagg accccgaggt gcagttcaac tggtacgtgg acggcgtgga ggtgcacaac | 840 |
| gccaagacca agccccggga ggaacagttc aacagcacct tccgggtggt gtccgtgctg | 900 |
| accgtggtgc accaggactg gctgaacggc aagaataca agtgcaaggt gtccaacaag | 960 |
| ggcctgcctg cccccatcga aaaaccatc agcaagacaa agggccagcc cagggaaccc | 1020 |
| caggtgtaca ccctgccccc cagccgggag gaaatgacca agaaccaggt gtccctgacc | 1080 |
| tgtctggtga agggcttcta ccccagcgac atcgccgtgg agtgggagag caacggccag | 1140 |
| cccgagaaca actacaagac cacccccccc atgctggaca cgacggcag cttcttcctg | 1200 |
| tacagcaagc tgacagtgga caagagccgg tggcagcagg gcaacgtgtt cagctgcagc | 1260 |
| gtgatgcacg aggccctgca caaccactac acccagaaga gcctgagcct gtcccccggc | 1320 |
| aaa | 1323 |

<210> SEQ ID NO 179
<211> LENGTH: 1323
<212> TYPE: DNA
<213> ORGANISM: Artificial
<220> FEATURE:
<223> OTHER INFORMATION: heavy chain

<400> SEQUENCE: 179

| | |
|---|---|
| caggtgcaat tggttcagag cggcgcggaa gtgaaaaaac cgggcgcgag cgtgaaagtg | 60 |
| agctgcaaag cctccggata tacctttact tcttcttata ttaattgggt ccgccaagcc | 120 |
| cctgggcagg gtctcgagtg gatgggcggt attaatcctc ctgctggtac tacttcttat | 180 |
| gctcagaagt ttcagggtcg ggtcaccatg accgtgata ccagcattag caccgcgtat | 240 |
| atggaactga gccgcctgcg tagcgatgat acggccgtgt attattgcgc gcgtggtggt | 300 |
| tggtttgatt attggggcca aggcaccctg gtgacggtta gctcagcttc caccaagggc | 360 |
| ccagcgtgt tcccctggc ccctgcagc agaagcacca gcgagagcac agccgccctg | 420 |
| ggctgcctgg tgaaggacta cttccccgag cccgtgaccg tgagctggaa cagcggagcc | 480 |
| ctgaccagcg gcgtgcacac cttccccgcc gtgctgcaga gcagcggcct gtacagcctg | 540 |
| agcagcgtgt gaccgtgcc agcagcaac ttcggcaccc agacctacac ctgcaacgtg | 600 |
| gaccacaagc ccagcaacac caaggtggac aagaccgtgg agcggaagtg ctgcgtggag | 660 |
| tgccccccct gccctgcccc tcctgtggcc ggaccctccg tgttcctgtt ccccccaag | 720 |
| cccaaggaca ccctgatgat cagccggacc cccgaggtga cctgcgtggt ggtggacgtg | 780 |
| agccacgagg accccgaggt gcagttcaac tggtacgtgg acggcgtgga ggtgcacaac | 840 |
| gccaagacca agccccggga ggaacagttc aacagcacct tccgggtggt gtccgtgctg | 900 |
| accgtggtgc accaggactg gctgaacggc aagaataca agtgcaaggt gtccaacaag | 960 |
| ggcctgcctg cccccatcga aaaaccatc agcaagacaa agggccagcc cagggaaccc | 1020 |
| caggtgtaca ccctgccccc cagccgggag gaaatgacca agaaccaggt gtccctgacc | 1080 |
| tgtctggtga agggcttcta ccccagcgac atcgccgtgg agtgggagag caacggccag | 1140 |
| cccgagaaca actacaagac cacccccccc atgctggaca cgacggcag cttcttcctg | 1200 |
| tacagcaagc tgacagtgga caagagccgg tggcagcagg gcaacgtgtt cagctgcagc | 1260 |
| gtgatgcacg aggccctgca caaccactac acccagaaga gcctgagcct gtcccccggc | 1320 |
| aaa | 1323 |

<210> SEQ ID NO 180
<211> LENGTH: 1323
<212> TYPE: DNA
<213> ORGANISM: Artificial
<220> FEATURE:
<223> OTHER INFORMATION: heavy chain

<400> SEQUENCE: 180

```
caggtgcaat tggttcagag cggcgcggaa gtgaaaaaac cgggcgcgag cgtgaaagtg      60
agctgcaaag cctccggata tacctttact tcttcttata ttaattgggt ccgccaagcc     120
cctgggcagg gtctcgagtg gatgggcaat attaatcctg ctactggtca tgctgattat     180
gctcagaagt ttcagggtcg ggtgaccatg acccgtgata ccagcattag caccgcgtat     240
atggaactga ccgcctgcg tagcgatgat acggccgtgt attattgcgc gcgtggtggt     300
tggtttgatt attggggcca aggcaccctg gtgacggtta gctcagcttc caccaagggc     360
ccaagcgtgt tccccctggc ccctgcagc agaagcacca gcgagagcac agccgccctg     420
ggctgcctgg tgaaggacta cttccccgag cccgtgaccg tgagctggaa cagcggagcc     480
ctgaccagcg gcgtgcacac cttccccgcc gtgctgcaga gcagcggcct gtacagcctg     540
agcagcgtgg tgaccgtgcc cagcagcaac ttcggcaccc agacctacac ctgcaacgtg     600
gaccacaagc ccagcaacac caaggtggac aagaccgtgg agcggaagtg ctgcgtggag     660
tgcccccct gccctgcccc tcctgtggcc ggacccctccg tgttcctgtt ccccccccaag    720
cccaaggaca cctgatgat cagccggacc cccgaggtga cctgcgtggt ggtggacgtg     780
agccacgagg accccgaggt gcagttcaac tggtacgtgg acggcgtgga ggtgcacaac     840
gccaagacca gccccgggga ggaacagttc aacagcacct tccgggtggt gtccgtgctg     900
accgtggtgc accaggactg gctgaacggc aagaatacaa agtgcaaggt gtccaacaag     960
ggcctgcctg cccccatcga gaaaccatc agcaagacaa agggccagcc cagggaaccc    1020
caggtgtaca ccctgccccc cagccgggag gaaatgacca gaaccaggt gtccctgacc    1080
tgtctggtga agggcttcta ccccagcgac atcgccgtgg agtgggagag caacggccag    1140
cccgagaaca actacaagac caccccccc atgctggaca cgacggcag cttcttcctg    1200
tacagcaagc tgacagtgga caagagccgg tggcagcagg gcaacgtgtt cagctgcagc    1260
gtgatgcacg aggccctgca caaccactac acccagaaga gcctgagcct gtcccccggc    1320
aaa                                                                 1323
```

<210> SEQ ID NO 181
<211> LENGTH: 512
<212> TYPE: PRT
<213> ORGANISM: Homo sapiens

<400> SEQUENCE: 181

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95
```

```
Pro Gln Val Tyr Phe Cys Cys Glu Gly Asn Phe Cys Asn Glu Arg
        100                 105                 110

Phe Thr His Leu Pro Glu Ala Gly Pro Glu Val Thr Tyr Glu Pro
        115                 120                 125

Pro Pro Thr Ala Pro Thr Leu Leu Thr Val Leu Ala Tyr Ser Leu Leu
130             135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
                180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225             230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
                260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
        290                 295                 300

Val Pro Trp Cys Arg Gly Glu Gly His Lys Pro Ser Ile Ala His Arg
305             310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385             390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Ala Cys Trp Asp His Asp
    450                 455                 460

Ala Glu Ala Arg Leu Ser Ala Gly Cys Val Glu Glu Arg Val Ser Leu
465             470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510
```

```
<210> SEQ ID NO 182
<211> LENGTH: 116
<212> TYPE: PRT
<213> ORGANISM: Homo sapiens

<400> SEQUENCE: 182

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 183
<211> LENGTH: 15
<212> TYPE: PRT
<213> ORGANISM: Homo sapiens

<400> SEQUENCE: 183

Ile Glu Leu Val Lys Lys Gly Ser Trp Leu Asp Asp Phe Asn Ser
1               5                   10                  15

<210> SEQ ID NO 184
<211> LENGTH: 15
<212> TYPE: PRT
<213> ORGANISM: Homo sapiens

<400> SEQUENCE: 184

Val Lys Lys Gly Ser Trp Leu Asp Asp Phe Asn Ser Tyr Asp Arg
1               5                   10                  15

<210> SEQ ID NO 185
<211> LENGTH: 15
<212> TYPE: PRT
<213> ORGANISM: Homo sapiens

<400> SEQUENCE: 185

Gly Ser Trp Leu Asp Asp Phe Asn Ser Tyr Asp Arg Gln Glu Ser
1               5                   10                  15

<210> SEQ ID NO 186
<211> LENGTH: 9
<212> TYPE: PRT
<213> ORGANISM: Homo sapiens

<400> SEQUENCE: 186

Gly Cys Trp Leu Asp Asp Phe Asn Cys
1               5

<210> SEQ ID NO 187
<211> LENGTH: 15
<212> TYPE: PRT
<213> ORGANISM: Homo sapiens
```

```
<400> SEQUENCE: 187

Cys Glu Gly Glu Gln Asp Lys Arg Leu His Cys Tyr Ala Ser Trp
1               5                   10                  15

<210> SEQ ID NO 188
<211> LENGTH: 6
<212> TYPE: PRT
<213> ORGANISM: Homo sapiens

<400> SEQUENCE: 188

Trp Leu Asp Asp Phe Asn
1               5

<210> SEQ ID NO 189
<211> LENGTH: 5
<212> TYPE: PRT
<213> ORGANISM: Homo sapiens

<400> SEQUENCE: 189

Glu Gln Asp Lys Arg
1               5

<210> SEQ ID NO 190
<211> LENGTH: 11
<212> TYPE: PRT
<213> ORGANISM: Homo sapiens

<400> SEQUENCE: 190

Lys Gly Cys Trp Leu Asp Asp Phe Asn Cys Tyr
1               5                   10
```